(12) United States Patent
Quijano et al.

(10) Patent No.: US 12,005,121 B2
(45) Date of Patent: *Jun. 11, 2024

(54) COMPOSITIONS AND METHODS FOR DELIVERY OF NUCLEIC ACIDS TO CELLS

(71) Applicant: Yale University, New Haven, CT (US)

(72) Inventors: Elias Quijano, Durham, CT (US);
Peter Glazer, Guilford, CT (US)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/823,492

(22) Filed: Aug. 30, 2022

(65) Prior Publication Data

US 2023/0032060 A1 Feb. 2, 2023

Related U.S. Application Data

(63) Continuation of application No. 17/638,642, filed as application No. PCT/US2020/048823 on Aug. 31, 2020, which is a continuation-in-part of application No. PCT/US2019/048962, filed on Aug. 30, 2019, and a continuation-in-part of application No. PCT/US2019/048953, filed on Aug. 30, 2019.

(60) Provisional application No. 62/944,281, filed on Dec. 5, 2019.

(51) Int. Cl.
| | |
|---|---|
| *A61K 47/54* | (2017.01) |
| *A61K 39/00* | (2006.01) |
| *A61K 47/68* | (2017.01) |
| *A61K 48/00* | (2006.01) |
| *A61P 35/00* | (2006.01) |
| *C07K 14/47* | (2006.01) |
| *C07K 14/52* | (2006.01) |
| *C07K 16/44* | (2006.01) |
| *C12N 15/11* | (2006.01) |
| *C12N 15/113* | (2010.01) |
| *C12N 15/87* | (2006.01) |

(52) U.S. Cl.
CPC ........ *A61K 47/549* (2017.08); *A61K 47/6807* (2017.08); *A61K 47/6851* (2017.08); *A61K 48/0025* (2013.01); *A61K 48/005* (2013.01); *A61P 35/00* (2018.01); *C07K 14/4747* (2013.01); *C07K 14/52* (2013.01); *C07K 16/44* (2013.01); *C12N 15/111* (2013.01); *C12N 15/113* (2013.01); *C12N 15/1135* (2013.01); *C12N 15/87* (2013.01); *A61K 2039/505* (2013.01); *A61K 48/00* (2013.01); *C07K 2317/24* (2013.01); *C07K 2317/31* (2013.01); *C07K 2317/565* (2013.01); *C07K 2317/622* (2013.01); *C07K 2317/77* (2013.01); *C07K 2319/33* (2013.01); *C12N 2310/11* (2013.01); *C12N 2310/14* (2013.01); *C12N 2310/3181* (2013.01); *C12N 2310/3513* (2013.01); *C12N 2320/32* (2013.01)

(58) Field of Classification Search
CPC .......... A61P 35/00; A61P 35/02; A61K 47/00; A61K 48/005; A61K 2039/505
See application file for complete search history.

(56) References Cited

U.S. PATENT DOCUMENTS

| | | |
|---|---|---|
| 4,714,680 A | 12/1987 | Civin |
| 4,812,397 A | 3/1989 | Weisbart |
| 4,965,204 A | 10/1990 | Civin |
| 5,034,506 A | 7/1991 | Summerton et al. |
| 5,061,620 A | 10/1991 | Tsukamoto et al. |
| 5,075,109 A | 12/1991 | Tice et al. |
| 5,142,047 A | 8/1992 | Summmerton et al. |
| 5,166,315 A | 11/1992 | Summerton et al. |
| 5,217,866 A | 6/1993 | Summerton et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,506,337 A | 4/1996 | Summerton et al. |
| 5,521,063 A | 5/1996 | Summerton et al. |
| 5,527,675 A | 6/1996 | Coull et al. |
| 5,539,082 A | 7/1996 | Nielsen et al. |
| 5,623,049 A | 4/1997 | Löbberding et al. |
| 5,643,741 A | 7/1997 | Tsukamoto et al. |

(Continued)

FOREIGN PATENT DOCUMENTS

| | | | |
|---|---|---|---|
| CN | 1986792 A | * | 6/2007 |
| CN | 111218458 | | 6/2020 |

(Continued)

OTHER PUBLICATIONS

Nishio et al (Cancer Science, 2011, vol. 102, pp. 622-629) (Year: 2011).*
Byles et al, International Journal of biological Sciences, 2010, vol. 6, pp. 599-612 (Year: 2010).*
Seshacharyulu et al, Cancer Letters, 2013, vol. 335, pp. 9-18 (Year: 2013).*
Translation of specification of CN1986792A downloaded from the Web Dec. 21, 2022 (Year: 2022).*
Translation of claims of CN1986792A downloaded from the Web Dec. 21, 2022 (Year: 2022).*

(Continued)

*Primary Examiner* — Karen A. Canella
(74) *Attorney, Agent, or Firm* — STERNE, KESSLER, GOLDSTEIN & FOX P.L.L.C.

(57) ABSTRACT

Compositions and methods of use thereof for delivering nucleic acid cargo into cells are provided. The compositions typically include (a) a 3E10 monoclonal antibody or an antigen binding, cell-penetrating fragment thereof; a monovalent, divalent, or multivalent single chain variable fragment (scFv); or a diabody; or humanized form or variant thereof, and (b) a nucleic acid cargo including, for example, a nucleic acid encoding a polypeptide, a functional nucleic acid, a nucleic acid encoding a functional nucleic acid, or a combination thereof. Elements (a) and (b) are typically non-covalently linked to form a complex.

22 Claims, 22 Drawing Sheets
Specification includes a Sequence Listing.

(56) References Cited

U.S. PATENT DOCUMENTS

| | | | |
|---|---|---|---|
| 5,677,136 | A | 10/1997 | Simmons et al. |
| 5,698,685 | A | 12/1997 | Summerton |
| 5,714,331 | A | 2/1998 | Buchardt et al. |
| 5,716,827 | A | 2/1998 | Tsukamoto et al. |
| 5,736,336 | A | 4/1998 | Buchardt et al. |
| 5,750,397 | A | 5/1998 | Tsukamoto et al. |
| 5,759,793 | A | 6/1998 | Schwartz et al. |
| 5,773,571 | A | 6/1998 | Nielsen et al. |
| 5,786,571 | A | 7/1998 | Bethel et al. |
| 5,945,337 | A | 8/1999 | Brown |
| 6,140,081 | A | 10/2000 | Barbas |
| 6,261,841 | B1 | 7/2001 | Cohen et al. |
| 6,453,242 | B1 | 9/2002 | Eisenberg et al. |
| 6,534,261 | B1 | 3/2003 | Cox, III et al. |
| 6,610,512 | B1 | 8/2003 | Barbas |
| 6,746,838 | B1 | 6/2004 | Choo et al. |
| 6,866,997 | B1 | 3/2005 | Choo et al. |
| 6,919,208 | B2 | 7/2005 | Levy et al. |
| 7,067,617 | B2 | 6/2006 | Barbas, III et al. |
| 7,189,396 | B1 | 3/2007 | Weisbart |
| RE46,211 | E | 11/2016 | Weisbart |
| 9,610,362 | B2 | 4/2017 | Armstrong |
| 9,732,146 | B2 | 8/2017 | Nishimura et al. |
| 10,017,581 | B2 | 7/2018 | Armstrong et al. |
| 2002/0165356 | A1 | 11/2002 | Barbas, III et al. |
| 2004/0197892 | A1 | 10/2004 | Moore et al. |
| 2007/0154989 | A1 | 7/2007 | Barbas, III |
| 2007/0213269 | A1 | 9/2007 | Barbas, III et al. |
| 2011/0145940 | A1 | 6/2011 | Voytas et al. |
| 2013/0071414 | A1 | 3/2013 | Dotti et al. |
| 2013/0266570 | A1 | 10/2013 | Weisbart |
| 2014/0050709 | A1 | 2/2014 | Leen et al. |
| 2014/0342003 | A1 | 11/2014 | Saltzman et al. |
| 2015/0017120 | A1 | 1/2015 | Wittrup et al. |
| 2015/0283178 | A1 | 10/2015 | June et al. |
| 2015/0290244 | A1 | 10/2015 | June et al. |
| 2017/0281795 | A1 | 10/2017 | Geall et al. |
| 2021/0338815 | A1 | 11/2021 | Quijano et al. |
| 2021/0340280 | A1 | 11/2021 | Quijano et al. |
| 2023/0085308 | A1 | 3/2023 | Quijano et al. |
| 2023/0093460 | A1 | 3/2023 | Quijano et al. |

FOREIGN PATENT DOCUMENTS

| | | |
|---|---|---|
| WO | WO-1997032602 A1 | 9/1997 |
| WO | WO-199853059 A1 | 11/1998 |
| WO | WO-200244321 A2 | 6/2002 |
| WO | WO-2003016496 A2 | 2/2003 |
| WO | WO-2006024518 A1 | 3/2006 |
| WO | WO-2008091911 A2 | 7/2008 |
| WO | WO-2011072246 A2 | 6/2011 |
| WO | WO-2012135831 A1 | 10/2012 |
| WO | WO-2013082529 A1 | 6/2013 |
| WO | WO-2013138662 A1 | 9/2013 |
| WO | WO-2013176772 A1 | 11/2013 |
| WO | WO-2014018423 A2 | 1/2014 |
| WO | WO-2015106290 A1 | 7/2015 |
| WO | WO-2015134607 A1 | 9/2015 |
| WO | WO-2016033321 A1 | 3/2016 |
| WO | WO-2016033324 A1 | 3/2016 |
| WO | WO-2016081621 A1 | 5/2016 |
| WO | WO-2017015101 A1 | 1/2017 |
| WO | WO-2017015630 A2 | 1/2017 |
| WO | WO-2017143042 A2 | 8/2017 |
| WO | WO-2017218825 A1 | 12/2017 |
| WO | WO-2018187493 A1 | 10/2018 |
| WO | WO-2019018426 A1 | 1/2019 |
| WO | WO-2019018428 A1 | 1/2019 |
| WO | WO-2019079215 A1 | 4/2019 |
| WO | WO-2019152806 A1 | 8/2019 |
| WO | WO-2019152808 A1 | 8/2019 |
| WO | WO-2020047344 A1 | 3/2020 |
| WO | WO-2020047353 A1 | 3/2020 |
| WO | WO-2020128146 A1 | 6/2020 |
| WO | WO-2021042060 A1 | 3/2021 |

OTHER PUBLICATIONS

Faber et al (Cancer Cell, 2008, vol. 13, pp. 467-469) (Year: 2008).*
Curti et al (Cancer Research, 2013, vol. 73, pp. 7189-7198) (Year: 2013).*
Pardoll (Nature Reviews Cancer, 2012, vol. 12, pp. 252-264). (Year: 2012).*
Das et al (Nucleic Acid Therapeutics, Mar. 2019, vol. 29, pp. 61-66). (Year: 2019).*
Chen et al (Journal of Experimental & Clinical Cancer Research, 2010, vol. 29, 10 pages) (Year: 2010).*
Shi et al (Journal of Cellular Biochemistry, 2012, vol. 114, pp. 1890-1900) (Year: 2012).*
Lee et al (American Journal of Clinical Oncology, 2016, vol. 39, pp. 609-613). (Year: 2016).*
Galluzzi et al (Oncolmmunology, 2012, vol. 1, pp. 1-18) (Year: 2012).*
Poeck et al (Nature Medicine, 2008, vol. 14, pp. 1256-1263) (Year: 2008).*
Elion and Cook (Oncotarget, 2018, vol. 9, pp. 29007-29017). (Year: 2018).*
Mehrotra et al (Journal of Hematology & Oncology, 2017, vol. 10, (Year: 2017).*
Ahmed, N., et al., "Immunotherapy for osteosarcoma: genetic modification of T cells overcomes low levels of tumor antigen expression," Mol. Ther. 17:1779-1787, Cell Press, United States (2009).
Ahmed, N., et al., "HER2-specific T cells target primary glioblastoma stem cells and induce regression of autologous experimental tumors," Clin. Cancer Res. 16:474-485, American Association for Cancer Research, United States (2010).
Altenschmidt, U., et al., "Cytolysis of tumor cells expressing the Neu/erbB-2, erbB-3, and erbB-4 receptors by genetically targeted naive T lymphocytes," Clin. Cancer Res. 2:1001-1008, American Association for Cancer Research, United States (1996).
Ansell, S.M., et al., "PD-1 blockade with nivolumab in relapsed or refractory Hodgkin's lymphoma," The New England Journal of Medicine 372:311-319, Massachusetts Medical Society, United States (2015).
Azuma, T., et al., "B7-H1 is a ubiquitous antiapoptotic receptor on cancer cells," Blood 111:3635-3642, American Society of Hematology, United States (2008).
Baldwin, S.A., et al., "The equilibrative nucleoside transporter family, SLC29," Pflugers Arch. 447(5):753-743, Springer Verlag, Germany (2004).
Barber, A., et al., "Chimeric NKG2D receptor-expressing T cells as an immunotherapy for multiple myeloma," Exp. Hematol. 36:1318-1328, Elsevier, Netherlands (2008).
Barrett, D.M., et al., "Chimeric antigen receptor therapy for cancer," Annu. Rev. Med. 65:333-347, Annual Reviews, United States (2014).
Berger, C., et al., "Adoptive transfer of effector CD8+ T cells derived from central memory cells establishes persistent T cell memory in primates," J. Clin. Invest 118:294-305, American Society for Clinical Investigation, United States (2008).
Bernstein, E., et al., "Role for a bidentate ribonuclease in the initiation step of RNA interference," Nature 409:363-369, Nature Portfolio, Germany (2001).
Bodera, P., "Immunostimulatory oligonucleotides," Recent Pat. Inflamm. Allergy Drug Discov. 5:87-93, Bentham Science Publishers B.V, United Arab Emirates (2011).
Braasch, D. A., and Corey, D. R., "Locked nucleic acid (LNA): fine-tuning the recognition of DNA and RNA," Chem Biol 8(1):1-7, Cell Press, United States (Jan. 2001).
Brahmer, J.R., et al., "Phase I study of single-agent anti-programmed death-1 (MDX-1106) in refractory solid tumors: safety, clinical activity, pharmacodynamics, and immunologic correlates," J. Clin. Oncol. 28:3167-3175, American Society of Clinical Oncology, United States (2010).
Brentjens, R.J., "Cellular therapies in acute lymphoblastic leukemia," Curr. Opin. Mol Ther. 11(4):375-382, Elsevier, Netherlands (2009).

(56) References Cited

OTHER PUBLICATIONS

Brentjens, R.J., et al., "CD19-targeted T cells rapidly induce molecular remissions in adults with chemotherapy-refractory acute lymphoblastic leukemia," Sci. Transl. Med. 5:177ra38, American Association for the Advancement of Science, United States (2013).
Brentjens, R.J., et al., "Eradication of systemic B-cell tumors by genetically targeted human T lymphocytes co-stimulated by CD80 and interleukin-15," Nat. Med. 9:279-286, Nature Portfolio, Germany (2003).
Brentjens, R.J., et al., "Safety and persistence of adoptively transferred autologous CD19-targeted T cells in patients with relapsed or chemotherapy refractory B-cell leukemias," Blood 118:4817-4828, American Society of Hematology, United States (2011).
Brown, C.E., et al., "Stem-like tumor-initiating cells isolated from IL13Rα2 expressing gliomas are targeted and killed by IL13-zetakine-redirected T Cells," Clin Cancer Res 18(8):2199-2209, American Association for Cancer Research, United States (2012).
Bullain, S.S., et al. "Genetically engineered T cells to target EGFRvIII expressing glioblastoma," J. Neurooncol. 94(3):373-382, Springer, Germany (2009).
Burns, W.R., et al., "A high molecular weight melanoma-associated antigen-specific chimeric antigen receptor redirects lymphocytes to target human melanomas," Cancer Res 70:3027-3033, American Association for Cancer Research, United States (2010).
Butte, M.J., et al., "Programmed death-1 ligand 1 interacts specifically with the B7-1 costimulatory molecule to inhibit T cell responses," Immunity 27:111-122, Cell Press, United States (2007).
Carreno, B.M., et al., "The B7 family of ligands and its receptors: new pathways for costimulation and inhibition of immune responses," Annu. Rev. Immunol. 20:29-53, Annual Reviews, United States (2002).
Cartellieri, M., et al., "Chimeric antigen receptor-engineered T cells for immunotherapy of cancer," J. Biomed. Biotechnol. 2010:956304, Hindawi, United Kingdom (2010).
Cermak, T., et al., "Efficient design and assembly of custom TALEN and other TAL effector-based constructs for DNA targeting," Nucleic Acids Res 39(12):e82, 11 pages, Oxford University Press, United Kingdom (Jul. 2011).
Charo, J., et al., "Bcl-2 overexpression enhances tumor-specific T-cell survival," Cancer Res. 65(5):2001-2008, American Association for Cancer Research, United States (2005).
Cheever, M.A., et al., "The prioritization of cancer antigens: a national cancer institute pilot project for the acceleration of translational research," Clin Cancer Res. 15:5323-5337, American Association for Cancer Research, United States (2009).
Chen, L., "Co-inhibitory molecules of the B7-CD28 family in the control of T-cell immunity," Nat. Rev. Immunol. 4:336-347, Nature Portfolio, Germany (2004).
Chen, L., et al., "Anti-PD-1/PD-L1 therapy of human cancer: past, present, and future," J. Clin. Invest. 125:3384-3391, American Society for Clinical Investigation, United States (2015).
Chen, Z., et al., "A lupus anti-DNA autoantibody mediates autocatalytic, targeted delivery of nanoparticles to tumors," Oncotarget. 7(37):59965-59975, Impact Journals, United States (2016).
Cheung, N.K., et al., "Anti-idiotypic antibody facilitates scFv chimeric immune receptor gene transduction and clonal expansion of human lymphocytes for tumor therapy," Hybrid Hybridomics 22:209-218, Mary Ann Liebert, Inc., United States (2003).
Chinnasamy, D., et al., "Gene therapy using genetically modified lymphocytes targeting VEGFR-2 inhibits the growth of vascularized syngenic tumors in mice," J. Clin. Invest. 120:3953-3968, American Society for Clinical Investigation, United States (2010).
Chmielewski, M., et al., "T cell activation by antibody-like immunoreceptors: increase in affinity of the single-chain fragment domain above threshold does not increase T cell activation against antigen-positive target cells but decreases selectivity," J. Immunol. 173:7647-7653, American Association of Immunologists, United States (2004).
Chothia, C., and Lesk, A. M., "Canonical structures for the hypervariable regions of immunoglobulins," J Mol Biol 196(4):901-917, Elsevier Science, United States (Aug. 1987).
Chow, K.M., et al., "T cells redirected to EphA2 for the immunotherapy of glioblastoma," Mol. Ther. 21:629-637, Cell Press, United States (2013).
Cong, L., "Multiplex genome engineering using CRISPR/Cas systems," Science 339(6121):819-823, American Association for the Advancement of Science, United States (Feb. 2013).
Cooper, L., et al., "Enhanced antilymphoma efficacy of CD19-redirected influenza MP1- specific CTLs by cotransfer of T cells modified to present influenza MP1," Blood 105:1622-1631, American Society of Hematology, United States (2005).
Cougot, N., et al., "'Cap-tabolism'," Trends. Biochem. Sci. 29:436-444, Elsevier, Netherlands (2001).
Crawford, C.R., et al., "Cloning of the human equilibrative, nitrobenzylmercaptopurine riboside (NBMPR)-insensitive nucleoside transporter ei by functional expression in a transport-deficient cell line," J. Biol. Chem. 273(9):5288-5293, American Society for Biochemistry and Molecular Biology, United States (1998).
Curran, K.J., et al., "Chimeric antigen receptors for T cell immunotherapy: current understanding and future directions," J. Gene. Med. 14:405-415, John Wiley & Sons, United States (2012).
Dall, P., et al., "In vivo cervical cancer growth inhibition by genetically engineered cytotoxic T cells," Cancer Immunol. Immunother. 54:51-60, Springer Science+Business Media, Germany (2005).
Dalpke, A.H., et al., "Phosphodiester CpG oligonucleotides as adjuvants: polyguanosine runs enhance cellular uptake and improve immunostimulative activity of phosphodiester CpG oligonucleotides in vitro and in vivo," Immunology. 106:102-112, John Wiley & Sons Ltd., United States (2002).
Daly, T., et al., "Recognition of human colon cancer by T cells transduced with a chimeric receptor gene," Cancer Gene Ther. 7:284-291, Springer Nature, United Kingdom (2000).
Danial, N.N., et al., "Cell death: critical control points," Cell 116:205-219, Cell Press, United States (2004).
Davies, D.M., et al., "Flexible targeting of ErbB dimers that drive tumorigenesis by using genetically engineered T cells," Mol Med. 18:565-576, The Feinstein Institutes for Medical Research, United States (2012).
Desai, M. P., et al., "The mechanism of uptake of biodegradable microparticles in Caco-2 cells is size dependent," Pharm Res 14(11):1568-1573, Springer Science+Business Media, Germany (Nov. 1997).
Di Stasi. A., et al., "T lymphocytes coexpressing CCR4 and a chimeric antigen receptor targeting CD30 have improved homing and antitumor activity in a Hodgkin tumor model" Blood 113:6392-6402, American Society of Hematology, United States (2009).
Dong, H., et al., "B7-H1 determines accumulation and deletion of intrahepatic CD8(+) T lymphocytes," Immunity 20:327-336, Cell Press, United States (2004).
Dotti, G., "The other face of chimeric antigen receptors," Mol. Ther. 22(5):899-890, Cell Press, United States (2014).
Dotti, G., et al., "Design and development of therapies using chimeric antigen receptor-expressing T cells," Immunol. Rev.257:107-126, John Wiley & Sons Ltd, United States (2014).
Eaton, D., et al., "Retroviral transduction of human peripheral blood lymphocytes with Bcl-X(L) promotes in vitro lymphocyte survival in pro-apoptotic conditions," Gene Therapy 9:527-535, Springer Nature, United Kingdom (2002).
Elango, N., et al., "Optimized transfection of mRNA transcribed from a d(A/T)100 tail-containing vector," Biochem. Biophys. Res. Commun. 330:958-966, Elsevier, Netherlands (2005).
Elbashir, S.M., et al., "Duplexes of 21-nucleotide RNAs mediate RNA interference in cultured mammalian cells," Nature 411:494-498, Nature Portfolio, Germany (2001).
Elbashir, S.M., et al., "RNA interference is mediated by 21- and 22-nucleotide RNAs,"Genes Dev. 15:188-200, Cold Spring Harbor Laboratory Press, United States (2001).
Federov, V.D., et al., "PD-1- and CTLA-4-based inhibitory chimeric antigen receptors (iCARs) divert off-target immunotherapy responses," Science Translational Medicine 5:215ra172, American Association for the Advancement of Science, United States (2013).

(56) References Cited

OTHER PUBLICATIONS

Finney, H.M., et al., "Chimeric receptors providing both primary and costimulatory signaling in T cells from a single gene product," J. Immunol. 161:2791-2797, American Association of Immunologists, United States (1998).
Fire, A., et al., "Potent and specific genetic interference by double-stranded RNA in Caenorhabditis elegans ," Nature 391:806-811, Nature Portfolio, Germany (1998).
Flies, D.B., et al., "The new B7s: playing a pivotal role in tumor immunity," J. Immunotherapy 30:251-260, Lippincott Williams and Wilkins Ltd., United States (2007).
Gattenlohner, S., et al., "Rhabdomyosarcoma lysis by T cells expressing a human autoantibody-based chimeric receptor targeting the fetal acetylcholine receptor," Cancer Res. 66:24-28, American Association for Cancer Research, United States (2006).
Gattinoni, L., et al., "A human memory T cell subset with stem cell-like properties," Nat. Med. 17:1290-1297, Nature Portfolio, Germany (2011).
Genbank, "immunoglobulin heavy chain, partial [Mus musculus]," ncbi.nlm.nih.gov, Accession No. AAA65679.1, accessed at URL:[https://www.ncbi.nlm.nih.gov/protein/AAA65679] on Jan. 14, 2022, 1 page.
Genbank, "immunoglobulin light chain, partial [Mus musculus]," ncbi.nlm.nih.gov, Accession No. AAA65681.1, accessed at URL:[https://www.ncbi.nlm.nih.gov/protein/AAA65681] on Jan. 14, 2022, 1 page.
Genbank, "Mouse Ig rearranged H-chain gene, partial cds," ncbi.nlm.nih.gov, Accession No. L16982.1, accessed at URL:[https://www.ncbi.nlm.nih.gov/nuccore/L16982] on Jan. 14, 2022, 1 page.
Genbank, "Mouse Ig rearranged L-chain gene, partial cds," ncbi.nlm.nih.gov, Accession No. L16981.1, accessed at URL:[https://www.ncbi.nlm.nih.gov/nuccore/L16981] on Jan. 14, 2022, 1 page.
Gilham, D.E., et al., "Primary polyclonal human T lymphocytes targeted to carcino-embryonic antigens and neural cell adhesion molecule tumor antigens by CD3zeta-based chimeric immune receptors," J. Immunother. 25:139-151, Lippincott Williams and Wilkins Ltd., United States (2002).
Gong, M.C., et al., "Cancer patient T cells genetically targeted to prostate-specific membrane antigen specifically lyse prostate cancer cells and release cytokines in response to prostate-specific membrane antigen," Neoplasia 1:123-127, Elsevier, Netherlands (1999).
Govindarajan, R., et al., "In situ hybridization and immunolocalization of concentrative and equilibrative nucleoside transporters in the human intestine, liver, kidneys, and placenta," Am. J. Physiol. Regul. Integr. Comp. Physiol. 293(5): R1809-1822, American Physiological Society, United States (2007).
Grada, Z., et al., "TanCAR: A Novel Bispecific Chimeric Antigen Receptor for Cancer Immunotherapy," Mol. Ther. Nucleic Acids 2:e105, Elsevier, Netherlands (2013).
Greenwald, R.J., et al., "The B7 family revisited," Annu. Rev. Immunol. 23:515-548, Annual Reviews, United States (2005).
Griffiths, M., et al., "Molecular cloning and characterization of a nitrobenzylthioinosine-insensitive (ei) equilibrative nucleoside transporter from human placenta," Biochem. J. 328(3):739-743, Portland Press, United Kingdom (1997).
Grupp, S.A., et al., "Chimeric antigen receptor-modified T cells for acute lymphoid leukemia," N. Engl. J. Med 368(16):1509-1518, Massachusetts Medical Society, United States (2013).
Hamid, O., et al., "A prospective phase II trial exploring the association between tumor microenvironment biomarkers and clinical activity of ipilimumab in advanced melanoma," J. Transl. Med. 9:204, BioMed Central, United Kingdom (2011).
Hammond, S.M., et al., "An RNA-directed nuclease mediates post-transcriptional gene silencing in Drosophila cells," Nature 404:293-296, Nature Portfolio, Germany (2000).
Hanna, J., et al., "Treatment of sickle cell anemia mouse model with iPS cells generated from autologous skin," Science 318(5858):1920-1923, American Association for the Advancement of Science, United States (Dec. 2007).
Hannon, G.J., "RNA interference," Nature 418:244-251, Nature Portfolio, Germany (2002).
Hansen, J.E., et al., "Antibody-Mediated p53 Protein Therapy Prevents Liver Metastasis In vivo," Cancer Res. 67(4): 1769-1774, American Association for Cancer Research, United States (2007).
Hansen, J.E., et al., "Targeting cancer with a lupus autoantibody," Sci. Transl. Med. 4(157):157, American Association for the Advancement of Science, United States (2012).
Hansen, J.E., et al., "Antibody-mediated Hsp70 protein therapy," Brain. Res. 1088:187-196, Elsevier, Netherlands (2006).
Hansen, J.E., et al., "Intranuclear protein transduction through a nucleoside salvage pathway," J. Biol. Chem. 282(29):20790-20793, American Society for Biochemistry and Molecular Biology, United States (2007).
Hartmann, G., et al., "Delineation of a CpG phosphorothioate oligodeoxynucleotide for activating primate immune responses in vitro and in vivo," J. Immunol. 164(3):1617-1620, American Association of Immunologists, United States (2000).
Haso, W., et al., "Anti-CD22-chimeric antigen receptors targeting B-cell precursor acute lymphoblastic leukemia," Blood 121:1165-1174, American Society of Hematology, United States (2013).
Haynes, N.M., et al., "Redirecting mouse CTL against colon carcinoma: superior signaling efficacy of single-chain variable domain chimeras containing TCR-zeta vs Fc epsilon RI-gamma," J. Immunol. 166:182-187, American Association of Immunologists, United States (2001).
Heemskerk, B., et al., "Adoptive cell therapy for patients with melanoma, using tumor- infiltrating lymphocytes genetically engineered to secrete interleukin-2," Human Gene Therapy 19:496-510, Mary Ann Liebert, Inc., United States (2008).
Hekele, A., et al., "Growth retardation of tumors by adoptive transfer of cytotoxic T lymphocytes reprogrammed by CD44v6-specific scFv:zeta-chimera," Int. J. Cancer 68:232-238, Wiley, United States (1996).
Herrmann, A., et al.," An effective cell-penetrating antibody delivery platform," JCI Insight, 4(14):e127474, American Society for Clinical Investigation, United States (2019).
Hombach, A., et al., "T cell activation by recombinant FcepsilonRI gamma-chain immune receptors: an extracellular spacer domain impairs antigen-dependent T cell activation but not antigen recognition," Gene Ther. 7:1067-1075, Nature Publishing Group, United Kingdom (2000).
Hombach, A., et al., "An anti-CD30 chimeric receptor that mediates CD3-zeta-independent T-cell activation against Hodgkin's lymphoma cells in the presence of soluble CD30," Cancer. Res. 58:1116-1119, American Association for Cancer Research, United States (1998).
Hombach, A., et al., "T cell targeting of TAG72+ tumor cells by a chimeric receptor with antibody-like specificity for a carbohydrate epitope," Gastroenterology 113:1163-1170, Elsevier, Netherlands (1997).
Huang, A., et al., "Functional silencing of hepatic microsomal glucose-6-phosphatase gene expression in vivo by adenovirus-mediated delivery of short hairpin RNA," FEBS Lett 558(1-3):69-73, Wiley on behalf of FEBS, United States (Jan. 2004).
Huang, G., et al., "Genetically modified T cells targeting interleukin-11 receptor α-chain kill human osteosarcoma cells and induce the regression of established osteosarcoma lung metastases," Cancer Res. 72:271-281, American Association for Cancer Research, United States (2012).
Hudecek, M., et al., "Receptor Affinity Extracellular Domain Modifications Affect Tumor Recognition by ROR1-Specific Chimeric Antigen Receptor T Cells," Clin Cancer Res. 19(12):3153-3164, American Association for Cancer Research, United States (2013).
Hunter, M.R., et al., "Chimeric γc cytokine receptors confer cytokine independent engraftment of human T lymphocytes," Mol. Immunol. 56:1-11, Pergamon Press, United Kingdom (2013).
Hwu, P., et al., "In vivo antitumor activity of T cells redirected with chimeric antibody/T-cell receptor genes," Cancer Res. 55:3369-3373, American Association for Cancer Research, United States (1995).

(56) References Cited

OTHER PUBLICATIONS

International Search Report and Written Opinion for International Application No. PCT/US2020/048823, dated Oct. 19, 2020, European Patent Office, Germany, 14 pages.
Irving, B.A., et al., "The cytoplasmic domain of the T cell receptor zeta chain is sufficient to couple to receptor-associated signal transduction pathways," Cell 64:891-901, Cell Press, United States (1991).
Jensen, M., et al., "CD20 is a molecular target for scFvFc:zeta receptor redirected T cells: implications for cellular immunotherapy of CD20+ malignancy," Blood Bone Marrow Transplant 4:75-83, Elsevier, Netherlands (1998).
Jensen, M.C., et al., "Antitransgene rejection responses contribute to attenuated persistence of adoptively transferred CD20/CD19-specific chimeric antigen receptor redirected T cells in humans," Biol. Blood Marrow Transplant 16(9):1245-1256, Elsevier, Netherlands (2010).
Jensen, M.C., et al., "Design and implementation of adoptive therapy with chimeric antigen receptor-modified T cells," Immunol Rev. 257:127-144, John Wiley & Sons Ltd, United States (2014).
Jinek, M., et al., "A programmable dual-RNA-guided DNA endonuclease in adaptive bacterial immunity," Science 337(6096):816-821, American Association for the Advancement of Science, United States (Aug. 2012).
Kabat, E.A. et al., "Sequences of proteins of immunological interest," U.S. Dept. of Health and Human Services, United States (1991).
Kahlon, K.S., et al., "Specific recognition and killing of glioblastoma multiforme by interleukin 13-zetakine redirected cytolytic T cells," Cancer Res. 64(24):9160-9166, American Association for Cancer Research, United States (2004).
Kakarla, S., et al., "Antitumor effects of chimeric receptor engineered human T cells directed to tumor stroma," Mol. Ther. 21(8):1611-1620, Cell Press, United States (2013).
Kalos, M., et al., "T cells with chimeric antigen receptors have potent antitumor effects and can establish memory in patients with advanced leukemia," Sci. Transl. Med. 3:95ra73, American Association for the Advancement of Science, United States (2011).
Karlsson, H., et al., "Combining Car T cells and the Bcl-2 family apoptosis inhibitor ABT-737 for treating B-cell malignancy," Cancer Gene Therapy 20:386-393, Springer Nature, United Kingdom (2013).
Katari, U.L., et al., "Engineered T cells for pancreatic cancer treatment," HPB 13:643-650, John Wiley & Sons Inc., United Kingdom (2011).
Keir, M.E., et al., "PD-1 and its ligands in tolerance and immunity," Annu. Rev. Immunol. 26:677-704, Annual Reviews, United States (2008).
Kershaw, M.H., et al., "A phase I study on adoptive immunotherapy using gene-modified T cells for ovarian cancer," Clin. Cancer Res. 12:6106-6115, American Association for Cancer Research, United States (2006).
Kershaw, M.H., et al., "Dual-specific T cells combine proliferation and antitumor activity," Nat. Biotechnol. 20:1221-1227, Springer Nature Ltd., Germany (2002).
Kim, Y-G., and Chandrasegaran, S., "Chimeric restriction endonuclease," Proc. Natl. Acad. Sci. USA 91(3):883-887, National Academy of Sciences, United States (Feb. 1994).
Kim, Y-G., et al., "Insertion and deletion mutants of FokI restriction endonuclease," J. Biol. Chem. 269(50):31978-31982, Elsevier, Netherlands (Dec. 1994).
Kochenderfer, J.N., et al., "B-cell depletion and remissions of malignancy along with cytokine-associated toxicity in a clinical trial of anti-CD19 chimeric-antigen-receptor-transduced T cells," Blood 119:2709-2720, American Society of Hematology, United States (2012).
Kong, S., et al., "Suppression of human glioma xenografts with second-generation IL13R-specific chimeric antigen receptor-modified T cells," Clin Cancer Res 18:5949-5969, American Association for Cancer Research, United States (2012).
Kuwana, Y., et al., "Expression of chimeric receptor composed of immunoglobulin-derived V regions and T-cell receptor-derived C regions," Biochem. Piophys. Res. Commun. 149:960-968, Elsevier, Netherlands (1987).
Lamers, C.H., et al., "Treatment of metastatic renal cell carcinoma with autologous T-lymphocytes genetically retargeted against carbonic anhydrase IX: first clinical experience," J. Clin. Oncol. 24(13):e20-e22, American Society of Clinical Oncology, United States (2006).
Lanitis, E., et al., "Redirected antitumor activity of primary human lymphocytes transduced with a fully human anti-mesothelin chimeric receptor," Mol. Ther. 20:633-643, Cell Press, United States (2012).
Larkin, J., et al., "Combined Nivolumab and Ipilimumab or Monotherapy in Untreated Melanoma," The New England Journal of Medicine 373:311-319, Massachusetts Medical Society, United States (2015).
Larson, M.H., et al., "CRISPR interference (CRISPRi) for sequence-specific control of gene expression, " Nat. Protoc. 8:2180-2196, Nature Portfolio, Germany (2013).
Lehner, M., et al., "Redirecting T cells to Ewing's sarcoma family of tumors by a chimeric NKG2D receptor expressed by lentiviral transduction or mRNA transfection," PLOS One 7:e31210, PLOS, United States (2012).
Li, L., and Chandrasegaran, S., "Alteration of the cleavage distance of Fok I restriction endonuclease by insertion mutagenesis," Proc. Natl. Acad. Sci. USA 90(7):2764-2768, National Academy of Sciences, United States (Apr. 1993).
Li, L., et al., "Functional domains in Fok I restriction endonuclease," Proc. Natl. Acad. Sci. USA 89(10):4275-4279, National Academy of Sciences, United States (May 1992).
Lorenz, C., et al., "Steroid and lipid conjugates of siRNAs to enhance cellular uptake and gene silencing in liver cells," Bioorg. Med. Chem. Lett. 14(19):4975-4977, Elsevier, Netherlands (Oct. 2004).
Louis, C.U., et al., "Antitumor activity and long-term fate of chimeric antigen receptor-positive T cells in patients with neuroblastoma," Blood 118:6050-6056, American Society of Hematology, United States (2011).
Luens, K. M., et al., "Thrombopoietin, kit ligand, and flk2/flt3 ligand together induce increased numbers of primitive hematopoietic progenitors from human CD34+Thy-1+Lin– cells with preserved ability to engraft SCID-hu bone," Blood 91(4):1206-1215, Elsevier, Netherlands (Feb. 1998).
Ma, M. Y., et al., "Nuclease-resistant external guide sequence-induced cleavage of target RNA by human ribonuclease P," Antisense Nucleic Acid Drug Dev. 8(5):415-426, Mary Ann Liebert, Inc., United States (Oct. 1998).
Maher, J., "Immunotherapy of malignant disease using chimeric antigen receptor engrafted T cells," ISRN Oncol. 2012:278093, Hindawi, United Kingdom (2012).
Maher, J., et al., "Human T-lymphocyte cytotoxicity and proliferation directed by a single chimeric TCRzeta /CD28 receptor," Nat. Biotech. 20:70-75, Springer Nature Ltd., Germany (2002).
Martinez, J., et al., "Single-stranded antisense siRNAs guide target RNA cleavage in RNAi," Cell. 110:563-574, Cell Press, United States (2002).
McGuinness, R.P., et al., "Anti-tumor activity of human T cells expressing the CC49-zeta chimeric immune receptor," Hum. Gene Ther. 10:165-173, Mary Ann Liebert, Inc., United States (1999).
Meazza, R., et al., "Role of common-gamma chain cytokines in NK cell development and function: perspectives for immunotherapy," J. Biomed. & Biotechnol. 2011:861920, Hindawi, United Kingdom (2011).
Meier, R., et al., "Depicting adoptive immunotherapy for prostate cancer in an animal model with magnetic resonance imaging." Magn. Reson. Med. 65:756-763, Wiley, United States (2011).
Mezzanzanica, D., et al., "Transfer of chimeric receptor gene made of variable regions of tumor-specific antibody confers anticarbohydrate specificity on T cells," Cancer Gene Ther. 5:401-407, Springer Nature Ltd., Germany (1998).

(56) References Cited

OTHER PUBLICATIONS

Michaud, A., et al., "IL-7 enhances survival of human CD56bright NK cells," J. Immunotherapy 33:382-390, Lippincott Williams and Wilkins Ltd , United States (2010).
Miller, J. C., et al., "A Tale nuclease architecture for efficient genome editing," Nat. Biotechnol. 29(2): 143-148, Nature Publishing Group, United Kingdom (Feb. 2011).
Moon, E.K., et al., "Expression of a functional CCR2 receptor enhances tumor localization and tumor eradication by retargeted human T cells expressing a mesothelin-specific chimeric antibody receptor," Clin. Cancer Res. 17:4719-4730, American Association for Cancer Research, United States (2011).
Morgan, R.A., et al., "Case report of a serious adverse event following the administration of T cells transduced with a chimeric antigen receptor recognizing ERBB2," Mol. Ther. 18:843-851, Cell Press, United States (2010).
Morgan, R.A., et al., "Recognition of glioma stem cells by genetically modified T cells targeting EGFRvIII and development of adoptive cell therapy for glioma," Hum. Gene Ther. 23:1043-1053, Mary Ann Liebert, Inc., United States (2012).
Morgenroth, A., et al., "Targeting of tumor cells expressing the prostate stem cell antigen (PSCA) using genetically engineered T-cells," Prostate 67:1121-1131, Wiley, United States (2007).
Moritz, D., et al., "Cytotoxic T lymphocytes with a grafted recognition specificity for ERBB2-expressing tumor cells," Proc. Natl. Acad. Sci. USA 91:4318-4322, National Academy of Sciences, United States (1994).
Muniappan, A., et al., "Ligand-mediated cytolysis of tumor cells: use of heregulin-zeta chimeras to redirect cytotoxic T lymphocytes," Cancer Gene Ther. 7:128-134, Springer, Germany (2000).
Nakamura, Y., et al., "Codon usage tabulated from international DNA sequence databases: status for the year 2000," Nucl. Acids Res. 28:292, Oxford University Press, United Kingdom (2000).
Napoli, C., et al., "Introduction of a Chimeric Chalcone Synthase Gene into Petunia Results in Reversible Co-Suppression of Homologous Genes in trans," Plant Cell 2:279-289, American Society of Plant Biologists, United States (1990).
Niederman, T.J., et al., "Antitumor activity of cytotoxic T lymphocytes engineered to target vascular endothelial growth factor receptors," Proc. Natl. Acad. Sci. USA 99:7009-7014, National Academy of Sciences, United States (2002).
Nishimura, H., et al., "Development of lupus-like autoimmune diseases by disruption of the PD-1 gene encoding an ITIM motif-carrying immunoreceptor," Immunity 11:141-151, Cell Press, United States (1999).
Noble, P. W., et al., "Optimizing a lupus autoantibody for targeted cancer therapy," Cancer Res 75(11):2285-2291, American Association for Cancer Research, United States (Jun. 2015).
Nolan, K.F., et al., "Bypassing immunization: optimized design of "designer T cells" against carcinoembryonic antigen (CEA)-expressing tumors, and lack of suppression by soluble CEA," Clin. Cancer Res. 5:3928-3941, American Association for Cancer Research, United States (1999).
Nyce, J. W., and Metzger, W. J., "DNA antisense therapy for asthma in an animal model," Nature 385(6618):721-725, Nature Publishing Group, United Kingdom (Feb. 1997).
Nykanen, A., et al., "ATP requirements and small interfering RNA structure in the RNA interference pathway," Cell 107:309-321, Cell Press, United States (2001).
Oltersdorf, T., et al., "An inhibitor of Bcl-2 family proteins induces regression of solid tumours," Nature 435:677-681, Nature Portfolio, Germany (2005).
Opferman, J.T., et al., "Development and maintenance of B and T lymphocytes requires antiapoptotic MCL-1," Nature 426:671-676, Springer Nature Ltd., Germany (2003).
Park, J.J., et al., "B7-H1/CD80 interaction is required for the induction and maintenance of peripheral T-cell tolerance," Blood 116:1291-1298, American Society of Hematology, United States (2010).
Park, J.R., et al., "Adoptive transfer of chimeric antigen receptor re-directed cytolytic T lymphocyte clones in patients with neuroblastoma," Mol. Ther. 15:825-833, Cell Press, United States (2007).
Paulos, C.M., et al., "The inducible costimulator (ICOS) is critical for the development of human T(H)17 cells," Sci. Transl. Med. 2:55-78, American Association for the Advancement of Science, United States (2010).
Peinert, S., et al., "Gene-modified T cells as immunotherapy for multiple myeloma and acute myeloid leukemia expressing the Lewis Y antigen," Gene Ther. 17:678-686, Springer Nature Ltd., Germany (2010).
Pentcheva-Hoang, T., et al., "Negative regulators of T-cell activation: potential targets for therapeutic intervention in cancer, autoimmune disease, and persistent infections," Immunological Reviews 229:67-87, Nature Portfolio, Germany (2009).
Pfeiffer, A., et al., "In vivo generation of human CD19-CAR T cells results in B-cell depletion and signs of cytokine release syndrome," EMBO Mol. Med. 10(11):e9158, European Molecular Biology Organization, Germany (2018).
Pinthus, J.H., et al., "Adoptive immunotherapy of prostate cancer bone lesions using redirected effector lymphocytes," J. Clin. Invest. 114:1774-1781, American Society for Clinical Investigation, United States (2004).
Porter, D.L., et al., "Chimeric antigen receptor-modified T cells in chronic lymphoid leukemia," N. Engl. J. Med. 365:725-733, Massachusetts Medical Society, United States (2011).
Pule, M.A., et al., "Virus-specific T cells engineered to coexpress tumor-specific receptors: persistence and antitumor activity in individuals with neuroblastoma," Nat. Med. 14:1264-1270, Springer Nature Ltd., Germany (2008).
Ramirez-Ortiz, Z., et al., "Toll-like receptor 9-dependent immune activation by unmethylated CpG motifs in Aspergillus fumigatus DNA" Infec. Immun. 76(5):2123-2129, American Society for Microbiology, United States (2008).
Ramos, C.A., et al., "Chimeric antigen receptor (CAR)-engineered lymphocytes for cancer therapy," Expert Opin. Biol. Ther. 11(7):855-873, Taylor & Francis, United Kingdom (2011).
Rattray, Z., et al., "Re-engineering and evaluation of anti-DNA autoantibody 3E10 for therapeutic applications," Biochem Biophys Res Commun 496(3):858-864, Elsevier, Netherlands (Jan. 2018).
Rein-Heidenreich, L.R., et al., "Comparison of the TCR zeta-chain with the FcR gamma-chain in chimeric TCR constructs for T cell activation and apoptosis," Cancer Immunol. Immunother. 51:417-423, Springer Science+Business Media, Germany (2002).
Ribas, A., et al., "Dendritic cell vaccination combined with CTLA4 blockade in patients with metastatic melanoma," Clinical Cancer Research 15:6267-6276, American Association for Cancer Research, United States (2009).
Ricciardi, A. S., et al., "In utero nanoparticle delivery for site-specific genome editing," Nat Commun 9(1):2481, Nature Publishing Group, United Kingdom (Jun. 2018).
Ritchie, D.S., et al., "Persistence and efficacy of second generation CAR T cell against the LeY antigen in acute myeloid leukemia," Mol. Ther. 21(11):2122-2129, Cell Press, United States (2013).
Robbins, R., "Gene therapy pioneer says the field is behind—and that delivery technology is embarrassing," StatNews.com, Nov. 2019, accessed at https://www.statnews.com/2019/11/21/gene-therapy-pioneer-says-the-field-is-behind-and-that- delivery-technology-is-embarrassing/, 3 pages.
Robert, C., et al., "Nivolumab in previously untreated melanoma without BRAF mutation,"The New England Journal of Medicine 372:320-330, Massachusetts Medical Society, United States (2015).
Rosenberg, S.A., et al., "Passive immunotherapy of cancer in animals and man," Adv. Cancer Res. 25:323-388, Wolters Kluwer, Netherlands (1977).
Rossig, C., et al., "Targeting of G(D2)-positive tumor cells by human T lymphocytes engineered to express chimeric T-cell receptor genes," Int. J. Cancer. 94:228-236, Wiley, United States (2001).
Rump, E. T., et al., "Modification of the plasma clearance and liver uptake of steroid ester-conjugated oligodeoxynucleotides by association with (lactosylated) low-density lipoprotein," Biochem Pharmacol 59(11):1407-1416, Elsevier, Netherlands (Jun. 2000).

(56) References Cited

OTHER PUBLICATIONS

Sampson, J.S., et al., "Tumor-specific immunotherapy targeting the EGFRvIII mutation in patients with malignant glioma," Semin Immunol. 20(5):267-275, Academic Press Inc., United States (2008).
Savoldo, B., et al., "CD28 costimulation improves expansion and persistence of chimeric antigen receptor-modified T cells in lymphoma patients," J. Clin. Invest. 121:1822-1826, American Society for Clinical Investigation, United States (2011).
Savoldo, B., et al., "Epstein Barr virus specific cytotoxic T lymphocytes expressing the anti-CD30zeta artificial chimeric T-cell receptor for immunotherapy of Hodgkin disease," Blood 110:2620-2630, American Society of Hematology, United States (2007).
Schuberth, P.C., et al., "Effector memory and central memory NY-ESO-1-specific redirected T cells for treatment of multiple myeloma," Gene Ther. 20:386-395, Springer Nature Ltd., Germany (2013).
Seow, Y., et al., "Biological gene delivery vehicles: beyond viral vectors," Mol. Ther. 17(5):767-777, Cell Press, United States (2009).
Shaffer, D.R., et al., "T cells redirected against CD70 for the immunotherapy of CD70-positive malignancies," Blood 117:4304-4314, American Society of Hematology, United States (2011).
Smith, T.T., et al., "In situ programming of leukaemia-specific T cells using synthetic DNA nanocarriers," Nat. Nanotechnol. 12(8):813-820, Nature Portfolio, Germany (2017).
Song, D.G., et al., "Chimeric NKG2D CAR-expressing T cell-mediated attack of human ovarian cancer is enhanced by histone deacetylase inhibition," Hum. Gene Ther. 24:295-305, Mary Ann Liebert, Inc., United States (2013).
Song, Y.C., et al., "Arginines in the CDR of anti-dsDNA autoantibodies facilitate cell internalization via electrostatic interactions," Eur. J. Immunol. 38:3178-3190, Wiley-VCH, Germany (2008).
Song, E., et al., "Antibody mediated in vivo delivery of small interfering RNAs via cell-surface receptors," Nat. Biotechnol. 23(6):709-717, Nature Publishing Group, United Kingdom (2005).
Soutschek, J., et al., "Therapeutic silencing of an endogenous gene by systemic administration of modified siRNAs," Nature 432(7014):173-178, Nature Publishing Group, United Kingdom (Nov. 2004).
Spear, P., et al., "Chimeric antigen receptor T cells shape myeloid cell function within the tumor microenvironment through IFN-γ and GM-CSF," J. Immunol. 188:6389-6398, American Association of Immunologists, United States (2012).
Spertini, F., et al., "Idiotypic vaccination with a murine anti-dsDNA antibody: phase I study in patients with nonactive systemic lupus erythematosus with nephritis," J. Rheumatol. 26(12):2602-2608, Journal of Rheumatology Publishing Company, Canada (1999).
Spranger, S., et al., "Mechanism of tumor rejection with doublets of CTLA-4, PD-1/PD-L1, or IDO blockade involves restored IL-2 production and proliferation of CD8(+) T cells directly within the tumor microenvironment," J. Immunother. Cancer 2:3, BMJ Publishing Group, United Kingdom (2014).
Stancovski, I., et al., "Targeting of T lymphocytes to Neu/HER2-expressing cells using chimeric single chain Fv receptors," J. Immunol. 151:6577-6582, , United States (1993).
Stepinski, J., et al., "Synthesis and properties of mRNAs containing the novel "anti-reverse" cap analogs 7-methyl(3'-O-methyl)GpppG and 7-methyl (3'-deoxy)GpppG," RNA 7:1468-1495, Cold Spring Harbor Laboratory Press , United States (2001).
Sterchak, E.P., et al., "Uncharged stereoregular nucleic acid analogs. 1. Synthesis of a cytosine-containing oligomer with carbamate internucleoside linkages," J. Organic Chem. 52(19):4202-4206, American Chemical Society, United States (Sep. 1987).
Tamada, K., et al., "Redirecting gene-modified T cells toward various cancer types using tagged antibodies," Clin. Cancer Res. 18:6436-6445, American Association for Cancer Research, United States (2012).
Teng, M.W., et al., "Immunotherapy of cancer using systemically delivered gene-modified human T lymphocytes," Hum. Gene. Ther. 15:699-708, Mary Ann Liebert, Inc., United States (2004).
Tettamanti, S., et al., "Targeting of acute myeloid leukaemia by cytokine-induced killer cells redirected with a novel CD123-specific chimeric antigen receptor," Br. J. Haematol. 161:389-401, Wiley-Blackwell Publishing Ltd, United States (2013).
Till, B.J., et al., "Adoptive immunotherapy for indolent non-Hodgkin lymphoma and mantle cell lymphoma using genetically modified autologous CD20-specific T cells," Blood 112:2261-2271, American Society of Hematology, United States (2008).
Tivol, E.A., et al., "Loss of CTLA-4 leads to massive lymphoproliferation and fatal multiorgan tissue destruction, revealing a critical negative regulatory role of CTLA-4," Immunity 3:541-547 , Cell Press, United States (1995).
Topalian, S.L., et al., "Survival, durable tumor remission, and long-term safety in patients with advanced melanoma receiving nivolumab," J. Clin. Oncol. 32:1020-1030, American Society of Clinical Oncology,, United States (2014).
Topalian, S.L., et al.," Safety, activity, and immune correlates of anti-PD-1 antibody in cancer," New England Journal of Medicine 366:2443-2454, Massachusetts Medical Society, United States (2012).
Turchick, A., et al., "Synthetic lethality of a cell-penetrating anti-RAD51 antibody in PTEN-deficient melanoma and glioma cells," Oncotarget. 10(13):1272-1283, Impact Journals, United Kingdom (2019).
Turchick, A., et al., "A cell-penetrating antibody inhibits human RAD51 via direct binding,"Nucleic Acids Res 45(20):11782-11799, Oxford University Press, United Kingdom (Nov. 2017).
Twyman-Saint Victor, C., et al., "Radiation and dual checkpoint blockade activate non-redundant immune mechanisms in cancer," Nature 520:373-377, Nature Publishing Group, United Kingdom (2015).
Ui-Tei, K., et al., "Sensitive assay of RNA interference in Drosophila and Chinese hamster cultured cells using firefly luciferase gene as target," FEBS Lett. 479:79-82, Wiley, United States (2000).
UniProtKB, "B2CL1_HUMAN," Accession No. Q07817, accessed at https://www.uniprot.org/uniprotkb/Q07817/entry, accessed on Jun. 30, 2022, 17 pages.
UniProtKB, "IL15_HUMAN," Accession No. P40933, accessed at https://www.uniprot.org/uniprotkb/P40933/entry, on Jun. 30, 2022, 6 pages.
UniProtKB, "IL2_HUMAN," Accession No. P60568, accessed at https://www.uniprot.org/uniprotkb/P60568/entry, accessed on Jun. 30, 2022, 9 pages.
UniProtKB, "IL7_HUMAN," Accession No. P13232, accessed at https://www.uniprot.org/uniprotkb/P13232/entry, on Jun. 30, 2022, 6 pages.
UniProtKB, "MCL1_HUMAN," Accession No. Q07820, accessed at https://www.uniprot.org/uniprotkb/Q07820/entry, on Nov. 3, 2022, 12 pages.
Urbanska, K., et al., "A universal strategy for adoptive immunotherapy of cancer through use of a novel T-cell antigen receptor," Cancer Res. 72(7):1844-1852, American Association for Cancer Research, United States (2012).
Vera, J., et al., "T lymphocytes redirected against the kappa light chain of humanimmunoglobulin efficiently kill mature B lymphocyte-derived malignant cells," Blood 108:3890-3897, American Society of Hematology, United States (2006).
Vollmer, J. and Krieg, A.M., "Immunotherapeutic applications of CpG oligodeoxynucleotide TLR9 agonists," Adv. Drug Del. Rev. 61(3):195-204, Elsevier, Netherlands (2009).
Wang, J., et al., "Cellular immunotherapy for follicular lymphoma using genetically modified CD20-specific CD8+ cytotoxic T lymphocytes," Mol. Ther. 9:577-586, Cell Press, United States (2004).
Wang, J., et al., "Optimizing adoptive polyclonal T cell immunotherapy of lymphomas, using a chimeric T cell receptor possessing CD28 and CD137 costimulatory domains," Hum. Gene Ther. 18:712-725, Mary Ann Liebert, Inc., United States (2007).
Wang, S., et al., "Immunobiology of cancer therapies targeting CD137 and B7-H1/PD-1 cosignal pathways," Curr. Top. Microbial Immunol. 344:245-267, Springer, Germany (2011).
Waterhouse, P., et al., "Lymphoproliferative disorders with early lethality in mice deficient in Ctla-4," Science 270:985-988, American Association for the Advancement of Science, United States (1995).

(56) References Cited

OTHER PUBLICATIONS

Weijtens, M.E., et al., "Chimeric scFv/gamma receptor-mediated T-cell lysis of tumor cells is coregulated by adhesion and accessory molecules," Int. J. Canc. 77:181-187, Wiley, United States (1998).
Weiner, G.L., et al., "Immunostimulatory oligodeoxynucleotides containing the CpG motif are effective as immune adjuvants in tumor antigen immunization," PNAS USA 94(20):10833-10837, National Academy of Sciences, United States (1997).
Weisbart, R.H., et al., "An autoantibody is modified for use as a delivery system to target the cell nucleus: therapeutic implications," J. Autoimmun. 11(5):539-546, Elsevier, Netherlands (Oct. 1998).
Weisbart, R.H., et al., "Antibody-mediated transduction of p53 selectively kills cancer cells," Int. J. Oncol. 25(6):1867-1873, Spandidos Publications, Greece (Dec. 2004).
Weisbart, R.H., et al., "DNA-dependent targeting of cell nuclei by a lupus autoantibody," Sci. Rep. 5:12022, Nature Publishing Group, United Kingdom (Jul. 2015).
Weisbart, R.H., et al., "An intracellular delivery vehicle for protein transduction of micro-dystrophin," J. Drug Target 13(2):81-87, Informa, United Kingdom (2005).
Weisbart, R.H., et al., "Novel Protein Transfection of Primary Rat Cortical Neurons Using an Antibody That Penetrates Living Cells," J, Immunol. 164(11):6020-6026, American Association of Immunologists, United States (2000).
Weisbart, R.H., et al., "A conserved anti-DNA antibody idiotype associated with nephritis in murine and human systemic lupus erythematosus," J. Immunol. 144(7):2653-2658, American Association of Immunologists, United States (1990).
Weisbart, R.H., et al., "Nuclear delivery of p53 C-terminal peptides into cancer cells using scFv fragments of a monoclonal antibody that penetrates living cells," Cancer Lett. 195(2):211-219, Elsevier, Netherlands (2003).
Weisbart, R.H., et al., "Beneficial Effects of Oral Immunoglobulin in Rheumatoid Arthritis," J. Clin. Rheumatol. 1(2):135, Lippincott Williams & Wilkins, United States (1995).
Weisbart, R.H., et al., "Cell type specific targeted intracellular delivery into muscle of a monoclonal antibody that minds myosin Iib," Mol. Immunol. 39(13):783-789, Pergamon Press, United Kingdom (2003).
Weisbart, R.H., et al., "A cell-penetrating bispecific antibody for therapeutic regulation of intracellular targets," Mol. Cancer. Ther. 11(10):2169-2173, American Association for Cancer Research Inc., United States (2012).
Weisbart, R.H., et al., "Construction and expression of a bispecific single-chain antibody that penterates mutant p53 colon cancer cells and binds p53," Int. J. Oncol. 25(4):1113-1118, Spandidos Publications, Greece (2004).
Weising, K., et al., "Foreign genes in plants: transfer, structure, expression, and applications," Ann. Rev. Genetics. 22:421, Annual Reviews, United States (1988).
Westwood, J.A., et al., "Adoptive transfer of T cells modified with a humanized chimeric receptor gene inhibits growth of Lewis-Y-expressing tumors in mice," Proc. Natl. Acad. Sci. USA. 102:19051-19056, National Academy of Sciences, United States (2005).
Wherry, E.J., et al., "T cell exhaustion," Nat. Immunol. 12:492-499, Nature Portfolio, Germany (2011).
Wilkie, S., et al., "Retargeting of human T cells to tumor-associated MUC1: the evolution of a chimeric antigen receptor," J. Immunol. 180:4901-4909, American Association of Immunologists, United States (2008).
Willemsen, R.A., et al., "A phage display selected fab fragment with MHC class I-restricted specificity for MAGE-A1 allows for retargeting of primary human T lymphocytes," Gene Ther. 8:1601-1608, Springer Nature Ltd., Germany (2001).
Willemsen, R.A., et al., "T cell retargeting with MHC class I-restricted antibodies: the CD28 costimulatory domain enhances antigen-specific cytotoxicity and cytokine production," J. Immunol. 174:7853-7858, American Association of Immunologists, United States (2005).

Wing, K., et al., "CTLA-4 control over Foxp3+ regulatory T cell function" Science 322:271-275, American Association for the Advancement of Science, United States (2008).
Yaghoubi, S.S., et al., "Noninvasive detection of therapeutic cytolytic T cells with 18F-FHBG PET in a patient with glioma," Nat. Clin. Pract. Oncol. 6:53-58, Nature Portfolio, Germany (2009).
Yanase, K., et al., "Receptor-mediated cellular entry of nuclear localizing anti-DNA antibodies via myosin 1," J. Clin. Invest. 100:25-31, American Society for Clinical Investigation, United States (1997).
Yu, P., et al., "Simultaneous blockade of multiple immune system inhibitory checkpoints enhances antitumor activity mediated by interleukin-15 in a murine metastatic colon carcinoma model," Clin Cancer Res. 16:6019-6028, American Association for Cancer Research, United States (2010).
Yun, C.O., et al., "Targeting of T lymphocytes to melanoma cells through chimeric anti-GD3 immunoglobulin T-cell receptors," Neoplasia 2:449-459, Elsevier, Netherlands (2000).
Zack, D. J., et al., "DNA mimics a self-protein that may be a target for some anti-DNA antibodies in systemic lupus erythematosus," J. Immunol. 154(4):1987-1994, American Association of Immunologists, United States (Feb. 1995).
Zack, D. J., et al., "Mechanisms of cellular penetration and nuclear localization of an anti-double strand DNA autoantibody," J. Immunol. 157(5):2082-2088, American Association of Immunologists, United States (Sep. 1996).
Zetsche, C., et al., "Cpf1 is a single RNA-guided endonuclease of a class 2 CRISPR-Cas system," Cell 163(3):759-771, Cell Press, United States (2015).
Zhan, X., et al., "Recombinant Fv-Hsp70 protein mediates neuroprotection after focal cerebral ischemia in rats," Stroke. 41(3):538-543, Lippincot Williams & Wilkins, United States (2010).
Zhang, H,, et al., "Lymphopenia and interleukin-2 therapy alter homeostasis of CD4+CD25+ regulatory T cells," Nature Medicine 11:1238-1243, Springer Nature Ltd., Germany (2005).
Zhang, T., et al., "Chimeric NK-receptor-bearing T cells mediate antitumor immunotherapy," Blood 106:1544-1551, American Society of Hematology, United States (2005).
Zhang, X., et al., "Cyclic GMP-AMP containing mixed phosphodiester linkages is an endogenous high-affinity ligand for STING," Mol. Cell. 51(2):226-235, Cell Press, United States (2013).
Zhao, Y., et al., "A herceptin-based chimeric antigen receptor with modified signaling domains leads to enhanced survival of transduced T lymphocytes and antitumor activity" J. Immunol. 183:5563-5574, American Association of Immunologists, United States (2009).
Zhou, J., et al., "Biodegradable poly(amine-co-ester) terpolymers for targeted gene delivery," Nat. Mater. 11(1):82-90, Nature Publishing Group, United Kingdom (Dec. 2011).
Zielke, H. R., and Littlefield, J. W., "Repetitive synchronization of human lymphoblast cultures with excess thymidine," Methods Cell Biol. 8(0):107-121, Elsevier, Netherlands (1974).
Zou, W., et al., "Inhibitory B7-family molecules in the tumour microenvironment" Nat. Rev. Immunol. 8:467-477, Nature Portfolio, Germany (2008).
Hwu, P., et al., "Lysis of ovarian cancer cells by human lymphocytes redirected with a chimeric gene composed of an antibody variable region and the Fc receptor gamma chain," J Exp Med. Jul. 1, 1993;178(1):361-6.
Zack, D. J., et al., "Novel structural features of autoantibodies in murine lupus: a possible superantigen binding site?" Immunol Cell Biol 72(6):513-520, John Wiley & Sons Inc., United States (Dec. 1994).
Non-Final Office Action dated Mar. 3, 2023 in U.S. Appl. No. 17/823,494, Quijano, E., et al., filed Aug. 30, 2022, 21 pages.
Edwards, A.L., et al., "Cellular Uptake and Ultrastructural Localization Underlie the Pro-apoptotic Activity of a Hydrocarbon-stapled BIM BH3 Peptide," ACS Chem. Biol. 10:2149-2157, American Chemical Society, United States (2015).
Olson, G.L., et al., "Concepts and progress in the development of peptide mimetics," J. Med. Chem. 36(21):3039-3049, American Chemical Society, United States (1993).

(56) References Cited

OTHER PUBLICATIONS

Souers, A.J., et al., "ABT-199, a potent and selective BCL-2 inhibitor, achieves antitumor activity while sparing platelets," Nature 435:677-681, Nature Publishing Group, United Kingdom (2013).

Wilson, J., et al., "Up71 and up140, two novel transcripts of utrophin that are homologues of short forms of dystrophin," Human Molecular Genetics 8:1271-1278, Oxford Academic Press, United Kingdom (1999).

Helleday T., et al., "DNA double-strand break repair: from mechanistic understanding to cancer treatment," DNA Repair 6(7):923-935, Elsevier, Netherlands (2007).

Huang, L.C., et al., "Sensitivity and selectivity of the DNA damage sensor responsible for activating p53-dependent G1 arrest," Proc. Natl. Acad. Sci. USA 93(10):4827-4832, National Academy of Sciences, United States (1996).

Jekimovs, C., et al., "Chemotherapeutic compounds targeting the DNA double-strand break repair pathways: the good, the bad, and the promising," Front Oncol 4:86, Frontiers Media S.A., Switzerland (2014).

Krogh, B.O., and Symington, L.S., "Recombination proteins in yeast," Annu. Rev. Genet. 38:233-271, Annual Reviews, United States (2004).

Mimitou, E.P., and Symington, L.S., "DNA end resection: many nucleases make light work," DNA Repair 8(9):983-995, Elsevier, Netherlands (2009).

Morozov, V., and Wawrousek, E. F., "Single-strand DNA-mediated targeted mutagenesis of genomic DNA in early mouse embryos is stimulated by Rad51/54 and by Ku70/86 inhibition," Gene Ther. 15(6):468-472, Nature Publishing Group, United Kingdom (Mar. 2008).

Paques, F., and Haber, J.E., "Multiple pathways of recombination induced by double-strand breaks in *Saccharomyces cerevisiae*," Microbiol. Mol. Biol. Rev. 63(2):349-404, American Society for Microbiology, United States (1999).

Thompson, L.H., and Schild, D., "Homologous recombinational repair of DNA ensures mammalian chromosome stability," Mutat. Res. 477:131-153, Elsevier, Netherlands (2001).

Co-Pending U.S. Appl. No. 18/054,080, inventors Quijano, E., et al. (Not Published).

Co-Pending U.S. Appl. No. 18/054,101, inventors Quijano, E., et al. (Not Published).

Co-Pending U.S. Appl. No. 17/638,642, inventors Quijano, E., et al., filed Feb. 25, 2022 (Not Published).

Co-Pending U.S. Appl. No. 17/823,494, inventors Quijano, E., et al., filed Aug. 30, 2022 (Not Published).

Piche-Nicholas, N. M., et al., "Changes in Complementarity-determining Regions Significantly Alter IgG Binding to the Neonatal Fc Receptor (FcRn) and Pharmacokinetics," MABS 10(1):81-94, Taylor & Francis, United States (2018).

Imaizumi, T., et al., "Retinoic acid-inducible Gene-I is Induced by double-stranded RNA and Regulates the Expression of CC Chemokine Ligand (CCL) 5 in Human Mesangial Cells," Official Publication of the European Dialysis and Transplant Association—European Renal Association 25(11):3534-3539, Oxford University Press, United Kingdom (Nov. 2010).

Means, T.K., et al., "Human Lupus autoantibody-DNA Complexes Activate DCs Through Cooperation of CD32 and TLR9," The Journal of Clinical Investigation 115(2):407-417, American Society for Clinical Investigation, United States (Feb. 2005).

Zeller, S., et al., "Attachment of Cell-Binding Ligands to Arginine-Rich Cell-Penetrating Peptides Enables Cytosolic Translocation of Complexed siRNA," Chemistry & Biology, 22: 50-62, Cell Press, United States (Jan. 2015).

O'Brien, J., et al., "Overview of Micro RNA Biogenesis, Mechanisms of Actions, and Circulation", Frontiers in Endocrinology, 9:402, Frontiers Media S.A., Switzerland (Aug. 2018).

An, D.S., et al. "Optimization and Functional Effects of Stable Short Hairpin RNA Expression in Primary Human Lymphocytes via Lentiviral Vectors", Molecular Therapy, 14(4): 494-504, American Society of Gene Therapy, United States (2006).

Zeng, et al., "Combination of siRNA-directed Kras oncogene silencing and arsenic-induced apoptosis using nanomedicine strategy for the effective treatment of pancreatic cancer", Nanomedicine: Nanotechnology, Biology, and Medicine, 10: 463-72. (2014).

Gu, W., et al., "Inhibition of cervical cancer cell growth in vitro and in vivo with dual shRNAs", Cancer Gene Therapy, 18: 219-227, Nature Publishing Group, United Kingdom (2011).

Souers, A.J., et al., "ABT-199, a Potent and Selective BCL-2 Inhibitor, Achieves Antitumor Activity While Sparing Platelets," Nature Medicine 19(2):202-208, Nature Publishing Company, United States (Feb. 2013).

Office Action mailed Apr. 13, 2023, in U.S. Appl. No. 17/823,496, Quijano, E., et al., filed Aug. 30, 2022. 23 pages.

Office Action mailed Aug. 1, 2023, in U.S. Appl. No. 17/823,496, Quijano, E., et al., filed Aug. 30, 2022. 17 pages.

\* cited by examiner mRNA Only mRNA + 3E10 D31N (0.1 uM)

COMPOSITIONS AND METHODS FOR DELIVERY OF NUCLEIC ACIDS TO CELLS

CROSS-REFERENCE TO RELATED APPLICATIONS

This application is a continuation of U.S. application Ser. No. 17/638,642, which is the U.S. National Phase entry of International Application No. PCT/US2020/048823, filed Aug. 31, 2020, which claims the benefit of and priority to U.S. Provisional Application No. 62/944,281, entitled "Compositions And Methods For Delivery Of Nucleic Acids To Cells", filed in the United States Patent and Trademark Office on Dec. 5, 2019, International Application No. PCT/US2019/048953, entitled "Compositions And Methods For Enhancing Donor Oligonucleotide-Based Gene Editing" and filed in the United States Receiving Office for the Patent Cooperation Treaty on Aug. 30, 2019, and International Application No. PCT/US2019/048962, entitled "Compositions And Methods For Enhancing Triplex And Nuclease-Based Gene Editing" and filed in the United States Receiving Office for the Patent Cooperation Treaty on Aug. 30, 2019. International Application No. PCT/US2020/048823, U.S. Provisional Application No. 62/944,281, International Application No. PCT/US2019/048953, U.S. Provisional Application No. 62/725,920, International Application No. PCT/US2019/048962, U.S. Provisional Application No. 62/725,852 are each specifically incorporated by reference in their entireties.

STATEMENT REGARDING FEDERALLY SPONSORED RESEARCH

This invention was made with government support under CA197574 awarded by National Institutes of Health. The Government has certain rights in the invention.

REFERENCE TO THE SEQUENCE LISTING

The content of the electronically submitted sequence listing (Name: 2681_122000C_Seqlisting_ST26; Size: 113,943 bytes; and Date of Creation: Nov. 10, 2022) is herein incorporated by reference in its entirety.

FIELD OF THE INVENTION

The invention is generally related to the field of intracellular delivery of nucleic acids, for application including, but not limited to in vitro, ex vivo, and in vivo gene therapy and gene editing.

BACKGROUND OF THE INVENTION

Gene therapy includes a spectrum of applications ranging from gene replacement and knockdown for genetic or acquired diseases such as cancer, to vaccination. Viral vectors and synthetic liposomes have emerged as the vehicles of choice for many applications today, but both have limitations and risks, including complexity of production, limited packaging capacity, and unfavorable immunological features, which restrict gene therapy applications and hold back the potential for preventive gene therapy (Seow and Wood, *Mol Ther.* 17(5): 767-777 (2009)).

In vivo uptake and distributed of nucleotide in cells and tissues has been observed (Huang, et al., FEBS Lett., 558 (1-3):69-73 (2004)). Further, although, for example, Nyce, et al. have shown that antisense oligodeoxynucleotides (ODNs) when inhaled bind to endogenous surfactant (a lipid produced by lung cells) and are taken up by lung cells without a need for additional carrier lipids (Nyce, et al., *Nature,* 385:721-725 (1997)), small nucleic acids are taken up into T24 bladder carcinoma tissue culture cells (Ma, et al., *Antisense Nucleic Acid Drug Dev.,* 8:415-426 (1998)), there remains a need for improved nucleic acid transfection technology, particularly for in vivo applications. AAV9, still the viral vector typically used in people was discovered in 2003 (Robbins, "Gene therapy pioneer says the field is behind—and that delivery technology is embarrassing," *Stat,* November, 2019).

Thus, it is an object of the invention to provided compositions and methods of use thereof for improved delivery of nucleic acids into cells.

SUMMARY OF THE INVENTION

Compositions and methods of use thereof for delivering nucleic acid cargo into cells are provided. The compositions typically include (a) a 3E10 monoclonal antibody or a cell-penetrating fragment thereof; a monovalent, divalent, or multivalent single chain variable fragment (scFv); or a diabody; or humanized form or variant thereof, and (b) a nucleic acid cargo including, for example, a nucleic acid encoding a polypeptide, a functional nucleic acid, a nucleic acid encoding a functional nucleic acid, or a combination thereof. Elements (a) and (b) are typically non-covalently linked to form a complex. It is believed that in additional to DNA, 3E10 binds to RNA, PNA, and other nucleic acids.

Exemplary 3E10 antibodies and fragments and fusion protein thereof include those having (i) the CDRs of any one of SEQ ID NO:1-6, 12, 13, 46-48, or 50-52 in combination with the CDRs of any one of SEQ ID NO:7-11, 14, or 53-58; (ii) first, second, and third heavy chain CDRs selected from SEQ ID NOS:15-23, 42, and 43 in combination with first, second and third light chain CDRs selected from SEQ ID NOS:24-30, 44, and 45; (iii) a humanized forms of (i) or (ii); (iv) a heavy chain comprising an amino acid sequence comprising at least 85% sequence identity to any one of SEQ ID NO:1 or 2 in combination with a light chain comprising an amino acid sequence comprising at least 85% sequence identity to SEQ ID NO:7 or 8; (v) a humanized form or (iv); or (vi) a heavy chain comprising an amino acid sequence comprising at least 85% sequence identity to any one of SEQ ID NO:3-6, 46-48, or 50-52 in combination with a light chain comprising an amino acid sequence comprising at least 85% sequence identity to SEQ ID NO:9-11 or 53-58.

In some embodiments, the antibodies and fragments and fusion protein thereof is CDR1 heavy chain variant having the amino acid residue corresponding with D31 or N31 of a 3E10 heavy chain amino acid sequence or a CDR thereof substituted with arginine (R) or lysine (L).

In some embodiments, the antibodies and fragments and fusion protein thereof include the nucleic acid binding pocket of SEQ ID NOS:92 or 93, or a variant thereof with same or improved ability to bind to a nucleic acid, such as DNA, RNA, or a combination thereof.

Also provided are binding proteins themselves including a CDR1 heavy chain variant having the amino acid residue corresponding with D31 or N31 of a 3E10 heavy chain amino acid sequence or the CDR1 thereof substituted with arginine (R) or lysine (L), as well as binding proteins themselves having the nucleic acid binding pocket of SEQ ID NOS:92 or 93, or a variant thereof with same or improved ability to bind to a nucleic acid, such as DNA, RNA, or a combination thereof.

In some embodiments, the antibody or fragment or fusion protein can be bispecific, and can, for example, include a binding sequence that targets a cell type, tissue, or organ of interest.

The nucleic acid cargo can be composed of DNA, RNA, modified nucleic acids, including but not limited to, PNA, or a combination thereof. The nucleic acid cargo is typically a functional cargo, such as a functional nucleic (e.g., an inhibitory RNA), an mRNA, or a vector, for example an expression vector. The nucleic acid cargo, including vectors, can include a nucleic acid sequence encoding a polypeptide of interest operably linked to expression control sequence. The vector can be, for example, a plasmid. Typically the cargo is not, for example, randomly sheared or fragment genomic DNA.

In some embodiments, the cargo includes or consists of a nucleic acid encoding a Cas endonuclease, a gRNA, or a combination thereof. In some embodiments, the cargo includes or consists of a nucleic acid encoding a chimeric antigen receptor polypeptide. In some embodiments, the cargo is a functional nucleic acid such as antisense molecules, siRNA, microRNA (miRNA), aptamers, ribozymes, RNAi, or external guide sequences, or a nucleic acid construct encoding the same.

The cargo can include or consist of a plurality of a single nucleic acid molecule, or a plurality of 2, 3, 4, 5, 6, 7, 8, 9, 10, or more different nucleic acid molecules. In some embodiments, the nucleic acid molecules of cargo include or consists of nucleic acid molecules between about 1 and about 25,000 nucleobases in length. The cargo can be single stranded nucleic acids, double stranded nucleic acids, or a combination thereof.

Pharmaceutical compositions including the complexes and a pharmaceutically acceptable excipient are also provided. In some embodiments, the complexes are encapsulated in polymeric nanoparticles. A targeting moiety, a cell-penetrating peptide, or a combination thereof can be associated with, linked, conjugated, or otherwise attached directly or indirectly to the nanoparticle.

Methods of delivering into cells, the nucleic acid cargo, by contacting the cells with an effective amount of the complexes alone or encapsulated in nanoparticles are also provided. The contacting can occur in vitro, ex vivo, or in vivo. In some embodiments, an effective amount of ex vivo treated cells are administered to a subject in need thereof, e.g., in an effective amount to treat one or more symptoms of a disease or disorder.

In some embodiments, the contacting occurs in vivo following administration to a subject in need thereof. The subject can have a disease or disorder, such as a genetic disorder or cancer. The compositions can be administered to the subject, for example by injection or infusion, in an effective amount to reduce one or more symptoms of the disease or disorder in the subject.

Applications of the compositions and methods are also provided, and include, but are not limited to, gene therapy and CAR T cell manufacture/formation/therapy.

DETAILED DESCRIPTION OF THE INVENTION

I. Definitions

Figure 1A:
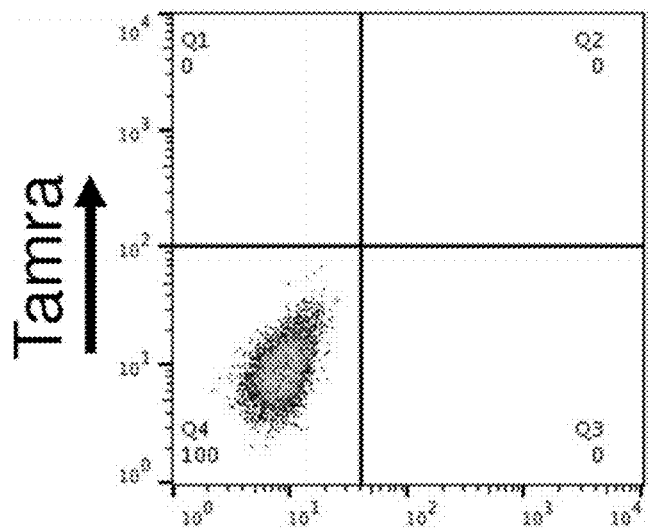
FIGS. 1A-1C are scatter plots showing control (1A), and uptake of PNA when alone (1B) and when mixed with 3E10 for 1 hour (1C).

As used herein, the term "single chain Fv" or "scFv" as used herein means a single chain variable fragment that includes a light chain variable region (VL) and a heavy chain variable region (VH) in a single polypeptide chain joined by a linker which enables the scFv to form the desired structure for antigen binding (i.e., for the VH and VL of the single polypeptide chain to associate with one another to form a Fv). The VL and VH regions may be derived from the parent antibody or may be chemically or recombinantly synthesized.

As used herein, the term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, MD. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917).

As used herein, the term "Framework Region" or "FR" residues are those variable domain residues other than the hypervariable region residues as herein defined.

As used herein, the term "antibody" refers to natural or synthetic antibodies that bind a target antigen. The term includes polyclonal and monoclonal antibodies. In addition to intact immunoglobulin molecules, also included in the term "antibodies" are binding proteins, fragments, and polymers of those immunoglobulin molecules, and human or humanized versions of immunoglobulin molecules that bind the target antigen.

As used herein, the term "cell-penetrating antibody" refers to an immunoglobulin protein, fragment, variant thereof, or fusion protein based thereon that is transported into the cytoplasm and/or nucleus of living mammalian cells. The "cell-penetrating anti-DNA antibody" specifically binds DNA (e.g., single-stranded and/or double-stranded DNA). In some embodiments, the antibody is transported into the cytoplasm of the cells without the aid of a carrier or conjugate. In other embodiments, the antibody is conjugated to a cell-penetrating moiety, such as a cell penetrating peptide. In some embodiments, the cell-penetrating antibody is transported in the nucleus with or without a carrier or conjugate.

In addition to intact immunoglobulin molecules, also included in the term "antibodies" are fragments, binding proteins, and polymers of immunoglobulin molecules, chimeric antibodies containing sequences from more than one species, class, or subclass of immunoglobulin, such as human or humanized antibodies, and recombinant proteins containing a least the idiotype of an immunoglobulin that specifically binds DNA. The antibodies can be tested for their desired activity using the in vitro assays described herein, or by analogous methods, after which their in vivo therapeutic activities are tested according to known clinical testing methods.

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

As used herein, the term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or includes a certain % sequence identity to, with, or against a given sequence D) is calculated as follows:

100 times the fraction $W/Z$, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "specifically binds" refers to the binding of an antibody to its cognate antigen (for example, DNA) while not significantly binding to other antigens. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity. Preferably, an antibody "specifically binds" to an antigen with an affinity constant (Ka) greater than about $10^5$ mol$^{-1}$ (e.g., $10^6$ mol$^{-1}$, $10^7$ mol$^{-1}$, $10^8$ mol$^{-1}$, $10^9$ mol$^{-1}$, $10^{10}$ mol$^{-1}$, $10^{11}$ mol$^{-1}$, and $10^{12}$ mol$^{-1}$ or more) with that second molecule.

As used herein, the term "monoclonal antibody" or "MAb" refers to an antibody obtained from a substantially homogeneous population of antibodies, i.e., the individual antibodies within the population are identical except for possible naturally occurring mutations that may be present in a small subset of the antibody molecules.

As used herein, the term "subject" means any individual who is the target of administration. The subject can be a vertebrate, for example, a mammal. Thus, the subject can be a human. The term does not denote a particular age or sex.

As used herein, the term "effective amount" means that the amount of the composition used is of sufficient quantity to ameliorate one or more causes or symptoms of a disease or disorder. Such amelioration only requires a reduction or alteration, not necessarily elimination. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "pharmaceutically acceptable" refers to a material that is not biologically or otherwise undesirable, i.e., the material may be administered to a subject without causing any undesirable biological effects or interacting in a deleterious manner with any of the other components of the pharmaceutical composition in which it is contained.

As used herein, the term "carrier" or "excipient" refers to an organic or inorganic ingredient, natural or synthetic inactive ingredient in a formulation, with which one or more active ingredients are combined. The carrier or excipient would naturally be selected to minimize any degradation of the active ingredient and to minimize any adverse side effects in the subject, as would be well known to one of skill in the art.

As used herein, the term "treat" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "targeting moiety" is a substance which can direct a particle or molecule to a receptor site on a selected cell or tissue type, can serve as an attachment molecule, or serve to couple or attach another molecule. As used herein, "direct" refers to causing a molecule to preferentially attach to a selected cell or tissue type. This can be used to direct cellular materials, molecules, or drugs, as discussed below.

As used herein, the term "inhibit" or "reduce" means to decrease an activity, response, condition, disease, or other biological parameter. This can include, but is not limited to, the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

As used herein, a "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from a nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid sequence, and then expressing the nucleic acid in an appropriate host cell under conditions in which the fusion protein is produced.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied.

All methods described herein can be performed in any suitable order unless otherwise indicated or otherwise clearly contradicted by context. The use of any and all examples, or exemplary language (e.g., "such as") provided herein, is intended merely to better illuminate the embodiments and does not pose a limitation on the scope of the embodiments unless otherwise claimed. No language in the specification should be construed as indicating any non-claimed element as essential to the practice of the invention.

II. Compositions

It has been discovered that 3E10 antibody helps deliver nucleic acids across the plasma membrane and into cell cytoplasm and nuclei. Thus, compositions and methods for using 3E10 to enhance delivery of nucleic acid constructs are provided. Typically an effective amount of 3E10 antibody is contacted with a nucleic acid whose delivery into cells is desired. Typically, the contacting occurs for a sufficient amount to time for the 3E10 and the nucleic acid cargo to form a complex. The complexes are contacted with cells for a sufficient amount of time for the nucleic acid cargo to be delivered into the cells. The cargo may accumulate in a greater quantity, greater quality (e.g., more intact, functional, etc.), or a faster rate, or combination thereof, than if the cells were contacted with the nucleic acid cargo in the absence of the antibody. Because the antibody serves as the delivery means, the delivery systems are typically non-viral.

A. 3E10 Antibodies

Although generally referred to herein as "3E10" or "3E10 antibodies," it will be appreciated that fragments and binding proteins, including antigen-binding fragments, variants, and fusion proteins such as scFv, di-scFv, tr-scFv, and other single chain variable fragments, and other cell-penetrating, nucleic acid transporting molecules disclosed herein are encompassed by the phrase are also expressly provided for use in compositions and methods disclosed herein. Thus, the antibodies and other binding proteins are also referred to herein as cell-penetrating.

In preferred embodiments, the 3E10 antibody is transported into the cytoplasm and/or nucleus of the cells without the aid of a carrier or conjugate. For example, the monoclonal antibody 3E10 and active fragments thereof that are transported in vivo to the nucleus of mammalian cells without cytotoxic effect are disclosed in U.S. Pat. Nos. 4,812,397 and 7,189,396 to Richard Weisbart.

In some embodiments, the antibody may bind and/or inhibit Rad51. See for example, the antibody described in Turchick, et al., *Nucleic Acids Res.*, 45(20): 11782-11799 (2017), WO 2020/047344, and WO 2020/047353, each of which is specifically incorporated by reference herein, in its entirety.

Antibodies that can be used in the compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies. Therefore, the antibodies typically contain at least the CDRs necessary to maintain DNA binding and/or interfere with DNA repair.

The 3E10 antibody is typically a monoclonal 3E10, or a variant, derivative, fragment, fusion, or humanized form thereof that binds the same or different epitope(s) as 3E10.

A deposit according to the terms of the Budapest Treaty of a hybridoma cell line producing monoclonal antibody 3E10 was received on Sep. 6, 2000, and accepted by, American Type Culture Collection (ATCC), 10801 University Blvd., Manassas, VA 20110-2209, USA, and given Patent Deposit Number PTA-2439.

Thus, the antibody may have the same or different epitope specificity as monoclonal antibody 3E10 produced by ATCC No. PTA 2439 hybridoma. The antibody can have the paratope of monoclonal antibody 3E10. The antibody can be a single chain variable fragment of 3E10, or a variant, e.g., a conservative variant thereof. For example, the antibody can be a single chain variable fragment of 3E10 (3E10 Fv), or a variant thereof.

1. 3E10 Sequences

Amino acid sequences of monoclonal antibody 3E10 are known in the art. For example, sequences of the 3E10 heavy and light chains are provided below, where single underlining indicates the CDR regions identified according to the Kabat system, and in SEQ ID NOS:12-14 italics indicates the variable regions and double underlining indicates the signal peptide. CDRs according to the IMGT system are also provided.

a. 3E10 Heavy Chain

In some embodiments, a heavy chain variable region of 3E10 is:

(SEQ ID NO: 1; Zack, et al., *Immunology and Cell Biology*, 72:513-520 (1994); GenBank: L16981.1-Mouse Ig rearranged L-chain gene, partial cds; and GenBank: AAA65679.1-immunoglobulin heavy chain, partial [*Mus musculus*])
EVQLVESGGGLVKPGGSRKLSCAASGFTFS<u>DYGMH</u>WVRQAPEKGLEWVA<u>YI
SSGSSTIYYADTVKG</u>RFTISRDNAKNTLFLQMTSLRSEDTAMYYCAR<u>RGLL
LDY</u>WGQGTTLTVSS.

In some embodiments a 3E10 heavy chain is expressed as (3E10 WT Heavy Chain; SEQ ID NO: 12)
<u>MGWSCIILFLVATATGVHS</u>*EVQLVESGGGLVKPGGSRKLSCAASGFTFS*D*Y*
*GMHWVRQAPEKGLEWVAYISSGSSTIYYADTVKGRFTISRDNAKNTLFLQM*
*TSLRSEDTAMYYCARRGLLLDYWGQGTTLTVSS*AASTKGPSVFPLAPSSKST
SGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSL
SLSPGK.

Variants of the 3E10 antibody which incorporate mutations into the wild type sequence are also known in the art, as disclosed for example, in Zack, et al., *J. Immunol.*, 157(5):2082-8 (1996). For example, amino acid position 31 of the heavy chain variable region of 3E10 has been determined to be influential in the ability of the antibody and fragments thereof to penetrate nuclei and bind to DNA (bolded in SEQ ID NOS:1, 2 and 13). A D31N mutation (bolded in SEQ ID NOS:2 and 13) in CDR1 penetrates nuclei and binds DNA with much greater efficiency than the original antibody (Zack, et al., *Immunology and Cell Biology*, 72:513-520 (1994), Weisbart, et al., *J. Autoimmun.*, 11, 539-546 (1998); Weisbart, *Int. J. Oncol.*, 25, 1867-1873 (2004)). In some embodiments, the antibody has the D31N substitution.

In some embodiments, an amino acid sequence for a preferred variant of a heavy chain variable region of 3E10 is:

(SEQ ID NO: 2)
EVQLVESGGGLVKPGGSRKLSCAASGFTFSNYGMHWVRQAPEKGLEWVA<u>YI
SSGSSTIYYADTVKG</u>RFTISRDNAKNTLFLQMTSLRSEDTAMYYCAR<u>RGLL
LDY</u>WGQGTTLTVSS.

In some embodiments, a 3E10 heavy chain is expressed as (3E10 D31N Variant Heavy Chain; SEQ ID NO: 13)
<u>MGWSCIILFLVATATGVHS</u>*EVQLVESGGGLVKPGGSRKLSCAASGFTF*N*Y*
*GMHWVRQAPEKGLEWVAYISSGSSTIYYADTVKGRFTISRDNAKNTLFLQM*
*TSLRSEDTAMYYCARRGLLLDYWGQGTTLTVSS*AASTKGPSVFPLAPSSKST
SGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSL
SLSPGK.

In some embodiments, the C-terminal serine of SEQ ID NOS:1 or 2 is absent or substituted, with, for example, an alanine, in 3E10 heavy chain variable region.

The complementarity determining regions (CDRs) as identified by Kabat are shown with underlining above and include CDR H1.1 (original sequence): DYGMH (SEQ ID NO:15);

```
CDR H1.2 (with D31N mutation):
                                       (SEQ ID NO: 16)
    NYGMH;

CDR H2.1:
                                       (SEQ ID NO: 17)
    YISSGSSTIYYADTVKG;

CDR H3.1:
                                       (SEQ ID NO: 18)
    RGLLLDY.

Variants of Kabat CDR H2.1 include
                                       (SEQ ID NO: 19)
    YISSGSSTIYYADSVKG
    and (SEQ ID NO: 42)
    YISSSSSTIYYADSVKG.
```

Additionally, or alternatively, the heavy chain complementarity determining regions (CDRs) can be defined according to the IMGT system. The complementarity determining regions (CDRs) as identified by the IMGT system include CDR H1.3 (original sequence): GFTFSDYG (SEQ ID NO:20); CDR H1.4 (with D31N mutation): GFTFSNYG (SEQ ID NO:21); CDR H2.2: ISSGSSTI (SEQ ID NO:22) and variant ISSSSSTI (SEQ ID NO:43); CDR H3.2: ARRGLLLDY (SEQ ID NO:23).

b. 3E10 Light Chain

In some embodiments, a light chain variable region of 3E10 is:

(SEQ ID NO: 7)
DIVLTQSPASLAVSLGQRATI<u>SCRASKSVSTSSYSYMH</u>WYQQKPGQPPKLL
IK<u>YASYLES</u>GVPARFSGSGSGTDFTLNIHPVEEEDAATYYC<u>QHSREFPWT</u>F
GGGTKLEIK.

An amino acid sequence for the light chain variable region of 3E10 can also be:

(SEQ ID NO: 8)
DIVLTQSPASLAVSLGQRATISCRASKSVSTSSYSYMHWYQQKPGQPPKLL

IKYASYLESGVPARFSGSGSGTDFHLNIHPVEEEDAATYYCQHSREFPWTF

GGGTKLELK.

In some embodiments, a 3E10 light chain is expressed as (3E10 WT Light Chain; SEQ ID NO: 14)
MGWSCIILFLVATATGVHSDIVLTQSPASLAVSLGQRATISCRASKSVSTS

SYSYMHWYQQKPGQPPKLLIKYASYLESGVPARFSGSGSGTDFTLNIHPVE

EEDAATYYCQHSREFPWTFGGGTKLEIKRTVAAPSVFIFPPSDEQLKSGTA

SVVCLLNNFYPREAKVQWKVDNALQSGNSQESVTEQDSKDSTYSLSSTLTL

SKADYEKHKVYACEVTHQGLSSPVTKSFNRGEC

Other 3E10 light chain sequences are known in the art. See, for example, Zack, et al., *J. Immunol.*, 15; 154(4):1987-94 (1995); GenBank: L16981.1—Mouse Ig rearranged L-chain gene, partial cds; GenBank: AAA65681.1—immunoglobulin light chain, partial [*Mus musculus*]).

The complementarity determining regions (CDRs) as identified by Kabat are shown with underlining, including CDR L1.1: RASKSVSTSSYSYMH (SEQ ID NO:24); CDR L2.1: YASYLES (SEQ ID NO:25); CDR L3.1: QHSREFPWT (SEQ ID NO:26).

Variants of Kabat CDR L1.1 include
                                    (SEQ ID NO: 27)
        RASKSVSTSSYSYLA
        and (SEQ ID NO: 44)
        RASKTVSTSSYSYMH.
        A variant of Kabat CDR L2.1 is
                                    (SEQ ID NO: 28)
        YASYLQS.

Additionally, or alternatively, the heavy chain complementarity determining regions (CDRs) can be defined according to the IMGT system. The complementarity determining regions (CDRs) as identified by the IMGT system include CDR L1.2 KSVSTSSYSY (SEQ ID NO:29) and variant KTVSTSSYSY (SEQ ID NO:45); CDR L2.2: YAS (SEQ ID NO:30); CDR L3.2: QHSREFPWT (SEQ ID NO:26).

In some embodiments, the C-terminal end of sequence of SEQ ID NOS:7 or 8 further includes an arginine in the 3E10 light chain variable region.

2. Humanized 3E10

In some embodiments, the antibody is a humanized antibody. Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule.

Exemplary 3E10 humanized sequences are discussed in WO 2015/106290, WO 2016/033324, WO 2019/018426, and WO/2019/018428, and provided below.

a. Humanized 3E10 Heavy Chain Variable Regions

In some embodiments, a humanized 3E10 heavy chain variable domain includes (hVH1, SEQ ID NO: 3)
EVQLVQSGGGLIQPGGSLRLSCAASGFTFSNYGMHWVRQAPGKGLEWVSYI

SSGSSTIYYADSVKGRFTISRDNSKNTLYLQMNSLRAEDTAVYYCARRGLL

LDYWGQGTTVTVSS,
or (hVH2, SEQ ID NO: 4)
EVQLVESGGGLIQPGGSLRLSCAASGFTFSNYGMHWVRQAPGKGLEWVSYI

SSGSSTIYYADSVKGRFTISRDNSKNTLYLQMTSLRAEDTAVYYCARRGLL

LDYWGQGTTLTVSS,
or (hVH3, SEQ ID NO: 5)
EVQLQESGGGVVQPGGSLRLSCAASGFTFSNYGMHWIRQAPGKGLEWVSYI

SSGSSTIYYADSVKGRFTISRDNSKNTLYLQMNSLRSEDTAVYYCARRGLL

LDYWGQGTLVTVSS,
or (hVH4, SEQ ID NO: 6)
EVQLVESGGGLVQPGGSLRLSCSASGFTFSNYGMHWVRQAPGKGLEYVSYI

SSGSSTIYYADTVKGRFTISRDNSKNTLYLQMSSLRAEDTAVYYCVKRGLL

LDYWGQGTLVTVSS,
or (variants 2, 6 and 10, SEQ ID NO: 46)
EVQLVESGGGLVQPGGSLRLSCAASGFTFSNYGMHWVRQAPGKGLEWVSYI

SSSSSTIYYADSVKGRFTISRDNAKNSLYLQMNSLRAEDTAVYYCARRGLL

LDYWGQGTTVTVSS,
or (variants 3, 7 and 11, SEQ ID NO: 47)
EVQLVESGGGVVQPGGSLRLSCAASGFTFSNYGMHWVRQAPEKGLEWVSYI

SSSSSTIYYADSVKGRFTISRDNSKNTLYLQMNSLRAEDTAVYYCARRGLL

LDYWGQGTTVTVSS,
or (variants 4, 8 and 12, SEQ ID NO: 48)
EVQLVESGGGDVKPGGSLRLSCAASGFTFSNYGMHWVRQAPEKGLEWVSYI

SSSSSTIYYADSVKGRFTISRDNSKNTLYLQMNSLRAEDTAVYYCARRGLL

LDYWGQGTTVTVSS,
or (variants 13, 16 and 19, SEQ ID NO: 50)
EVQLVESGGGLVQPGGSLRLSCAASGFTFSNYGMHWVRQAPGKGLEWVSYI

SSGSSTIYYADSVKGRFTISRDNAKNSLYLQMNSLRAEDTAVYYCARRGLL

LDYWGQGTTVTVSS,
or (variants 14 and 17, SEQ ID NO: 51)
EVQLVESGGGVVQPGGSLRLSCAASGFTFSNYGMHWVRQAPEKGLEWVSYI

SSGSSTIYYADSVKGRFTISRDNSKNTLYLQMNSLRAEDTAVYYCARRGLL

LDYWGQGTTVTVSS, or (variants 15 and 18, SEQ ID NO: 52)
EVQLVESGGGDVKPGGSLRLSCAASGFTFSNYGMHWVRQAPEKGLEWVSYI
SSGSSTIYYADSVKGRFTISRDNSKNTLYLQMNSLRAEDTAVYYCARRGLL
LDYWGQGTTVTSS.

b. Humanized 3E10 Light Chain Variable Regions (hVL1, SEQ ID NO: 9)
DIQMTQSPSSLSASVGDRVTITCRASKSVSTSSYSYLAWYQQKPEKAPKLL
IKYASYLQSGVPSRFSGSGSGTDFTLTISSLQPEDFATYYCQHSREFPWTF
GAGTKLELK,
or (hVL2, SEQ ID NO: 10)
DIQMTQSPSSLSASVGDRVTISCRASKSVSTSSYSYMHWYQQKPEKAPKLL
IKYASYLQSGVPSRFSGSGSGTDFTLTISSLQPEDVATYYCQHSREFPWTF
GAGTKLELK,
or (hVL3, SEQ ID NO: 11)
DIVLTQSPASLAVSPGQRATITCRASKSVSTSSYSYMHWYQQKPGQPPKLL
IYYASYLESGVPARFSGSGSGTDFTLTINPVEANDTANYYCQHSREFPWTF
GQGTKVEIK (variants 2, 3 and 4, SEQ ID NO: 53)
DIQMTQSPSSLSASLGDRATITCRASKSVSTSSYSYMHWYQQKPGQPPKLL
IKYASYLESGVPSRFSGSGSGTDFTLTISSLQPEDAATYYCQHSREFPWTF
GGGTKVEIK (variants 6, 7 and 8, SEQ ID NO: 54)
DIQMTQSPSSLSASLGDRATITCRASKSVSTSSYSYMHWYQQKPGQAPKLL
IKYASYLESGVPSRFSGSGSGTDFTLTISSLQPEDFATYYCQHSREFPWTF
GQGTKVEIK (variants 10, 11 and 12, SEQ ID NO: 55)
DIQMTQSPSSLSASVGDRVTITCRASKSVSTSSYSYMHWYQQKPGKAPKLL
IKYASYLESGVPSRFSGSGSGTDFTLTISSLQPEDFATYYCQHSREFPWTF
GQGTKVEIK (variants 13, 14 and 15, SEQ ID NO: 56)
DIQMTQSPSSLSASLGDRATITCRASKTVSTSSYSYMHWYQQKPGQPPKLL
IKYASYLESGVPSRFSGSGSGTDFTLTISSLQPEDAATYYCQHSREFPWTF
GGGTKVEIK (variants 16, 17 and 18, SEQ ID NO: 57)
DIQMTQSPSSLSASVGDRVTITCRASKTVSTSSYSYMHWYQQKPGKAPKLL
IKYASYLESGVPSRFSGSGSGTDFTLTISSLQPEDFATYYCQHSREFPWTF
GQGTKVEIK (variant 19, SEQ ID NO: 58)
DIQMTQSPSSLSASLGDRATITCRASKTVSTSSYSYMHWYQQKPGQAPKLL
IKYASYLESGVPSRFSGSGSGTDFTLTISSLQPEDFATYYCQHSREFPWTF
GQGTKVEIK c. Cell Penetration and Nuclear Localization

The disclosed compositions and methods typically utilize antibodies that maintain the ability to penetrate cells, and optionally nuclei.

The mechanisms of cellular internalization by autoantibodies are diverse. Some are taken into cells through electrostatic interactions or FcR-mediated endocytosis, while others utilize mechanisms based on association with cell surface myosin or calreticulin, followed by endocytosis (Ying-Chyi et al., *Eur J Immunol* 38, 3178-3190 (2008), Yanase et al., *J Clin Invest* 100, 25-31 (1997)). 3E10 penetrates cells in an Fc-independent mechanism (as evidenced by the ability of 3E10 fragments lacking an Fc to penetrate cells) but involves presence of the nucleoside transporter ENT2 (Weisbart et al., *Sci Rep* 5:12022. doi: 10.1038/srep12022. (2015), Zack et al., *J Immunol* 157, 2082-2088 (1996), Hansen et al., *J Biol Chem* 282, 20790-20793 (2007)). Thus, in some embodiments, the antibodies utilized in the disclosed compositions and methods are ones that penetrates cells in an Fc-independent mechanism but involves presence of the nucleoside transporter ENT2.

Mutations in 3E10 that interfere with its ability to bind DNA may render the antibody incapable of nuclear penetration. Thus, typically the disclosed variants and humanized forms of the antibody maintain the ability to bind nucleic acids, particularly DNA. In addition, 3E10 scFv has previously been shown capable of penetrating into living cells and nucleic in an ENT2-dependent manner, with efficiency of uptake impaired in ENT2-deficient cells (Hansen, et al., *J. Biol. Chem.* 282, 20790-20793 (2007)). Thus, in some embodiments, the disclosed variants and humanized forms of the antibody maintain the ability penetrate into cell nuclei in an ENT-dependent, preferably ENT2-dependent manner.

As discussed in WO 2019/152806 and WO 2019/152808 some humanized 3E10 variant were found to penetrate cell nuclei more efficiently than the original murine 3E10 (D31N) di-scFv, while others were found to have lost the ability to penetrate nuclei. In particular, variants 10 and 13 penetrated nuclei very well compared to the murine antibody.

Potential bipartite nuclear localization signals (NLS) in humanized 3E10 VL have been identified and may include part or all of the following sequences:

(SEQ ID NO: 88)
RASK*S*VSTSSYSYMHWYQQKPGQPPKLLIKY;

(SEQ ID NO: 89)
RASK*T*VSTSSYSYMHWYQQKPGQPPKLLIKY;
or (SEQ ID NO: 90)
*RVTIT*CRASKSVSTSSYSYMHWYQQKPGKAPKL.

An exemplary consensus NLS can be, or include, (X)RASKTVSTSSYSYMHWYQQKPGQPPKLL(X)KY (where (X)=any residue, but preferentially is a basic residue (R or K) (SEQ ID NO:91) or a variant thereof with at least 60, 65, 70, 75, 80, 85, 90, 95, 96, 97, 98, 99 percent sequence identity to SEQ ID NO:53.

Thus, in some embodiments, particularly where nuclear importation is important, the disclosed antibodies may include the sequence of any one of SEQ ID NOS:88-91, or fragments and variants thereof (e.g., 70, 75, 80, 85, 90, 95, 96, 97, 98, 99, or 100% amino acid sequence identity with any one of SEQ ID NOS:88-91) that can translocate into the nucleus of a cell.

Presence of an NLS indicates that 3E10 may cross the nuclear envelope via the nuclear import pathway. In some embodiments, the NLS improves importation by interacting with one or more members of the import pathway. Thus, in some embodiments, the NLS can bind to importin-β, an importin-β/importin-α heterodimer, or a combination thereof.

3. Nucleic Acid Binding

The disclosed compositions and methods typically utilize antibodies that maintain the ability to bind nucleic acids such as DNA, RNA, or a combination thereof.

The Examples below illustrate molecular modeling of 3E10 and additional 3E10 variants. Molecular modeling of 3E10 (Pymol) revealed a putative Nucleic Acid Binding pocket (NAB1) (see, e.g., FIGS. 14A and 14B), and illustrated with underlining the sequences below.

```
WT HEAVY CHAIN scFv SEQUENCE
                                    (SEQ ID NO: 92)
E VQLVESGGGL VKPGGSRKLS CAASGFTFSD YGMHWVRQAP

EKGLEWVAYI SSGSSTIYYA DTVKGRFTIS RDNAKNTLFL

QMTSLRSEDT AMYYCARRGL LLDYWGQGTT LTVS

LIGHT CHAIN scFv SEQUENCE
                                    (SEQ ID NO: 93)
D IVLTQSPASL AVSLGQRATI SCRASKSVST SSYSYMHWYQ

QKPGQPPKLL IKYASYLESG VPARFSGSGS GTDFTLNIHP

VEEEDAATYY CQHSREFPWT FGGGTKLEIK RADAAPGGGG

SGGGGSGGGGS
```

In some embodiments, the disclosed antibodies include some or all of the underlined NAB1 sequences. In some embodiments, the antibodies include a variant sequence that has an altered ability of bind nucleic acids. In some embodiments, the mutations (e.g., substitutions, insertions, and/or deletions) in the NAB1 improve binding of the antibody to nucleic acids such as DNA, RNA, or a combination thereof. In some embodiments, the mutations are conservative substitutions. In some embodiments, the mutations increase the cationic charge of the NAB1 pocket.

As discussed and exemplified herein, mutation of aspartic acid at residue 31 of CDR1 to asparagine increased the cationic charge of this residue and enhanced nucleic acid binding and delivery in vivo (3E10-D31N).

Additional exemplary variants include mutation of aspartic acid at residue 31 of CDR1 to arginine (3E10-D31R), which modeling indicates expands cationic charge, or lysine (3E10-D31K) which modeling indicates changes charge orientation. Thus, in some embodiments, the 3E10 binding protein includes a D31R or D31K substitution.

All of the sequences disclosed herein having the residue corresponding to 3E10 D31 or N31, are expressly disclosed with a D31R or D31K or N31R or N31K substitution therein.

Figure 14A:
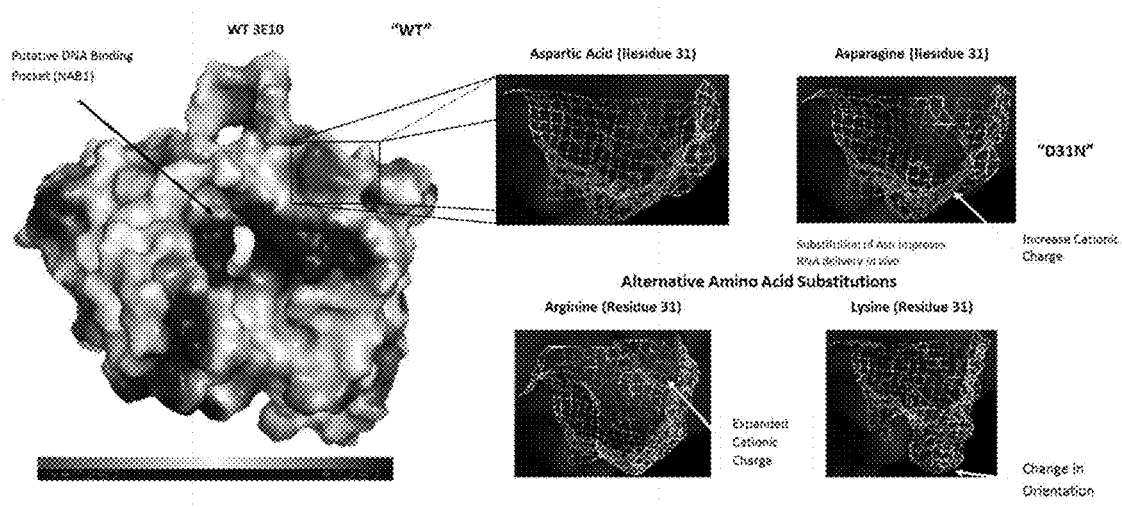
FIG. 14A is an illustration of molecular modeling of 3E10, a putative Nucleic Acid Binding pocket (NAB1) thereof, and the predicted structural changes induced by amino acid mutations therein.
Figure 14B:
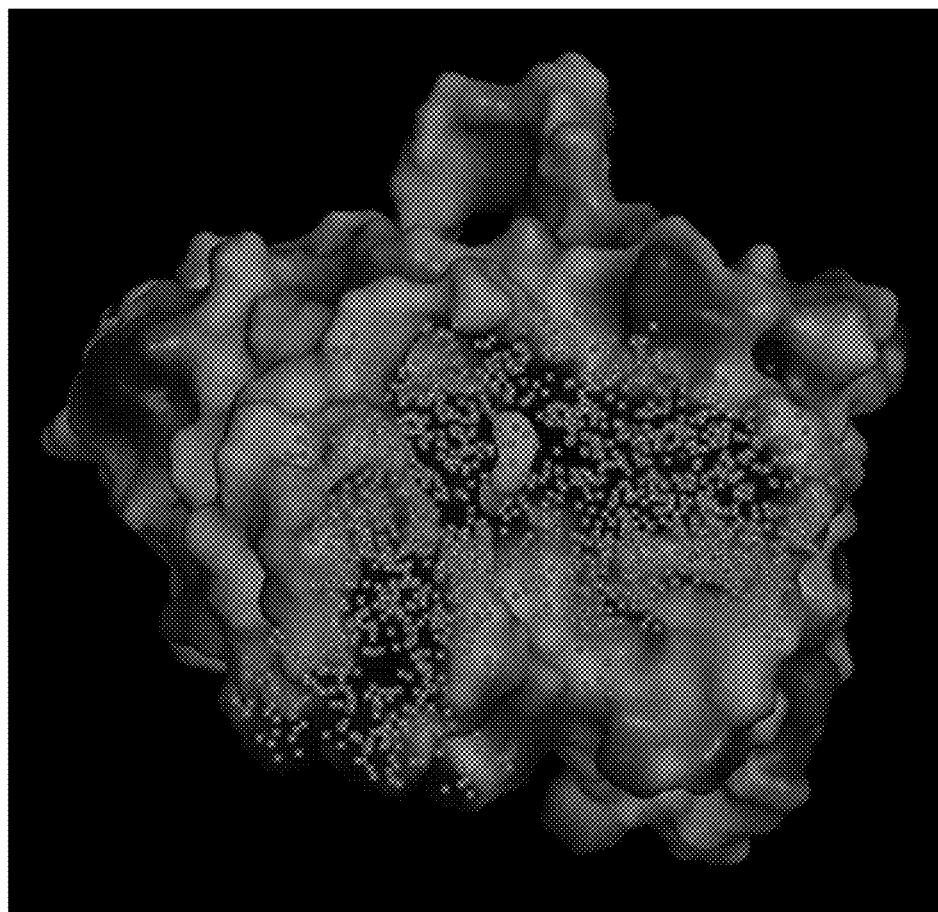
FIG. 14B is an illustration of molecular modeling of 3E10-scFv (Pymol) with NAB1 amino acid residues highlighted by punctate dots.

Molecular modeling of 3E10 (Pymol) revealed a putative Nucleic Acid Binding pocket (NAB1) (FIGS. 14A-14B). Mutation of aspartic acid at residue 31 of CDR1 to asparagine increased the cationic charge of this residue and enhanced nucleic acid binding and delivery in vivo (3E10-D31N).

Mutation of aspartic acid at residue 31 of CDR1 to arginine (3E10-D31R), further expanded the cationic charge while mutation to lysine (3E10-D31K) changed charge orientation (FIG. 14A).

NAB1 amino acids predicted from molecular modeling have been underlined in the heavy and light chain sequences above. FIG. 14B is an illustration showing molecular modeling of 3E10-scFv (Pymol) with NAB1 amino acid residues illustrated with punctate dots.

4. Fragments, Variants, and Fusion Proteins

The anti-DNA antibody can be composed of an antibody fragment or fusion protein including an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, at least 99%, or 100% identical to the amino acid sequence of the variable heavy chain and/or light chain of 3E10 or a humanized form thereof (e.g., any of SEQ ID NOS:1-11 or 46-58, or the heavy and/or light chains of any of SEQ ID NOS:12-14).

The anti-DNA antibody can be composed of an antibody fragment or fusion protein that includes one or more CDR(s) that is at least 45%, at least 50%, at least 55%, at least 60%, at least 65%, at least 70%, at least 75%, at least 80%, at least 85%, at least 90%, at least 95%, at least 99%, or 100% identical to the amino acid sequence of the CDR(s) of 3E10, or a variant or humanized form thereof (e.g., CDR(s) of any of SEQ ID NOS:1-11 or 46-58, or SEQ ID NOS:12-14, or SEQ ID NOS:15-30 or 42-45). The determination of percent identity of two amino acid sequences can be determined by BLAST protein comparison. In some embodiments, the antibody includes one, two, three, four, five, or all six of the CDRs of the above-described preferred variable domains.

Preferably, the antibody includes one of each of a heavy chain CDR1, CDR2, and CDR3 in combination with one of each of a light chain CDR1, CDR2, and CDR3.

Predicted complementarity determining regions (CDRs) of the light chain variable sequence for 3E10 are provided above. See also GenBank: AAA65681.1—immunoglobulin light chain, partial [*Mus musculus*] and GenBank: L34051.1—Mouse Ig rearranged kappa-chain mRNA V-region. Predicted complementarity determining regions (CDRs) of the heavy chain variable sequence for 3E10 are provide above. See also, for example, Zack, et al., *Immunology and Cell Biology*, 72:513-520 (1994), GenBank Accession number AAA65679.1. Zach, et al., *J. Immunol.* 154 (4), 1987-1994 (1995) and GenBank: L16982.1—Mouse Ig reagrranged H-chain gene, partial cds.

Thus, in some embodiments, the cell-penetrating antibody contains the CDRs, or the entire heavy and light chain variable regions, of SEQ ID NO:1 or 2, or the heavy chain region of SEQ ID NO:12 or 13; or a humanized form thereof in combination with SEQ ID NO:7 or 8, or the light chain region of SEQ ID NO:14; or a humanized form thereof. In some embodiments, the cell-penetrating antibody contains the CDRs, or the entire heavy and light chain variable regions, of SEQ ID NO:3, 4, 5, or 6 in combination with SEQ ID NO:9, 10, or 11. In some embodiments, the cell-penetrating antibody contains the CDRs, or the entire heavy and light chain variable regions, of any one of SEQ ID NO:46-48 or 50-52 in combination with any one of SEQ ID NO:53-58.

All of the sequences disclosed herein having the residue corresponding to 3E10 D31 or N31, are expressly disclosed with a D31R or D31K or N31R or N31K substitution therein. Thus, in some embodiments, the 3E10 binding protein is a variant of any of the foregoing or following sequences wherein the amino acid residue corresponding to residue 31 of the 3E10 heavy chain is substituted with arginine (R) or lysine (K).

Also included are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

The anti-DNA antibodies can be modified to improve their therapeutic potential. For example, in some embodiments, the cell-penetrating anti-DNA antibody is conjugated to another antibody specific for a second therapeutic target in the cytoplasm and/or nucleus of a target cell. For example, the cell-penetrating anti-DNA antibody can be a fusion protein containing 3E10 Fv and a single chain variable fragment of a monoclonal antibody that specifically binds the second therapeutic target. In other embodiments, the cell-penetrating anti-DNA antibody is a bispecific antibody having a first heavy chain and a first light chain from 3E10 and a second heavy chain and a second light chain from a monoclonal antibody that specifically binds the second therapeutic target.

Bispecific antibodies and other binding proteins having a first heavy chain and a first light chain from 3E10 and a second heavy chain and a second light chain from a monoclonal antibody that specifically binds a second target are discussed in Weisbart, et al., *Mol. Cancer Ther.*, 11(10): 2169-73 (2012), and Weisbart, et al., *Int. J. Oncology*, 25:1113-8 (2004), and U.S. Patent Application No. 2013/0266570, which are specifically incorporated by reference in their entireties. In some embodiments, the second target is specific for a target cell-type, tissue, organ etc. Thus the second heavy chain and second light chain can serve as a targeting moiety that targets the complex to the target cell-type, tissue, organ. In some embodiments, the second heavy chain and second light chain target, hematopoietic stem cells, CD34$^+$ cells, T cells or any another preferred cell type, e.g., by targeting a receptor or ligand expressed on the preferred cell type. In some embodiments, the second heavy chain and second light chain target the thymus, spleen, or cancer cells.

In some embodiments, particularly those for targeting T cell in vivo, for example, for in vivo production of CAR T cells, immune cell or T cell markers such as CD3, CD7, or CD8 can be targeted. For example, anti-CD8 antibodies and anti-CD3 Fab fragments have both been used to target T cells in vivo (Pfeiffer, et al., *EMBO Mol Med.*, 10(11) (2018). pii: e9158. doi: 10.15252/emmm.201809158., Smith, et al., *Nat Nanotechnol.*, 12(8):813-820 (2017). doi: 10.1038/nnano.2017.57). Thus, in some embodiments, the 3E10 antibody or antigen binding fragment or fusion protein is a bispecific antibody part of which can bind specifically to CD3, CD7, CD8, or another immune cell (e.g., T cell) marker, or a marker for a specific tissue such as the thymus, spleen, or liver.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies. In some embodiments, the anti-DNA antibody may contain two or more linked single chain variable fragments of 3E10 (e.g., 3E10 di-scFv, 3E10 tri-scFv), or conservative variants thereof. In some embodiments, the anti-DNA antibody is a diabody or triabody (e.g., 3E10 diabody, 3E10 triabody). Sequences for single and two or more linked single chain variable fragments of 3E10 are provided in WO 2017/218825 and WO 2016/033321.

The function of the antibody may be enhanced by coupling the antibody or a fragment thereof with a therapeutic agent. Such coupling of the antibody or fragment with the therapeutic agent can be achieved by making an immunoconjugate or by making a fusion protein, or by linking the antibody or fragment to a nucleic acid such as DNA or RNA (e.g., siRNA), comprising the antibody or antibody fragment and the therapeutic agent.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. The DNA sequence will then be expressed by a cell as a single protein. The protein can be engineered to include the full sequence of both original proteins, or only a portion of either. If the two entities are proteins, often linker (or "spacer") peptides are also added which make it more likely that the proteins fold independently and behave as expected.

In some embodiments, the cell-penetrating antibody is modified to alter its half-life. In some embodiments, it is desirable to increase the half-life of the antibody so that it is present in the circulation or at the site of treatment for longer periods of time. For example, it may be desirable to maintain titers of the antibody in the circulation or in the location to be treated for extended periods of time. In other embodiments, the half-life of the anti-DNA antibody is decreased to reduce potential side effects.

Antibody fragments, such as 3E10Fv may have a shorter half-life than full size antibodies. Other methods of altering half-life are known and can be used in the described methods. For example, antibodies can be engineered with Fc variants that extend half-life, e.g., using Xtend™ antibody half-life prolongation technology (Xencor, Monrovia, CA).

a. Linkers

The term "linker" as used herein includes, without limitation, peptide linkers. The peptide linker can be any size provided it does not interfere with the binding of the epitope by the variable regions. In some embodiments, the linker includes one or more glycine and/or serine amino acid residues. Monovalent single-chain antibody variable fragments (scFvs) in which the C-terminus of one variable domain are typically tethered to the N-terminus of the other variable domain via a 15 to 25 amino acid peptide or linker. The linker is chosen to permit the heavy chain and light chain to bind together in their proper conformational orientation. Linkers in diabodies, triabodies, etc., typically include a shorter linker than that of a monovalent scFv as discussed above. Di-, tri-, and other multivalent scFvs typically include three or more linkers. The linkers can be the same, or different, in length and/or amino acid composition. Therefore, the number of linkers, composition of the linker(s), and length of the linker(s) can be determined based on the desired valency of the scFv as is known in the art. The linker(s) can allow for or drive formation of a di-, tri-, and other multivalent scFv.

For example, a linker can include 4-8 amino acids. In a particular embodiment, a linker includes the amino acid sequence GQSSRSS (SEQ ID NO:31). In another embodiment, a linker includes 15-20 amino acids, for example, 18 amino acids. In a particular embodiment, the linker includes the amino acid sequence GQSSRSSSGGGSSGGGGS (SEQ ID NO:32). Other flexible linkers include, but are not limited to, the amino acid sequences Gly-Ser, Gly-Ser-Gly-Ser (SEQ ID NO:33), Ala-Ser, Gly-Gly-Gly-Ser (SEQ ID NO:34), (Gly$_4$-Ser)$_2$ (SEQ ID NO:35) and (Gly$_4$-Ser)$_4$ (SEQ ID NO:36), and (Gly-Gly-Gly-Gly-Ser)$_3$ (SEQ ID NO:37).

Other exemplary linkers include, for example,

```
                                        (SEQ ID NO: 59)
    RADAAPGGGGSGGGGSGGGGS
and (SEQ ID NO: 60)
    ASTKGPSVFPLAPLESSGS.
``` b. Exemplary anti-DNA scFv Sequences

Exemplary murine 3E10 scFv sequences, including mono-, di-, and tri-scFv are disclosed in WO 2016/033321, WO 2017/218825, WO 2019/018426, and WO/2019/018428, and provided below. Cell-penetrating antibodies for use in the disclosed compositions and methods include exemplary scFv, and fragments and variants thereof.

The amino acid sequence for scFv 3E10 (D31N) is:

```
                                        (SEQ ID NO: 38)
AGIHDIVLTQSPASLAVSLGQRATISCRASKSVSTSSYSYMHWYQQKPGQP

PKLLIKYASYLESGVPARFSGSGSGTDFTLNIHPVEEEDAATYYCQHSREF

PWTFGGGTKLEIKRADAAPGGGGSGGGGSGGGGSEVQLVESGGGLVKPGGS

RKLSCAASGFTFSNYGMHWVRQAPEKGLEWVAYISSGSSTIYYADTVKGRF

TISRDNAKNTLFLQMTSLRSEDTAMYYCARRGLLLDYWGQGTTLTVSSLEQ

KLISEEDLNSAVDHHHHHH.
```

Annotation of scFv Protein Domains with Reference to SEQ ID NO:38
  AGIH sequence increases solubility (amino acids 1-4 of SEQ ID NO:38)
  Vk variable region (amino acids 5-115 of SEQ ID NO:38)
  Initial (6 aa) of light chain CH1 (amino acids 116-121 of SEQ ID NO:38)
  (GGGGS)$_3$ (SEQ ID NO:37) linker (amino acids 122-136 of SEQ ID NO:38)
  VH variable region (amino acids 137-252 of SEQ ID NO:38)
  Myc tag (amino acids 253-268 SEQ ID NO:38)
  His 6 tag (amino acids 269-274 of SEQ ID NO:38)

Amino Acid Sequence of 3E10 Di-scFv (D31N)

Di-scFv 3E10 (D31N) is a di-single chain variable fragment including 2× the heavy chain and light chain variable regions of 3E10 and wherein the aspartic acid at position 31 of the heavy chain is mutated to an asparagine. The amino acid sequence for di-scFv 3E10 (D31N) is:

```
                                        (SEQ ID NO: 39)
AGIHDIVLTQSPASLAVSLGQRATISCRASKSVSTSSYSYMHWYQQKPGQP

PKLLIKYASYLESGVPARFSGSGSGTDFTLNIHPVEEEDAATYYCQHSREF

PWTFGGGTKLEIKRADAAPGGGGSGGGGSGGGGSEVQLVESGGGLVKPGGS

RKLSCAASGFTFSNYGMHWVRQAPEKGLEWVAYISSGSSTIYYADTVKGRF

TISRDNAKNTLFLQMTSLRSEDTAMYYCARRGLLLDYWGQGTTLTVSSAST

KGPSVFPLAPLESSGSDIVLTQSPASLAVSLGQRATISCRASKSVSTSSYS

YMHWYQQKPGQPPKLLIKYASYLESGVPARFSGSGSGTDFTLNIHPVEEED

AATYYCQHSREFPWTFGGGTKLEIKRADAAPGGGGSGGGGSGGGGSEVQLV

ESGGGLVKPGGSRKLSCAASGFTFSNYGMHWVRQAPEKGLEWVAYISSGSS

TIYYADTVKGRFTISRDNAKNTLFLQMTSLRSEDTAMYYCARRGLLLDYWG

QGTTLTVSSLEQKLISEEDLNSAVDHHHHHH.
```

Annotation of di-scFv Protein Domains with Reference to SEQ ID NO:39
  AGIH sequence increases solubility (amino acids 1-4 of SEQ ID NO:39)
  Vk variable region (amino acids 5-115 of SEQ ID NO:39)
  Initial (6 aa) of light chain CH1 (amino acids 116-121 of SEQ ID NO:39)
  (GGGGS)$_3$ (SEQ ID NO:37) linker (amino acids 122-136 of SEQ ID NO:39)
  VH variable region (amino acids 137-252 of SEQ ID NO:39)
  Linker between Fv fragments consisting of human IgG CH1 initial 13 amino acids (amino acids 253-265 of SEQ ID NO:39)
  Swivel sequence (amino acids 266-271 of SEQ ID NO:39)
  Vk variable region (amino acids 272-382 of SEQ ID NO:39)
  Initial (6 aa) of light chain CH1 (amino acids 383-388 of SEQ ID NO:39)
  (GGGGS)$_3$ (SEQ ID NO:37) linker (amino acids 389-403 of SEQ ID NO:39)
  VH variable region (amino acids 404-519 of SEQ ID NO:39)
  Myc tag (amino acids 520-535 of SEQ ID NO:39)
  His 6 tag (amino acids 536-541 of SEQ ID NO:39)

Amino Acid Sequence for Tri-scFv

Tri-scFv 3E10 (D31N) is a tri-single chain variable fragment including 3× the heavy chain and light chain variable regions of 310E and wherein the aspartic acid at position 31 of the heavy chain is mutated to an asparagine. The amino acid sequence for tri-scFv 3E10 (D31N) is:

```
                                        (SEQ ID NO: 40)
AGIHDIVLTQSPASLAVSLGQRATISCRASKSVSTSSYSYMHWYQQKPGQP

PKLLIKYASYLESGVPARFSGSGSGTDFTLNIHPVEEEDAATYYCQHSREF

PWTFGGGTKLEIKRADAAPGGGGSGGGGSGGGGSEVQLVESGGGLVKPGGS

RKLSCAASGFTFSNYGMHWVRQAPEKGLEWVAYISSGSSTIYYADTVKGRF

TISRDNAKNTLFLQMTSLRSEDTAMYYCARRGLLLDYWGQGTTLTVSSAST

KGPSVFPLAPLESSGSDIVLTQSPASLAVSLGQRATISCRASKSVSTSSYS
```

-continued

```
YMHWYQQKPGQPPKLLIKYASYLESGVPARFSGSGSGTDFTLNIHPVEEED

AATYYCQHSREFPWTFGGGTKLEIKRADAAPGGGGSGGGGSGGGGSEVQLV

ESGGGLVKPGGSRKLSCAASGFTFSNYGMHWVRQAPEKGLEWVAYISSGSS

TIYYADTVKGRFTISRDNAKNTLFLQMTSLRSEDTAMYYCARRGLLLDYWG

QGTTLTVSSASTKGPSVFPLAPLESSGSDIVLTQSPASLAVSLGQRATISC

RASKSVSTSSYSYMHWYQQKPGQPPKLLIKYASYLESGVPARFSGSGSGTD

FTLNIHPVEEEDAATYYCQHSREFPWTFGGGTKLEIKRADAAPGGGGSGGG

GSGGGGSEVQLVESGGGLVKPGGSRKLSCAASGFTFSNYGMHWVRQAPEKG

LEWVAYISSGSSTIYYADTVKGRFTISRDNAKNTLFLQMTSLRSEDTAMYY

CARRGLLLDYWGQGTTLTVSSLEQKLISEEDLNSAVDHHHHHH.
```

Annotation of Tri-scFv Protein Domains with Reference to SEQ ID NO:40
  AGIH sequence increases solubility (amino acids 1-4 of SEQ ID NO:40)
  Vk variable region (amino acids 5-115 of SEQ ID NO:40)
  Initial (6 aa) of light chain CH1 (amino acids 116-121 of SEQ ID NO:40)
  (GGGGS)₃ (SEQ ID NO:37) linker (amino acids 122-136 of SEQ ID NO:40)
  VH variable region (amino acids 137-252 of SEQ ID NO:40)
  Linker between Fv fragments consisting of human IgG CH1 initial 13 amino acids (amino acids 253-265 of SEQ ID NO:40)
  Swivel sequence (amino acids 266-271 of SEQ ID NO:40)
  Vk variable region (amino acids 272-382 of SEQ ID NO:40)
  Initial (6 aa) of light chain CH1 (amino acids 383-388 of SEQ ID NO:40)
  (GGGGS)₃ (SEQ ID NO:37) linker (amino acids 389-403 of SEQ ID NO:40)
  VH variable region (amino acids 404-519 of SEQ ID NO:40)
  Linker between Fv fragments consisting of human IgG CH1 initial 13 amino acids (amino acids 520-532 of SEQ ID NO:40)
  Swivel sequence (amino acids 533-538 of SEQ ID NO:40)
  Vk variable region (amino acids 539-649 of SEQ ID NO:40)
  Initial (6 aa) of light chain CH1 (amino acids 650-655 of SEQ ID NO:40)
  (GGGGS)₃ (SEQ ID NO:37) linker (amino acids 656-670 of SEQ ID NO:40)
  VH variable region (amino acids 671-786 of SEQ ID NO:40)
  Myc tag (amino acids 787-802 of SEQ ID NO:40)
  His 6 tag (amino acids 803-808 of SEQ ID NO:40)

WO 2016/033321 and Noble, et al., *Cancer Research*, 75(11):2285-2291 (2015), show that di-scFv and tri-scFv have some improved and additional activities compared to their monovalent counterpart. The subsequences corresponding to the different domains of each of the exemplary fusion proteins are also provided above. One of skill in the art will appreciate that the exemplary fusion proteins, or domains thereof, can be utilized to construct fusion proteins discussed in more detail above. For example, in some embodiments, the di-scFv includes a first scFv including a Vk variable region (e.g., amino acids 5-115 of SEQ ID NO:39, or a functional variant or fragment thereof), linked to a VH variable domain (e.g., amino acids 137-252 of SEQ ID NO:39, or a functional variant or fragment thereof), linked to a second scFv including a Vk variable region (e.g., amino acids 272-382 of SEQ ID NO:39, or a functional variant or fragment thereof), linked to a VH variable domain (e.g., amino acids 404-519 of SEQ ID NO:39, or a functional variant or fragment thereof). In some embodiments, a tri-scFv includes a di-scFv linked to a third scFv domain including a Vk variable region (e.g., amino acids 539-649 of SEQ ID NO:40, or a functional variant or fragment thereof), linked to a VH variable domain (e.g., amino acids 671-786 of SEQ ID NO:40, or a functional variant or fragment thereof).

The Vk variable regions can be linked to VH variable domains by, for example, a linker (e.g., (GGGGS)₃ (SEQ ID NO:37), alone or in combination with a (6 aa) of light chain CH1 (amino acids 116-121 of SEQ ID NO:39). Other suitable linkers are discussed above and known in the art. scFv can be linked by a linker (e.g., human IgG CH1 initial 13 amino acids (253-265) of SEQ ID NO:39), alone or in combination with a swivel sequence (e.g., amino acids 266-271 of SEQ ID NO:39). Other suitable linkers are discussed above and known in the art.

Therefore, a di-scFv can include amino acids 5-519 of SEQ ID NO:39. A tri-scFv can include amino acids 5-786 of SEQ ID NO:40. In some embodiments, the fusion proteins include additional domains. For example, in some embodiments, the fusion proteins include sequences that enhance solubility (e.g., amino acids 1-4 of SEQ ID NO:39). Therefore, in some embodiments, a di-scFv can include amino acids 1-519 of SEQ ID NO:39. A tri-scFv can include amino acids 1-786 of SEQ ID NO:40. In some embodiments that fusion proteins include one or more domains that enhance purification, isolation, capture, identification, separation, etc., of the fusion protein. Exemplary domains include, for example, Myc tag (e.g., amino acids 520-535 of SEQ ID NO:39) and/or a His tag (e.g., amino acids 536-541 of SEQ ID NO:39). Therefore, in some embodiments, a di-scFv can include the amino acid sequence of SEQ ID NO:39. A tri-scFv can include the amino acid sequence of SEQ ID NO:40. Other substitutable domains and additional domains are discussed in more detail above.

An exemplary 3E10 humanized Fv sequence is discussed in WO 2016/033324:

```
                                          (SEQ ID NO: 41)
DIVLTQSPASLAVSPGQRATITCRASKSVSTSSYSYMHWYQQKPGQPPKLL

IYYASYLESGVPARFSGSGSGTDFTLTINPVEANDTANYYCQHSREFPWTF

GQGTKVEIKGGGGSGGGGSGGGGSEVQLVESGGGLVQPGGSLRLSCSASGF

TFSNYGMHWVRQAPGKGLEYVSYISSGSSTIYYADTVKGRFTISRDNSKNT

LYLQMSSLRAEDTAVYYCVKRGLLLDYWGQGTLVTVSS.
```

Exemplary 3E10 humanized di-scFv sequences are discussed in WO 2019/018426 and WO/2019/018428, and include:

```
(Variant 2, SEQ ID NO: 61)
DIQMTQSPSSLSASLGDRATITCRASKSVSTSSYSYMHWYQQKPGQPPKLL

IKYASYLESGVPSRFSGSGSGTDFTLTISSLQPEDAATYYCQHSREFPWTF
```

```
-continued
GGGTKVEIKRADAAPGGGGSGGGGSGGGGSEVQLVESGGGLVQPGGSLRLS
CAASGFTFSNYGMHWVRQAPGKGLEWVSYISSSSSTIYYADSVKGRFTISR
DNAKNSLYLQMNSLRAEDTAVYYCARRGLLLDYWGQGTTVTVSSASTKGPS
VFPLAPLESSGSDIQMTQSPSSLSASLGDRATITCRASKSVSTSSYSYMHW
YQQKPGQPPKLLIKYASYLESGVPSRFSGSGSGTDFTLTISSLQPEDAATY
YCQHSREFPWTFGGGTKVEIKRADAAPGGGGSGGGGSGGGGSEVQLVESGG
GLVQPGGSLRLSCAASGFTFSNYGMHWVRQAPEKGLEWVSYISSSSSTIYY
ADSVKGRFTISRDNAKNSLYLQMNSLRAEDTAVYYCARRGLLLDYWGQGTT
VTVSS, (Variant 3, SEQ ID NO: 62)
DIQMTQSPSSLSASLGDRATITCRASKSVSTSSYSYMHWYQQKPGQPPKLL
IKYASYLESGVPSRFSGSGSGTDFTLTISSLQPEDAATYYCQHSREFPWTF
GGGTKVEIKRADAAPGGGGSGGGGSGGGGSEVQLVESGGGVVQPGGSLRLS
CAASGFTFSNYGMHWVRQAPEKGLEWVSYISSSSSTIYYADSVKGRFTISR
DNSKNTLYLQMNSLRAEDTAVYYCARRGLLLDYWGQGTTVTVSSASTKGPS
VFPLAPLESSGSDIQMTQSPSSLSASLGDRATITCRASKSVSTSSYSYMHW
YQQKPGQPPKLLIKYASYLESGVPSRFSGSGSGTDFTLTISSLQPEDAATY
YCQHSREFPWTFGGGTKVEIKRADAAPGGGGSGGGGSGGGGSEVQLVESGG
GVVQPGGSLRLSCAASGFTFSNYGMHWVRQAPEKGLEWVSYISSSSSTIYY
ADSVKGRFTISRDNSKNTLYLQMNSLRAEDTAVYYCARRGLLLDYWGQGTT
VTVSS, (Variant 4, SEQ ID NO: 63)
DIQMTQSPSSLSASLGDRATITCRASKSVSTSSYSYMHWYQQKPGQPPKLL
IKYASYLESGVPSRFSGSGSGTDFTLTISSLQPEDAATYYCQHSREFPWTF
GGGTKVEIKRADAAPGGGGSGGGGSGGGGSEVQLVESGGGDVKPGGSLRLS
CAASGFTFSNYGMHWVRQAPEKGLEWVSYISSSSSTIYYADSVKGRFTISR
DNSKNTLYLQMNSLRAEDTAVYYCARRGLLLDYWGQGTTVTVSSASTKGPS
VFPLAPLESSGSDIQMTQSPSSLSASLGDRATITCRASKSVSTSSYSYMHW
YQQKPGQPPKLLIKYASYLESGVPSRFSGSGSGTDFTLTISSLQPEDAATY
YCQHSREFPWTFGGGTKVEIKRADAAPGGGGSGGGGSGGGGSEVQLVESGG
GDVKPGGSLRLSCAASGFTFSNYGMHWVRQAPEKGLEWVSYISSSSSTIYY
ADSVKGRFTISRDNSKNTLYLQMNSLRAEDTAVYYCARRGLLLDYWGQGTT
VTVSS, (Variant 6, SEQ ID NO: 64)
DIQMTQSPSSLSASLGDRATITCRASKSVSTSSYSYMHWYQQKPGQAPKLL
IKYASYLESGVPSRFSGSGSGTDFTLTISSLQPEDFATYYCQHSREFPWTF
GQGTKVEIKRADAAPGGGGSGGGGSGGGGSEVQLVESGGGLVQPGGSLRLS
CAASGFTFSNYGMHWVRQAPGKGLEWVSYISSSSSTIYYADSVKGRFTISR
DNAKNSLYLQMNSLRAEDTAVYYCARRGLLLDYWGQGTTVTVSSASTKGPS
VFPLAPLESSGSDIQMTQSPSSLSASLGDRATITCRASKSVSTSSYSYMHW
YQQKPGQAPKLLIKYASYLESGVPSRFSGSGSGTDFTLTISSLQPEDFATY
YCQHSREFPWTFGQGTKVEIKRADAAPGGGGSGGGGSGGGGSEVQLVESGG
GLVQPGGSLRLSCAASGFTFSNYGMHWVRQAPGKGLEWVSYISSSSSTIYY
ADSVKGRFTISRDNAKNSLYLQMNSLRAEDTAVYYCARRGLLLDYWGQGTT
VTVSS, (Variant 7, SEQ ID NO: 65)
DIQMTQSPSSLSASLGDRATITCRASKSVSTSSYSYMHWYQQKPGQAPKLL
IKYASYLESGVPSRFSGSGSGTDFTLTISSLQPEDFATYYCQHSREFPWTF
GQGTKVEIKRADAAPGGGGSGGGGSGGGGSEVQLVESGGGVVQPGGSLRLS
CAASGFTFSNYGMHWVRQAPEKGLEWVSYISSSSSTIYYADSVKGRFTISR
DNSKNTLYLQMNSLRAEDTAVYYCARRGLLLDYWGQGTTVTVSSASTKGPS
VFPLAPLESSGSDIQMTQSPSSLSASLGDRATITCRASKSVSTSSYSYMHW
YQQKPGQAPKLLIKYASYLESGVPSRFSGSGSGTDFTLTISSLQPEDFATY
YCQHSREFPWTFGQGTKVEIKRADAAPGGGGSGGGGSGGGGSEVQLVESGG
GVVQPGGSLRLSCAASGFTFSNYGMHWVRQAPEKGLEWVSYISSSSSTIYY
ADSVKGRFTISRDNSKNTLYLQMNSLRAEDTAVYYCARRGLLLDYWGQGTT
VTVSS, (Variant 8, SEQ ID NO: 66)
DIQMTQSPSSLSASLGDRATITCRASKSVSTSSYSYMHWYQQKPGQAPKLL
IKYASYLESGVPSRFSGSGSGTDFTLTISSLQPEDFATYYCQHSREFPWTF
GQGTKVEIKRADAAPGGGGSGGGGSGGGGSEVQLVESGGGDVKPGGSLRLS
CAASGFTFSNYGMHWVRQAPEKGLEWVSYISSSSSTIYYADSVKGRFTISR
DNSKNTLYLQMNSLRAEDTAVYYCARRGLLLDYWGQGTTVTVSSASTKGPS
VFPLAPLESSGSDIQMTQSPSSLSASLGDRATITCRASKSVSTSSYSYMHW
YQQKPGQAPKLLIKYASYLESGVPSRFSGSGSGTDFTLTISSLQPEDFATY
YCQHSREFPWTFGQGTKVEIKRADAAPGGGGSGGGGSGGGGSEVQLVESGG
GDVKPGGSLRLSCAASGFTFSNYGMHWVRQAPEKGLEWVSYISSSSSTIYY
ADSVKGRFTISRDNSKNTLYLQMNSLRAEDTAVYYCARRGLLLDYWGQGTT
VTVSS, (Variant 10, SEQ ID NO: 67)
DIQMTQSPSSLSASVGDRVTITCRASKSVSTSSYSYMHWYQQKPGKAPKLL
IKYASYLESGVPSRFSGSGSGTDFTLTISSLQPEDFATYYCQHSREFPWTF
GQGTKVEIKRADAAPGGGGSGGGGSGGGGSEVQLVESGGGLVQPGGSLRLS
CAASGFTFSNYGMHWVRQAPGKGLEWVSYISSSSSTIYYADSVKGRFTISR
DNAKNSLYLQMNSLRAEDTAVYYCARRGLLLDYWGQGTTVTVSSASTKGPS
VFPLAPLESSGSDIQMTQSPSSLSASVGDRVTITCRASKSVSTSSYSYMHW
YQQKPGKAPKLLIKYASYLESGVPSRFSGSGSGTDFTLTISSLQPEDFATY
YCQHSREFPWTFGQGTKVEIKRADAAPGGGGSGGGGSGGGGSEVQLVESGG
GLVQPGGSLRLSCAASGFTFSNYGMHWVRQAPGKGLEWVSYISSSSSTIYY
ADSVKGRFTISRDNAKNSLYLQMNSLRAEDTAVYYCARRGLLLDYWGQGTT
VTVSS, (Variant 11, SEQ ID NO: 68)
DIQMTQSPSSLSASVGDRVTITCRASKSVSTSSYSYMHWYQQKPGKAPKLL
IKYASYLESGVPSRFSGSGSGTDFTLTISSLQPEDFATYYCQHSREFPWTF
GQGTKVEIKRADAAPGGGGSGGGGSGGGGSEVQLVESGGGVVQPGGSLRLS
```

CAASGFTFSNYGMHWVRQAPEKGLEWVSYISSSSSTIYYADSVKGRFTISR
DNSKNTLYLQMNSLRAEDTAVYYCARRGLLLDYWGQGTTVTVSSASTKGPS
VFPLAPLESSGSDIQMTQSPSSLSASVGDRVTITCRASKSVSTSSYSYMHW
YQQKPGKAPKLLIKYASYLESGVPSRFSGSGSGTDFTLTISSLQPEDFATY
YCQHSREFPWTFGQGTKVEIKRADAAPGGGGSGGGGSGGGGSEVQLVESGG
GVVQPGGSLRLSCAASGFTFSNYGMHWVRQAPEKGLEWVSYISSSSSTIYY
ADSVKGRFTISRDNSKNTLYLQMNSLRAEDTAVYYCARRGLLLDYWGQGTT
VTVSS, (Variant 12, SEQ ID NO: 69)
DIQMTQSPSSLSASVGDRVTITCRASKSVSTSSYSYMHWYQQKPGKAPKLL
IKYASYLESGVPSRFSGSGSGTDFTLTISSLQPEDFATYYCQHSREFPWTF
GQGTKVEIKRADAAPGGGGSGGGGSGGGGSEVQLVESGGGDVKPGGSLRLS
CAASGFTFSNYGMHWVRQAPEKGLEWVSYISSSSSTIYYADSVKGRFTISR
DNSKNTLYLQMNSLRAEDTAVYYCARRGLLLDYWGQGTTVTVSSASTKGPS
VFPLAPLESSGSDIQMTQSPSSLSASVGDRVTITCRASKSVSTSSYSYMHW
YQQKPGKAPKLLIKYASYLESGVPSRFSGSGSGTDFTLTISSLQPEDFATY
YCQHSREFPWTFGQGTKVEIKRADAAPGGGGSGGGGSGGGGSEVQLVESGG
GDVKPGGSLRLSCAASGFTFSNYGMHWVRQAPEKGLEWVSYISSSSSTIYY
ADSVKGRFTISRDNSKNTLYLQMNSLRAEDTAVYYCARRGLLLDYWGQGTT
VTVSS, (Variant 13, SEQ ID NO: 70)
DIQMTQSPSSLSASLGDRATITCRASKTVSTSSYSYMHWYQQKPGQPPKLL
IKYASYLESGVPSRFSGSGSGTDFTLTISSLQPEDAATYYCQHSREFPWTF
GGGTKVEIKRADAAPGGGGSGGGGSGGGGSEVQLVESGGGLVQPGGSLRLS
CAASGFTFSNYGMHWVRQAPGKGLEWVSYISSGSSTIYYADSVKGRFTISR
DNAKNSLYLQMNSLRAEDTAVYYCARRGLLLDYWGQGTTVTVSSASTKGPS
VFPLAPLESSGSDIQMTQSPSSLSASLGDRATITCRASKTVSTSSYSYMHW
YQQKPGQPPKLLIKYASYLESGVPSRFSGSGSGTDFTLTISSLQPEDAATY
YCQHSREFPWTFGGGTKVEIKRADAAPGGGGSGGGGSGGGGSEVQLVESGG
GLVQPGGSLRLSCAASGFTFSNYGMHWVRQAPGKGLEWVSYISSGSSTIYY
ADSVKGRFTISRDNAKNSLYLQMNSLRAEDTAVYYCARRGLLLDYWGQGTT
VTVSS, (Variant 14, SEQ ID NO: 71)
DIQMTQSPSSLSASLGDRATITCRASKTVSTSSYSYMHWYQQKPGQPPKLL
IKYASYLESGVPSRFSGSGSGTDFTLTISSLQPEDAATYYCQHSREFPWTF
GGGTKVEIKRADAAPGGGGSGGGGSGGGGSEVQLVESGGGVVQPGGSLRLS
CAASGFTFSNYGMHWVRQAPEKGLEWVSYISSGSSTIYYADSVKGRFTISR
DNSKNTLYLQMNSLRAEDTAVYYCARRGLLLDYWGQGTTVTVSSASTKGPS
VFPLAPLESSGSDIQMTQSPSSLSASLGDRATITCRASKTVSTSSYSYMHW
YQQKPGQPPKLLIKYASYLESGVPSRFSGSGSGTDFTLTISSLQPEDAATY
YCQHSREFPWTFGGGTKVEIKRADAAPGGGGSGGGGSGGGGSEVQLVESGG
GVVQPGGSLRLSCAASGFTFSNYGMHWVRQAPEKGLEWVSYISSGSSTIYY
ADSVKGRFTISRDNSKNTLYLQMNSLRAEDTAVYYCARRGLLLDYWGQGTT
VTVSS, (Variant 15, SEQ ID NO: 72)
DIQMTQSPSSLSASLGDRATITCRASKTVSTSSYSYMHWYQQKPGQPPKLL
IKYASYLESGVPSRFSGSGSGTDFTLTISSLQPEDAATYYCQHSREFPWTF
GGGTKVEIKRADAAPGGGGSGGGGSGGGGSEVQLVESGGGDVKPGGSLRLS
CAASGFTFSNYGMHWVRQAPEKGLEWVSYISSGSSTIYYADSVKGRFTISR
DNSKNTLYLQMNSLRAEDTAVYYCARRGLLLDYWGQGTTVTVSSASTKGPS
VFPLAPLESSGSDIQMTQSPSSLSASLGDRATITCRASKTVSTSSYSYMHW
YQQKPGQPPKLLIKYASYLESGVPSRFSGSGSGTDFTLTISSLQPEDAATY
YCQHSREFPWTFGGGTKVEIKRADAAPGGGGSGGGGSGGGGSEVQLVESGG
GDVKPGGSLRLSCAASGFTFSNYGMHWVRQAPEKGLEWVSYISSGSSTIYY
ADSVKGRFTISRDNSKNTLYLQMNSLRAEDTAVYYCARRGLLLDYWGQGTT
VTVSS, (Variant 16, SEQ ID NO: 73)
DIQMTQSPSSLSASVGDRVTITCRASKTVSTSSYSYMHWYQQKPGKAPKLL
IKYASYLESGVPSRFSGSGSGTDFTLTISSLQPEDFATYYCQHSREFPWTF
GQGTKVEIKRADAAPGGGGSGGGGSGGGGSEVQLVESGGGLVQPGGSLRLS
CAASGFTFSNYGMHWVRQAPGKGLEWVSYISSGSSTIYYADSVKGRFTISR
DNAKNSLYLQMNSLRAEDTAVYYCARRGLLLDYWGQGTTVTVSSASTKGPS
VFPLAPLESSGSDIQMTQSPSSLSASVGDRVTITCRASKTVSTSSYSYMHW
YQQKPGKAPKLLIKYASYLESGVPSRFSGSGSGTDFTLTISSLQPEDFATY
YCQHSREFPWTFGQGTKVEIKRADAAPGGGGSGGGGSGGGGSEVQLVESGG
GLVQPGGSLRLSCAASGFTFSNYGMHWVRQAPGKGLEWVSYISSGSSTIYY
ADSVKGRFTISRDNAKNSLYLQMNSLRAEDTAVYYCARRGLLLDYWGQGTT
VTVSS, (Variant 17, SEQ ID NO: 74)
DIQMTQSPSSLSASVGDRVTITCRASKTVSTSSYSYMHWYQQKPGKAPKLL
IKYASYLESGVPSRFSGSGSGTDFTLTISSLQPEDFATYYCQHSREFPWTF
GQGTKVEIKRADAAPGGGGSGGGGSGGGGSEVQLVESGGGVVQPGGSLRLS
CAASGFTFSNYGMHWVRQAPEKGLEWVSYISSGSSTIYYADSVKGRFTISR
DNSKNTLYLQMNSLRAEDTAVYYCARRGLLLDYWGQGTTVTVSSASTKGPS
VFPLAPLESSGSDIQMTQSPSSLSASVGDRVTITCRASKTVSTSSYSYMHW
YQQKPGKAPKLLIKYASYLESGVPSRFSGSGSGTDFTLTISSLQPEDFATY
YCQHSREFPWTFGQGTKVEIKRADAAPGGGGSGGGGSGGGGSEVQLVESGG
GVVQPGGSLRLSCAASGFTFSNYGMHWVRQAPEKGLEWVSYISSGSSTIYY
ADSVKGRFTISRDNSKNTLYLQMNSLRAEDTAVYYCARRGLLLDYWGQGTT
VTVSS, (Variant 18, SEQ ID NO: 75)
DIQMTQSPSSLSASVGDRVTITCRASKTVSTSSYSYMHWYQQKPGKAPKLL

IKYASYLESGVPSRFSGSGSGTDFTLTISSLQPEDFATYYCQHSREFPWTF

GQGTKVEIKRADAAPGGGGSGGGGSGGGGSEVQLVESGGGDVKPGGSLRLS

CAASGFTFSNYGMHWVRQAPEKGLEWVSYISSGSSTIYYADSVKGRFTISR

DNSKNTLYLQMNSLRAEDTAVYYCARRGLLLDYWGQGTTVTVSSASTKGPS

VFPLAPLESSGSDIQMTQSPSSLSASVGDRVTITCRASKTVSTSSYSYMHW

YQQKPGKAPKLLIKYASYLESGVPSRFSGSGSGTDFTLTISSLQPEDFATY

YCQHSREFPWTFGQGTKVEIKRADAAPGGGGSGGGGSGGGGSEVQLVESGG

GDVKPGGSLRLSCAASGFTFSNYGMHWVRQAPEKGLEWVSYISSGSSTIYY

ADSVKGRFTISRDNSKNTLYLQMNSLRAEDTAVYYCARRGLLLDYWGQGTT

VTVSS,
and (Variant 19, SEQ ID NO: 76)
DIQMTQSPSSLSASLGDRATITCRASKTVSTSSYSYMHWYQQKPGQAPKLL

IKYASYLESGVPSRFSGSGSGTDFTLTISSLQPEDFATYYCQHSREFPWTF

GQGTKVEIKRADAAPGGGGSGGGGSGGGGSEVQLVESGGGLVQPGGSLRLS

CAASGFTFSNYGMHWVRQAPGKGLEWVSYISSGSSTIYYADSVKGRFTISR

DNAKNSLYLQMNSLRAEDTAVYYCARRGLLLDYWGQGTTVTVSSASTKGPS

VFPLAPLESSGSDIQMTQSPSSLSASLGDRATITCRASKTVSTSSYSYMHW

YQQKPGQAPKLLIKYASYLESGVPSRFSGSGSGTDFTLTISSLQPEDFATY

YCQHSREFPWTFGQGTKVEIKRADAAPGGGGSGGGGSGGGGSEVQLVESGG

GLVQPGGSLRLSCAASGFTFSNYGMHWVRQAPGKGLEWVSYISSGSSTIYY

ADSVKGRFTISRDNAKNSLYLQMNSLRAEDTAVYYCARRGLLLDYWGQGTT

VTVSS.

c. Additional Sequences

Additional sequences that may used in the construction of anti-DNA antigen binding proteins, antibodies, fragments and fusion proteins include, but are not limited to, (IgG1 L2345A/L235A heavy chain full length
sequence, SEQ ID NO: 77)
EVQLVESGGGLVQPGGSLRLSCAASGFTFSNYGMHWVRQAPGKGLEWVSYI

SSGSSTIYYADSVKGRFTISRDNAKNSLYLQMNSLRAEDTAVYYCARRGLL

LDYWGQGTTVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPEAAGGPSVFLFPPKPKDTLMISRT

PEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSK

LTVDKSRWQQGNVFSCSVMHEALHNHYTQKSLSLSPGK, (IgG1 constant heavy region 1, SEQ ID NO: 78)
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKV, (IgG1 hinge region, SEQ ID NO: 79)
EPKSCDKTHTCP, (IgG1 L2345A/L235A constant heavy region 2, SEQ ID
NO: 80)
PCPAPEAAGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALP

APIEKTISKAK, (IgG1 constant heavy region 3, SEQ ID NO: 81)
GQPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSLS

LSPGK, (IgG1 N297D heavy chain full length sequence, SEQ
ID NO: 82)
EVQLVESGGGLVQPGGSLRLSCAASGFTFSNYGMHWVRQAPGKGLEWVSYI

SSGSSTIYYADSVKGRFTISRDNAKNSLYLQMNSLRAEDTAVYYCARRGLL

LDYWGQGTTVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRT

PEVTCVVVDVSHEDPEVKFNWYVDGVEVHNAKTKPREEQYDSTYRVVSVLT

VLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSK

LTVDKSRWQQGNVFSCSVMHEALHNHYTQKSLSLSPGK, (IgG1 N297D constant heavy region 2, SEQ ID NO: 83)
PCPAPELLGGPSVFLFPPKPKDTLMISRTPEVTCVVVDVSHEDPEVKFNWY

VDGVEVHNAKTKPREEQYDSTYRVVSVLTVLHQDWLNGKEYKCKVSNKALP

APIEKTISKAK, (IgG1 L2345A/L235A/N297D heavy chain full length
sequence, SEQ ID NO: 84)
EVQLVESGGGLVQPGGSLRLSCAASGFTFSNYGMHWVRQAPGKGLEWVSYI

SSGSSTIYYADSVKGRFTISRDNAKNSLYLQMNSLRAEDTAVYYCARRGLL

LDYWGQGTTVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPEAAGGPSVFLFPPKPKDTLMISRT

PEVTCVVVDVSHEDPEVKFNWYVDGVEVHNAKTKPREEQYDSTYRVVSVLT

VLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSK

LTVDKSRWQQGNVFSCSVMHEALHNHYTQKSLSLSPGK, (IgG1 L2345A/L235A/N297D constant heavy region 2,
SEQ ID NO: 85)
PCPAPEAAGGPSVFLFPPKPKDTLMISRTPEVTCVVVDVSHEDPEVKFNWY

VDGVEVHNAKTKPREEQYDSTYRVVSVLTVLHQDWLNGKEYKCKVSNKALP

APIEKTISKAK, (SEQ ID NO: 86, Unmodified constant heavy region 2)
PCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALP

APIEKTISKAK,

-continued and (Light chain full length sequence, SEQ ID NO: 87)
DIQMTQSPSSLSASLGDRATITCRASKTVSTSSYSYMHWYQQKPGQPPKLL

IKYASYLESGVPSRFSGSGSGTDFTLTISSLQPEDAATYYCQHSREFPWTF

GGGTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQG

LSSPVTKSFNRGEC.

B. Cargo

As used in the methods provided herein, the 3E10 is typically contacted with cells in complex with a nucleic acid cargo. The interaction between the antibody or binding protein and the nucleic acid cargo is non-covalent.

The nucleic acid cargo can be single stranded or double stranded. The nucleic acid cargo can be or include DNA, RNA, nucleic acid analogs, or a combination thereof. As discussed in more detail below, nucleic acid analogs can be modified at the base moiety, sugar moiety, or phosphate backbone. Such modification can improve, for example, stability, hybridization, or solubility of the nucleic acid.

The nucleic acid cargo is typically functional in the sense that is or encodes an agent that is biologically active once delivered into cells. Exemplary cargo is discussed in more detail below, but includes, for example, mRNA or DNA encoding polypeptides of interest including, for example expression constructs and vectors, inhibitory nucleic acids such as siRNA, or nucleic acid encoding the inhibitory nucleic acid including, for example expression constructs and vectors.

The disclosed compositions can include a plurality of a single nucleic acid cargo molecule. In some embodiments, the compositions include a plurality of a multiplicity (e.g., 2, 3, 4, 5, 6, 7, 8, 9 10, or more) of different nucleic acid molecules.

In some embodiments, the cargo molecules are 0.001, 0.01, 1, 10's 100's, 1,000's, 10,000's, and/or 100,000's of kilobases in length.

In some embodiments, e.g., the cargo may be between 0.001 kb and 100 kb, or between 0.001 kb kb and 50 kb, or between 0.001 kb kb and 25 kb, or between 0.001 kb and 12.5 kb, or between 0.001 kb and 10 kb, or between 0.001 kb and 8 kb, or 0.001 kb and 5 kb, or between 0.001 kb and 2.5 kb, or between 0.001 kb and 1 kb, or between 0.01 kb and 100 kb, or between 0.01 kb kb and 50 kb, or between 0.01 kb kb and 25 kb, or between 0.01 kb and 12.5 kb, or between 0.01 kb and 10 kb, or between 0.01 kb and 8 kb, or 0.01 kb and 5 kb, or between 0.01 kb and 2.5 kb, or between 0.01 kb and 1 kb, or between 0.1 kb and 100 kb, or between 0.1 kb kb and 50 kb, or between 0.1 kb kb and 25 kb, or between 0.1 kb and 12.5 kb, or between 0.1 kb and 10 kb, or between 0.1 kb and 8 kb, or 0.1 kb and 5 kb, or between 0.1 kb and 2.5 kb, or between 0.1 kb and 1 kb, or between 1 kb and 100 kb, or between 1 kb kb and 50 kb, or between 1 kb kb and 25 kb, or between 1 kb and 12.5 kb, or between 1 kb and 10 kb, or between 1 kb and 8 kb, or 1 kb and 5 kb, or between 1 kb and 2.5 kb, each inclusive.

In some embodiments, e.g., the cargo may be between 0.2 kb and 10 kb, or between 0.2 kb and 5 kb, or between 0.2 kb and 2.5 kb, or between 0.2 kb and 1 kb, or between 0.2 kb and 0.5 kb, or between 0.5 kb and 0.25 kb, or between 0.5 kb and 10 kb, or between 0.5 kb and 5 kb, or between 1 kb and 5 kb, or between 1 kb and 3 kb, or between 2 kb and 10 kb, or between 3 kb and 5 kb.

It will be appreciated that for specific application the nucleic acid cargo may be one or more discrete lengths that, for example, falls within one of the foregoing ranges (inclusive), the specific values for each are expressly disclosed. For example, the size can be as small as a single nucleotide or nucleobase. In an exemplary application the cargo is a cyclic dinucleotide like cGAMP, which is a STING agonist. In other embodiments, the cargo is a short oligomer. For example, oligomers as short as 8-mers can be used for anti-sense or splice switching. Slightly longer ones (e.g., 18 to 20 mers) can be used for gene editing.

1. Forms of the Cargo

The nucleic acid cargo is a nucleic acid and can be an isolated nucleic acid composition. As used herein, "isolated nucleic acid" refers to a nucleic acid that is separated from other nucleic acid molecules that are present in a mammalian genome, including nucleic acids that normally flank one or both sides of the nucleic acid in a mammalian genome. The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

The nucleic acid sequences encoding polypeptides include genomic sequences. Also disclosed are mRNA/cDNA sequence wherein the exons have been deleted. Other nucleic acid sequences encoding polypeptides, such polypeptides that include the above-identified amino acid sequences and fragments and variants thereof, are also disclosed. Nucleic acids encoding polypeptides may be optimized for expression in the expression host of choice. Codons may be substituted with alternative codons encoding the same amino acid to account for differences in codon usage between the organism from which the nucleic acid sequence is derived and the expression host. In this manner, the nucleic acids may be synthesized using expression host-preferred codons.

Nucleic acids can be in sense or antisense orientation, or can be, for example, complementary to a reference sequence encoding a polypeptide.

a. Vectors

The cargo can be a vector, for example, a vector encoding a polypeptide(s) and/or functional nucleic acid(s). Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. For example, the control sequence can be incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids, cosmids, and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, WI), Clontech (Palo Alto, CA), Stratagene (La Jolla, CA), and Invitrogen Life Technologies (Carlsbad, CA).

In some embodiments, the cargo is delivered into the cell and remains extrachromosomal. In some embodiments, the cargo is introduced into a host cell and is integrated into the host cell's genome. As discussed in more detail below, the compositions can be used in methods of gene therapy. Methods of gene therapy can include the introduction into the cell of a polynucleotide that alters the genotype of the cell. Introduction of the polynucleotide can correct, replace, or otherwise alter the endogenous gene via genetic recombination. Methods can include introduction of an entire replacement copy of a defective gene, a heterologous gene, or a small nucleic acid molecule such as an oligonucleotide. For example, a corrective gene can be introduced into a non-specific location within the host's genome.

In some embodiments, the cargo is a vector. Methods to construct expression vectors containing genetic sequences and appropriate transcriptional and translational control elements are well known in the art. These methods include in vitro recombinant DNA techniques, synthetic techniques, and in vivo genetic recombination. Expression vectors generally contain regulatory sequences and necessary elements for the translation and/or transcription of the inserted coding sequence, which can be, for example, the polynucleotide of interest. The coding sequence can be operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

For example, in some embodiments, a polynucleotide of interest is operably linked to a promoter or other regulatory elements known in the art. Thus, the cargo can be a vector such as an expression vector. The engineering of polynucleotides for expression in a prokaryotic or eukaryotic system may be performed by techniques generally known to those of skill in recombinant expression. An expression vector typically includes one of the disclosed compositions under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein or functional nucleic acid. This is the meaning of "recombinant expression" in the context used here.

Many standard techniques are available to construct expression vectors containing the appropriate nucleic acids and transcriptional/translational control sequences in order to achieve protein or peptide or functional nucleic acid expression in a variety of host-expression systems.

Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the disclosed compositions. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

b. mRNAs

The cargo can be mRNA.

Chemical structures with the ability to promote stability and/or translation efficiency may also be used. For example, the RNA can have 5' and 3' UTRs. The length of the 3' UTR can, for example, exceed 100 nucleotides. In some embodiments the 3' UTR sequence is between 100 and 5000 nucleotides. In some embodiments, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following delivery of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In some embodiments, the 5' UTR contains the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

In some embodiments, the mRNA has a cap on the 5' end, a 3' poly(A) tail, or a combination thereof which determine ribosome binding, initiation of translation and stability mRNA in the cell.

5'caps provide stability to RNA molecules. The 5' cap may, for example, be $m^7G(5')ppp(5')G$, $m^7G(5')ppp(5')A$, $G(5')ppp(5')G$ or $G(5')ppp(5')A$ cap analogs, which are all commercially available. The 5' cap can also be an anti-reverse-cap-analog (ARCA) (Stepinski, et al., *RNA*, 7:1468-95 (2001)) or any other suitable analog. The 5' cap can be incorporated using techniques known in the art (Cougot, et al., *Trends in Biochem. Sci.*, 29:436-444 (2001); Stepinski, et al., *RNA*, 7:1468-95 (2001); Elango, et al., *Biochim. Biophys. Res. Commun.*, 330:958-966 (2005)).

The RNAs can also contain an internal ribosome entry site (IRES) sequence. The IRES sequence may be any viral, chromosomal or artificially designed sequence which initiates cap-independent ribosome binding to mRNA and facilitates the initiation of translation.

Generally, the length of a poly(A) tail positively correlates with the stability of the transcribed RNA. In one embodiment, the poly(A) tail is between 100 and 5000 adenosines.

A polyA segment can be produced during PCR by using a reverse primer containing a polyT tail, such as 100T tail (size can be, e.g., 50-5000 T), or after PCR by any other method, including, but not limited to, DNA ligation or in vitro recombination. Poly(A) tails also provide stability to RNAs and reduce their degradation. Poly(A) tails of RNAs can additionally or alternatively be extended following in vitro transcription with the use of a poly(A) polymerase, such as *E. coli* polyA polymerase (E-PAP).

Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. Suitable ATP analogs include, but are not limited to, cordiocipin and 8-azaadenosine.

2. Sequence of the Cargo a. Polypeptide of Interest

The cargo can encode one or more proteins. The cargo can be a polynucleotide that can be monocistronic or polycistronic. In some embodiments, polynucleotide is multigenic. The polynucleotide can be, for example, an mRNA or a expression construct such as a vector.

The cargo can encode one or more polypeptides of interest. The polypeptide can be any polypeptide. For example, the polypeptide encoded by the polynucleotide can be a polypeptide that provides a therapeutic or prophylactic effect to an organism or that can be used to diagnose a disease or disorder in an organism. For example, for treatment of cancer, autoimmune disorders, parasitic, viral, bacterial, fungal or other infections, the polynucleotide(s) to be expressed may encode a polypeptide that functions as a ligand or receptor for cells of the immune system, or can function to stimulate or inhibit the immune system of an organism.

In some embodiments, the polynucleotide supplements or replaces a polynucleotide that is defective in the organism.

In particular embodiments, the polynucleotide encodes dystrophin, utrophin, or a combination thereof. Such compositions may be administered in an effective amount to treat a subject from a dystrophy, particularly a muscular dystrophy, for example, Duchenne's muscular dystrophy.

In another particular embodiment, the polynucleotide encodes antigen, e.g., an antigen that can be utilized in a vaccine formulation and associated methods. In a particular embodiment, polynucleotide encodes a viral antigen(s), for example, a SARS-CoV-2 antigen(s). Thus, compositions and methods of use thereof for protection against, and the treatment of, SARS-CoV-2 virus and viral infections and disease associate therewith including COVID19 are provided.

In some embodiments, the polynucleotide includes a selectable marker, for example, a selectable marker that is effective in a eukaryotic cell, such as a drug resistance selection marker. This selectable marker gene can encode a factor necessary for the survival or growth of transformed host cells grown in a selective culture medium. Typical selection genes encode proteins that confer resistance to antibiotics or other toxins, e.g., ampicillin, neomycin, methotrexate, kanamycin, gentamycin, Zeocin, or tetracycline, complement auxotrophic deficiencies, or supply critical nutrients withheld from the media.

In some embodiments, the polynucleotide includes a reporter gene. Reporter genes are typically genes that are not present or expressed in the host cell. The reporter gene typically encodes a protein which provides for some phenotypic change or enzymatic property. Examples of such genes are provided in Weising et al. *Ann. Rev. Genetics,* 22, 421 (1988). Preferred reporter genes include glucuronidase (GUS) gene and GFP genes.

b. Functional Nucleic Acids

The cargo can be or encode a functional nucleic acid. Functional nucleic acids are nucleic acid molecules that have a specific function, such as binding a target molecule or catalyzing a specific reaction. As discussed in more detail below, functional nucleic acid molecules can be divided into the following non-limiting categories: antisense molecules, siRNA, miRNA, aptamers, ribozymes, RNAi, and external guide sequences, and cyclic dinucleotides. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the polypeptide itself. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Therefore the compositions can include one or more functional nucleic acids designed to reduce expression of a gene, or a gene product thereof. For example, the functional nucleic acid or polypeptide can be designed to target and reduce or inhibit expression or translation of an mRNA; or to reduce or inhibit expression, reduce activity, or increase degradation of a protein. In some embodiments, the composition includes a vector suitable for in vivo expression of the functional nucleic acid.

i. Antisense

The functional nucleic acids can be or encode antisense molecules. Antisense molecules are designed to interact with a target nucleic acid molecule through either canonical or non-canonical base pairing. The interaction of the antisense molecule and the target molecule is designed to promote the destruction of the target molecule through, for example, RNAse H mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

ii. RNA Interference

In some embodiments, the functional nucleic acids induce gene silencing through RNA interference. Gene expression can also be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404: 293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, a siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs.

Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Texas), ChemGenes (Ashland, Massachusetts), Dharmacon (Lafayette, Colorado), Glen Research (Sterling, Virginia), MWB Biotech (Esbersberg, Germany), Proligo (Boulder, Colorado), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors having shRNA are available, such as, for example, Imgenex's GENESUPPRESSOR™ Construction Kits and Invitrogen's BLOCK-IT™ inducible RNAi plasmid and lentivirus vectors.

In some embodiment, the functional nucleic acid is siRNA, shRNA, miRNA. In some embodiments, the composition includes a vector expressing the functional nucleic acid.

iii. Aptamers

The functional nucleic acids can be or encode an aptamer. Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a molecule such as a polypeptide, that the background molecule be a different polypeptide.

iv. Ribozymes

The functional nucleic acids can be or encode ribozymes. Ribozymes are nucleic acid molecules that are capable of catalyzing a chemical reaction, either intramolecularly or intermolecularly. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

v. External Guide Sequences

The functional nucleic acids can be or encode external guide sequences. External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells. Representative examples of how to make and use EGS molecules to facilitate cleavage of a variety of different target molecules are known in the art.

Methods of making and using vectors for in vivo expression of functional nucleic acids such as antisense oligonucleotides, siRNA, shRNA, miRNA, EGSs, ribozymes, and aptamers are known in the art.

vi. Cyclic Dinucleotides

The functional nucleic acids can be or encode a cyclic dinucleotide. Cyclic dinucleotides bind directly to the STING adaptor protein, resulting in production of IFN-β (Zhang, et al., Mol Cell., 51(2):226-35 (2013). doi: 10.1016/j.molcel.2013.05.022.). Several canonical and noncanonical dinucleotides are known in the art, and include, but are not limited to, 2'3'-cGAMP, 2'3'-cGAMP, 3'3'-cGAMP, c-di-AMP, c-di-GMP, cAIMP (CL592), cAIMP Difluor (CL614), cAIM(PS)2 Difluor (Rp/Sp) (CL656), 2'2'-cGAMP, 2'3'-cGAM(PS)2 (Rp/Sp), 3'3'-cGAMP Fluorinated, c-di-AMP Fluorinated, 2'3'-c-di-AMP, 2'3'-c-di-AM(PS)2 (Rp,Rp), 2'3'-c-di-AM(PS)2 (Rp,Rp), c-di-GMP Fluorinated, 2'3'-c-di-GMP, c-di-IMP, DMXAA.

vii. Immunostimulatory Oligonucleotides

In some embodiments, the functional nucleic acids can be or encode an oligonucleotide ligand. Examples include, but are not limited to, pattern recognition receptors (PRRs) ligands.

Examples of PRRs include the Toll-like family of signaling molecules that play a role in the initiation of innate immune responses and also influence the later and more antigen specific adaptive immune responses. Therefore, the oligonucleotide can serve as a ligand for a Toll-like family signaling molecule, such as Toll-Like Receptor 9 (TLR9).

For example, unmethylated CpG sites can be detected by TLR9 on plasmacytoid dendritic cells and B cells in humans (Zaida, et al., *Infection and Immunity*, 76(5):2123-2129, (2008)). Therefore, the sequence of oligonucleotide can include one or more unmethylated cytosine-guanine (CG or CpG, used interchangeably) dinucleotide motifs. The 'p' refers to the phosphodiester backbone of DNA, however, in some embodiments, oligonucleotides including CG can have a modified backbone, for example a phosphorothioate (PS) backbone.

In some embodiments, an oligonucleotide can contain more than one CG dinucleotide, arranged either contiguously or separated by intervening nucleotide(s). The CpG motif(s) can be in the interior of the oligonucleotide sequence. Numerous nucleotide sequences stimulate TLR9 with variations in the number and location of CG dinucleotide(s), as well as the precise base sequences flanking the CG dimers.

Typically, CG ODNs are classified based on their sequence, secondary structures, and effect on human peripheral blood mononuclear cells (PBMCs). The five classes are Class A (Type D), Class B (Type K), Class C, Class P, and Class S (Vollmer, J & Krieg, A M, *Advanced drug delivery reviews* 61(3): 195-204 (2009), incorporated herein by reference). CG ODNs can stimulate the production of Type I interferons (e.g., IFNα) and induce the maturation of dendritic cells (DCs). Some classes of ODNs are also strong activators of natural killer (NK) cells through indirect cytokine signaling. Some classes are strong stimulators of human B cell and monocyte maturation (Weiner, G L, PNAS USA 94(20): 10833-7 (1997); Dalpke, A H, *Immunology* 106(1): 102-12 (2002); Hartmann, G, *J of Immun.* 164(3): 1617-2 (2000), each of which is incorporated herein by reference).

Other PRR Toll-like receptors include TLR3, and TLR7 which may recognize double-stranded RNA, single-stranded and short double-stranded RNAs, respectively, and retinoic acid-inducible gene I (RIG-I)-like receptors, namely RIG-I and melanoma differentiation-associated gene 5 (MDA5), which are best known as RNA-sensing receptors in the cytosol.

RIG-I (retinoic-acid-inducible protein 1, also known as Ddx58) and MDA-5 (melanoma-differentiation-associated gene 5, also known as Ifih1 or Helicard) are cytoplasmic RNA helicases that belong to the RIG-I-like receptors (RLRs) family and are critical for host antiviral responses.

RIG-I and MDA-5 sense double-stranded RNA (dsRNA), a replication intermediate for RNA viruses, and signal through the mitochondrial antiviral signaling protein MAVS (also known as IPS-1, VISA or Cardif), leading to production of type-I interferons (IFN-α and IFN-β).

RIG-I detects viral RNA that exhibit an uncapped 5'-di/triphosphate end and a short blunt-ended double stranded portion, two essential features facilitating discrimination from self-RNAs. The features of MDA-5 physiological ligands have not been fully characterized yet. However, it is admitted that RIG-I and MDA-5 exhibit a different dependency for the length of dsRNAs: RIG-I selectively binds short dsRNA while MDA-5 selectively binds long dsRNA. Consistent with this, RIG-I and MDA-5 bind Poly(I:C), a synthetic dsRNA analog, with different length predilection.

Under some circumstances, RIG-I can also sense dsDNA indirectly. Viral dsDNA can be transcribed by the RNA polymerase III into dsRNA with a 5'-triphosphate moiety. Poly(dA:dT), a synthetic analog of B-form DNA, thus constitutes another RIG-I ligand.

Exemplary RIG-I ligands include, but are not limited to, 5'ppp-dsRNA, a specific agonist of RIG-I; 3p-hpRNA, a specific agonist of RIG-I; Poly(I:C)/LyoVec complexes that are recognized by RIG-I and/or MDA-5 depending of the size of poly(I:C); Poly(dA:dT)/LyoVec complexes that are indirectly recognized by RIG-I.

In some embodiments, the oligonucleotide contains a functional ligand for TLR3, TLR7, TLR8, TLR9, or RIG-I-like receptors, or combinations thereof.

Examples of immunostimulatory oligonucleotides, and methods of making them are known in the art and commercially available, see for example, Bodera, P. *Recent Pat Inflamm Allergy Drug Discov.* 5(1):87-93 (2011), incorporated herein by reference.

3. Composition of the Cargo

The disclosed nucleic acid cargo can be or include DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides include uracil, thymine, cytosine, adenine and guanine as the heterocyclic bases, and ribose or deoxyribose sugar linked by phosphodiester bonds.

In some embodiments, the cargo includes or is composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein "modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In some embodiments, the analogs have a substantially uncharged, phosphorus containing backbone.

a. Heterocyclic Bases

The principal naturally-occurring nucleotides include uracil, thymine, cytosine, adenine and guanine as the heterocyclic bases. The cargo can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-.beta.-D-ribofuranosyl)pyridine (2-aminopyridine), and various pyrrolo- and pyrazolopyrimidine derivatives.

b. Sugar Modifications

Cargo can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-0,4'-C-methylene (LNA), 2'-O-(methoxyethyl) (2'-OME) and 2'-O—(N-(methyl) acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or dexyribose and also forms a bridge with the i−1 phosphate in the purine strand of the duplex.

In some embodiments, the nucleic acid is a morpholino oligonucleotide. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation.

In some embodiments, oligonucleotides employ morpholino-based subunits bearing base-pairing moieties, joined by uncharged linkages, as described above.

c. Internucleotide Linkages

Oligonucleotides are connected by an internucleotide bond that refers to a chemical linkage between two nucleoside moieties. Modifications to the phosphate backbone of DNA or RNA oligonucleotides may increase the binding affinity or stability oligonucleotides, or reduce the susceptibility of oligonucleotides nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, E. P. et al., *Organic. Chem.*, 52:4202, (1987)), and uncharged morpholino-based polymers having achiral intersubunit linkages (see, e.g., U.S. Pat. No. 5,034,506), as discussed above. Some internucleotide linkage analogs include morpholidate, acetal, and polyamide-linked heterocycles.

In another embodiment, the cargo are composed of locked nucleic acids. Locked nucleic acids (LNA) are modified RNA nucleotides (see, for example, Braasch, et al., *Chem. Biol.*, 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the cargo are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are composed of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as 0-linkers), amino acids such as lysine are particularly useful if positive charges are desired in the PNA, and the like. Methods for the chemical assembly of PNAs are well known. See, for example, U.S. Pat. Nos. 5,539,082, 5,527, 675, 5,623,049, 5,714,331, 5,736,336, 5,773,571 and 5,786, 571.

Cargo optionally include one or more terminal residues or modifications at either or both termini to increase stability, and/or affinity of the oligonucleotide for its target. Commonly used positively charged moieties include the amino acids lysine and arginine, although other positively charged moieties may also be useful. Cargo may further be modified to be end capped to prevent degradation using a propylamine group. Procedures for 3' or 5' capping oligonucleotides are well known in the art.

In some embodiments, the nucleic acid can be single stranded or double stranded.

C. Pharmaceutical Compositions

The compositions can be used therapeutically in combination with a pharmaceutically acceptable carrier.

The compositions including nucleic acid cargo complexed with 3E10 antibody are preferably employed for therapeutic uses in combination with a suitable pharmaceutical carrier. Such compositions include an effective amount of the composition, and a pharmaceutically acceptable carrier or excipient.

The compositions may be in a formulation for administration topically, locally or systemically in a suitable pharmaceutical carrier. Remington's Pharmaceutical Sciences, 15th Edition by E. W. Martin (Mark Publishing Company, 1975), discloses typical carriers and methods of preparation. The complexes may also be encapsulated in suitable biocompatible particles formed of biodegradable or non-biodegradable polymers or proteins or liposomes for targeting to cells. Such systems are well known to those skilled in the art. In some embodiments, the complexes are encapsulated in nanoparticles.

Formulations for injection may be presented in unit dosage form, e.g., in ampules or in multi-dose containers, optionally with an added preservative. The compositions may take such forms as sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, *arachis* oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, and electrolyte replenishers (such as those based on Ringer's dextrose). The materials may be in solution, emulsions, or suspension (for example, incorporated into particles, liposomes, or cells). Typically, an appropriate amount of a pharmaceutically-acceptable salt is used in the formulation to render the formulation isotonic. Trehalose, typically in the amount of 1-5%, may be added to the pharmaceutical compositions. The pH of the solution is preferably from about 5 to about 8, and more preferably from about 7 to about 7.5.

Pharmaceutical compositions may include carriers, thickeners, diluents, buffers, preservatives, and surface-active agents. Carrier formulation can be found in Remington's Pharmaceutical Sciences, Mack Publishing Co., Easton, Pa. Those of skill in the art can readily determine the various parameters for preparing and formulating the compositions without resort to undue experimentation.

The compositions alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and air. For administration by inhalation, the compounds are delivered in the form of an aerosol spray presentation from pressurized packs or a nebulizer, with the use of a suitable propellant.

In some embodiments, the include pharmaceutically acceptable carriers with formulation ingredients such as salts, carriers, buffering agents, emulsifiers, diluents, excipients, chelating agents, preservatives, solubilizers, or stabilizers.

The nucleic acids may be conjugated to lipophilic groups like cholesterol and lauric and lithocholic acid derivatives with C32 functionality to improve cellular uptake. For example, cholesterol has been demonstrated to enhance uptake and serum stability of siRNA in vitro (Lorenz, et al., *Bioorg. Med. Chem. Lett.*, 14(19):4975-4977 (2004)) and in vivo (Soutschek, et al., *Nature*, 432(7014):173-178 (2004)). In addition, it has been shown that binding of steroid conjugated oligonucleotides to different lipoproteins in the bloodstream, such as LDL, protect integrity and facilitate biodistribution (Rump, et al., *Biochem. Pharmacol.*, 59(11): 1407-1416 (2000)). Other groups that can be attached or conjugated to the nucleic acids described above to increase cellular uptake, include acridine derivatives; cross-linkers such as psoralen derivatives, azidophenacyl, proflavin, and azidoproflavin; artificial endonucleases; metal complexes such as EDTA-Fe(II) and porphyrin-Fe(II); alkylating moieties; nucleases such as alkaline phosphatase; terminal transferases; abzymes; cholesteryl moieties; lipophilic carriers; peptide conjugates; long chain alcohols; phosphate esters; radioactive markers; non-radioactive markers; carbohydrates; and polylysine or other polyamines. U.S. Pat. No. 6,919,208 to Levy, et al., also describes methods for enhanced delivery. These pharmaceutical formulations may be manufactured in a manner that is itself known, e.g., by means of conventional mixing, dissolving, granulating, levigating, emulsifying, encapsulating, entrapping or lyophilizing processes.

Further carriers include sustained release preparations such as semi-permeable matrices of solid hydrophobic polymers containing the complexes, which matrices are in the form of shaped particles, e.g., films, liposomes or microparticles. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems. Inhalation includes administering the composition with an aerosol in an inhaler, either alone or attached to a carrier that can be absorbed. For systemic administration, it may be preferred that the composition is encapsulated in liposomes.

The compositions may be delivered in a manner which enables tissue-specific uptake of the agent and/or nucleotide delivery system, using invasive devices such as vascular or urinary catheters, and using interventional devices such as stents having drug delivery capability and configured as expansive devices or stent grafts.

The formulations may be delivered using a bioerodible implant by way of diffusion or by degradation of the polymeric matrix. In certain embodiments, the administration of the formulation may be designed to result in sequential exposures to the composition, over a certain time period, for example, hours, days, weeks, months or years. This may be accomplished, for example, by repeated administrations of a formulation or by a sustained or controlled release delivery system in which the compositions are delivered over a prolonged period without repeated administrations.

Other delivery systems suitable include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include non-polymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulations containing the complexes.

Complexes include nucleic acid cargo and antibody, and compositions thereof can be formulated for pulmonary or mucosal administration. The administration can include delivery of the composition to the lungs, nasal, oral (sublingual, buccal), vaginal, or rectal mucosa. The term aerosol as used herein refers to any preparation of a fine mist of particles, which can be in solution or a suspension, whether or not it is produced using a propellant. Aerosols can be produced using standard techniques, such as ultrasonication or high-pressure treatment.

For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers.

The complexes can be delivered to the target cells using a particle delivery vehicle. Nanoparticles generally refers to particles in the range of between 500 nm to less than 0.5 nm, preferably having a diameter that is between 50 and 500 nm, more preferably having a diameter that is between 50 and 300 nm. Cellular internalization of polymeric particles is highly dependent upon their size, with nanoparticulate polymeric particles being internalized by cells with much higher efficiency than micoparticulate polymeric particles. For example, Desai, et al. have demonstrated that about 2.5 times more nanoparticles that are 100 nm in diameter are taken up by cultured Caco-2 cells as compared to microparticles having a diameter on 1 M (Desai, et al., *Pharm. Res.*, 14:1568-73 (1997)). Nanoparticles also have a greater ability to diffuse deeper into tissues in vivo.

In some embodiments, the delivery vehicle is a dendrimer.

Examples of preferred biodegradable polymers include synthetic polymers that degrade by hydrolysis such as poly(hydroxy acids), such as polymers and copolymers of lactic acid and glycolic acid, other degradable polyesters, polyanhydrides, poly(ortho)esters, polyesters, polyurethanes, poly(butic acid), poly(valeric acid), poly(caprolactone), poly(hydroxyalkanoates), poly(lactide-co-caprolactone), and poly(amine-co-ester) polymers, such as those described in Zhou, et al., *Nature Materials*, 11:82-90 (2012) and WO 2013/082529, U.S. Published Application No. 2014/0342003, and PCT/US2015/061375.

In some embodiments, particularly those for targeting T cell in vivo, for example, for in vivo production of CAR T cells, immune cell or T cell markers such as CD3, CD7, or CD8, or markers of a target tissue such as the liver, can be targeted. For example, anti-CD8 antibodies and anti-CD3 Fab fragments have both been used to target T cells in vivo (Pfeiffer, et al., *EMBO Mol Med.*, 10(11) (2018). pii: e9158. doi: 10.15252/emmm.201809158., Smith, et al., *Nat Nanotechnol.*, 12(8):813-820 (2017). doi: 10.1038/nnano.2017.57). Thus, in some embodiments, the particle or other delivery vehicle includes a targeting moiety specific for CD3, CD7, CD8, or another immune cell (e.g., T cell) marker, or a marker for a specific tissue such as the thymus, spleen, or liver. The binding moiety can be, for example, an antibody or antigen binding fragment thereof.

Targeting moieties can be associated with, linked, conjugated, or otherwise attached directly or indirectly to a nanoparticle or other delivery vehicle thereof. Targeting molecules can be proteins, peptides, nucleic acid molecules, saccharides or polysaccharides that bind to a receptor or other molecule on the surface of a targeted cell. The degree of specificity and the avidity of binding to the graft can be modulated through the selection of the targeting molecule.

Examples of moieties include, for example, targeting moieties which provide for the delivery of molecules to specific cells, e.g., antibodies to hematopoietic stem cells, CD34+ cells, T cells or any other preferred cell type, as well as receptor and ligands expressed on the preferred cell type. Preferably, the moieties target hematopoeitic stem cells. Examples of molecules targeting extracellular matrix ("ECM") include glycosaminoglycan ("GAG") and collagen. In one embodiment, the external surface of polymer particles may be modified to enhance the ability of the particles to interact with selected cells or tissue. The method described above wherein an adaptor element conjugated to a targeting molecule is inserted into the particle is preferred. However, in another embodiment, the outer surface of a polymer micro- or nanoparticle having a carboxy terminus may be linked to targeting molecules that have a free amine terminus.

Other useful ligands attached to polymeric micro- and nanoparticles include pathogen-associated molecular patterns (PAMPs). PAMPs target Toll-like Receptors (TLRs) on the surface of the cells or tissue, or signal the cells or tissue internally, thereby potentially increasing uptake. PAMPs conjugated to the particle surface or co-encapsulated may include: unmethylated CpG DNA (bacterial), double-stranded RNA (viral), lipopolysacharide (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

In another embodiment, the outer surface of the particle may be treated using a mannose amine, thereby mannosylating the outer surface of the particle. This treatment may cause the particle to bind to the target cell or tissue at a mannose receptor on the antigen presenting cell surface. Alternatively, surface conjugation with an immunoglobulin molecule containing an Fc portion (targeting Fc receptor), heat shock protein moiety (HSP receptor), phosphatidylserine (scavenger receptors), and lipopolysaccharide (LPS) are additional receptor targets on cells or tissue.

Lectins that can be covalently attached to micro- and nanoparticles to render them target specific to the mucin and mucosal cell layer.

The choice of targeting moiety will depend on the method of administration of the nanoparticle composition and the cells or tissues to be targeted. The targeting molecule may generally increase the binding affinity of the particles for cell or tissues or may target the nanoparticle to a particular tissue in an organ or a particular cell type in a tissue. In some embodiments, the targeting moiety targets the thymus, spleen, or cancer cells The covalent attachment of any of the natural components of mucin in either pure or partially purified form to the particles would decrease the surface tension of the bead-gut interface and increase the solubility of the bead in the mucin layer. The attachment of polyamino acids containing extra pendant carboxylic acid side groups, e.g., polyaspartic acid and polyglutamic acid, increases bioadhesiveness. Using polyamino acids in the 15,000 to 50,000 kDa molecular weight range yields chains of 120 to 425 amino acid residues attached to the surface of the particles. The polyamino chains increase bioadhesion by means of chain entanglement in mucin strands as well as by increased carboxylic charge.

III. Methods of Use

Methods for using 3E10 to enhance delivery of nucleic acid constructs are provided. Typically an effective amount of 3E10 antibody is first contacted with a nucleic acid cargo whose delivery into cells is desired. For example, the nucleic acid cargo and antibody can be mixed in solution for sufficient time for the nucleic acid cargo and antibody to form complexes. Next, the mixture is contacted with cells. In other embodiments, the cargo and antibody are added to a solution containing or otherwise bathing cells, and the complexes are formed in the presence of the cells. The complexes can be contacted with cells in vitro, ex vivo, or in vivo. Thus, in some embodiments, the solution of complexes is added to the cells in culture or injected into an animal to be treated.

It is believed that the antibody helps deliver the nucleic acid into cell nuclei, and then alters the function of the RAD51 pathway which can promote gene editing by the donor DNA. The approach has no sequence limitations to the design of the nucleic acid cargo. The treatment can be, for example, administration of a mixture of an antibody and nucleic acid cargo to a subject in need thereof by simple IV administration The compositions and methods can include 1, 2, 3, 4, 5, 6, 7, 8, 9, 10, or more different nucleic acid constructs formed of RNA, DNA, PNA or other modified nucleic acids, or a combination thereof.

The effective amount or therapeutically effective amount of the composition can be a dosage sufficient to treat, inhibit, or alleviate one or more symptoms of a disease or disorder, or to otherwise provide a desired pharmacologic and/or physiologic effect, for example, reducing, inhibiting, or reversing one or more of the pathophysiological mechanisms underlying a disease or disorder.

An effective amount may also be an amount effective to increase the rate, quantity, and/or quality of delivery of the nucleic acid cargo relative to administration of the cargo in the absence of the antibody. The formulation of the composition is made to suit the mode of administration. Pharmaceutically acceptable carriers are determined in part by the particular composition being administered, as well as by the particular method used to administer the composition. Accordingly, there is a wide variety of suitable formulations of pharmaceutical compositions containing the complexes. The precise dosage will vary according to a variety of factors such as subject-dependent variables (e.g., age, immune system health, clinical symptoms etc.).

The composition can be administered or otherwise contacted with target cells once, twice, or three times daily; one, two, three, four, five, six, seven times a week, one, two, three, four, five, six, seven or eight times a month. For example, in some embodiments, the composition is administered every two or three days, or on average about 2 to about 4 times about week. Thus, in some embodiments, the composition is administered as part of dosage regimen including two or more separate treatments.

Dosage regimens include maintenance regimens, where the dosage remains the same between two or more administrations, escalation regimens where the dosage increases between two or more administrations, de-escalation regimens, where the dosage decreases between two or more administrations, or a combination thereof.

In some embodiments, the first dose can be a low dose. Dose escalation can be continued until a satisfactory biochemical or clinical response is reached. The clinical response will depend on the disease or disorder being treated, and/or the desired outcome. In some embodiments the dosage may increase until a therapeutic effect is identified, preferably without also inducing undesired toxicity or an acceptably high amount thereof. Next, the dosages can be maintained or steadily reduced to a maintenance dose. The methods can used to standardize, optimize, or customize the dose level, dose frequency, or duration of the therapy.

Generally, prior to administration, particularly for in vivo administration, antibody and nucleic acid are mixed for a period of time at room temperature. In some embodiments, time of complexation ranges from, for example, 1 minute to 30 minutes, or 10 minutes to 20, each inclusive, with a preferred complexation time of about 15 minutes. Antibody dose can range from 0.0001 mg to 1 mg, each inclusive, with a preferred dose of about 0.1 mg. Nucleic acid dose can range from 0.001 µg to 100 µg, inclusive, with a preferred dose of 10 µg. The in vivo data below (e.g., FIG. 6B) was produced using 0.1 mg 3E10, 10 µg of mRNA, and complexed for 15 minutes.

The Examples below may indicate that DNA cargo may be delivered more generally to multiple tissues and not restricted to tumors, while RNA delivery may be more selective for tumor tissue. Thus, in some embodiments, RNA cargo (e.g., alone) may be selectively delivered to cancer cells or other tumor tissues. In some embodiments, when wider distribution of RNA cargo is desired, the RNA may be mixed with DNA (e.g., carrier DNA) to facilitate delivery to non-cancer/tumor tissues. Carrier DNA can be, for example, plasmid DNA or low molecular weight, from e.g., salmon sperm. In some embodiments, carrier DNA is non-coding DNA. Carrier DNA can be single stranded or double stranded or a combination thereof. In some embodiments, carrier DNA is composed of nucleic acids having 1-10, 1-100, 1-1,000, or 1-10,000 nucleotides in length, or any subrange or integer thereof, or combination thereof. Typically carrier DNA is not conjugated or otherwise covalently attached to the antibody. Typically carrier DNA is co-incubated with cargo nucleic acid (e.g., RNA) and antibody, and co-delivered as a complex therewith. In some embodiments, the carrier DNA is non-coding DNA.

A. In Vitro and Ex Vivo Methods

For in vitro and ex vivo methods, cells are typically contacted with the composition while in culture. For ex vivo methods, cells may be isolated from a subject and contacted ex vivo with the composition to produce cells containing the cargo nucleic acid(s). In a preferred embodiment, the cells are isolated from the subject to be treated or from a syngenic host. Target cells can be removed from a subject prior to contacting with composition.

B. In Vivo Methods

In some embodiments, in vivo delivery of nucleic acid cargo to cells is used for gene editing and/or treatment of a disease or disorder in a subject. The composition, typically including antibody-nucleic acid cargo, can be administered directly to a subject for in vivo therapy.

In general, methods of administering compounds, including antibodies, oligonucleotides and related molecules, are well known in the art. In particular, the routes of administration already in use for nucleic acid therapeutics, along with formulations in current use, provide preferred routes of administration and formulation for the donor oligonucleotides described above. Preferably the composition is injected or infused into the animal.

The compositions can be administered by a number of routes including, but not limited to, intravenous, intraperitoneal, intraamniotic, intramuscular, subcutaneous, or topical (sublingual, rectal, intranasal, pulmonary, rectal mucosa, and vaginal), and oral (sublingual, buccal).

In some embodiments, the composition is formulated for pulmonary delivery, such as intranasal administration or oral inhalation. Administration of the formulations may be accomplished by any acceptable method that allows the complexes to reach their targets. The administration may be localized (i.e., to a particular region, physiological system, tissue, organ, or cell type) or systemic, depending on the condition being treated. Compositions and methods for in vivo delivery are also discussed in WO 2017/143042.

The methods can also include administering an effective amount of the antibody-nucleic acid complex composition to an embryo or fetus, or the pregnant mother thereof, in vivo. In some methods, compositions are delivered in utero by injecting and/or infusing the compositions into a vein or artery, such as the vitelline vein or the umbilical vein, or into the amniotic sac of an embryo or fetus. See, e.g., Ricciardi, et al., Nat Commun. 2018 Jun. 26; 9(1):2481. doi: 10.1038/s41467-018-04894-2, and WO 2018/187493.

C. Applications

Nucleic acid cargo, e.g., mRNA, functional nucleic acid, DNA expression constructs, vectors, etc., encoding a polypeptide of interest or functional nucleic acid, can be delivered into cells using a 3E10 antibody, for expression of, or inhibition of, a polypeptide in the cells. The compositions and methods can be used over a range of different applications. Non-limiting examples include CRISPR and gRNA expression vectors+/−editing DNAs, delivery of large DNAs (plasmids and expression vectors), gene replacement and gene therapy, delivery of DNAs and/or RNAs to, for example, generate CAR-T cells in vivo or ex vivo and to simplify CAR-T cell production in vivo or ex vivo, delivery of siRNAs, delivery of mRNAs, etc. Exemplary applications related to gene therapy/gene editing and immunomodulation, particularly chimeric antigen receptor T cell production, are discussed below.

1. Gene Therapy and Editing

In some embodiments, the compositions are used for gene editing.

For example, the methods can be especially useful to treat genetic deficiencies, disorders and diseases caused by mutations in single genes, for example, to correct genetic deficiencies, disorders and diseases caused by point mutations. If the target gene contains a mutation that is the cause of a genetic disorder, then the methods can be used for mutagenic repair that may restore the DNA sequence of the target gene to normal. The target sequence can be within the coding DNA sequence of the gene or within an intron. The target sequence can also be within DNA sequences that regulate expression of the target gene, including promoter or enhancer sequences.

In the methods herein, cells that have been contacted with the complexes may be administered to a subject. The subject may have a disease or disorder such as hemophilia, muscular dystrophy, globinopathies, cystic fibrosis, xeroderma pigmentosum, or lysosomal storage diseases. In such embodiments, gene modification, gene replacement, gene addition, or a combination thereof, may occur in an effective amount to reduce one or more symptoms of the disease or disorder in the subject.

In some embodiments, the DNA cargo includes a nucleic acid encoding a nuclease, a donor oligonucleotide or nucleic acid encoding a donor oligonucleotide, or a combination thereof.

a. Gene Editing Nuclease

Nucleic acid cargos include those that encode an element or elements that induce a single or a double strand break in the target cell's genome, and optionally, but preferable in combination with other elements such as donor oligonucleotides and/or, particularly in the case of CRISPR/Cas, other elements of the system such as gRNA. The compositions can be used, for example, to reduce or otherwise modify expression of a target gene.

i. Strand Break Inducing Elements CRISPR/Cas

In some embodiments, the nucleic acid cargo includes one or more elements of a CRISPR/Cas-mediated genome editing composition, a nucleic acid encoding one or more elements of a CRISPR/Cas-mediated genome editing composition, or a combination thereof. As used herein, CRISPR/Cas-mediated genome editing composition refers to the elements of a CRISPR system needed to carry out CRISPR/Cas-mediated genome editing in a mammalian subject. As discussed in more detail below, CRISPR/Cas-mediated genome editing compositions typically include one or more nucleic acids encoding a crRNA, a tracrRNA (or chimeric thereof also referred to a guide RNA or single guide RNA) and a Cas enzyme, such as Cas9. The CRISPR/Cas-mediated genome editing composition can optionally include a donor polynucleotide that can be recombined into the target cell's genome at or adjacent to the target site (e.g., the site of single or double stand break induced by the Cas9).

The CRISPR/Cas system has been adapted for use as gene editing (silencing, enhancing or changing specific genes) for use in eukaryotes (see, for example, Cong, *Science,* 15:339 (6121):819-823 (2013) and Jinek, et al., *Science,* 337(6096): 816-21 (2012)). By transfecting a cell with the required elements including a cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423, which are specifically incorporated by reference herein in their entireties.

The methods of delivery disclosed herein are suitable for use with numerous variations on the CRISPR/Cas system.

In general, "CRISPR system" refers collectively to transcripts and other elements involved in the expression of or directing the activity of CRISPR-associated ("Cas") genes, including sequences encoding a Cas gene, a tracr (transactivating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

As discussed in more detail below, in some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, *Science,* 15:339(6121):819-823 (2013) and Jinek, et al., *Science,* 337(6096):816-21 (2012)). A single fused crRNA-tracrRNA construct is also referred to herein as a guide RNA or gRNA (or single-guide RNA (sgRNA)). Within an sgRNA, the crRNA portion can be identified as the 'target sequence' and the tracrRNA is often referred to as the 'scaffold'.

In some embodiments, one or more elements of a CRISPR system is derived from a type I, type II, or type III CRISPR system. In some embodiments, one or more elements of a CRISPR system is derived from a particular organism including an endogenous CRISPR system, such as *Streptococcus pyogenes*.

In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence can be any polynucleotide, such as DNA or RNA polynucleotides. In some embodiments, a target sequence is located in the nucleus or cytoplasm of a cell.

In the target nucleic acid, each protospacer is associated with a protospacer adjacent motif (PAM) whose recognition is specific to individual CRISPR systems. In the *Streptococcus pyogenes* CRISPR/Cas system, the PAM is the nucleotide sequence NGG. In the *Streptococcus thermophiles* CRISPR/Cas system, the PAM is the nucleotide sequence is NNAGAAW. The tracrRNA duplex directs Cas to the DNA target consisting of the protospacer and the requisite PAM via heteroduplex formation between the spacer region of the crRNA and the protospacer DNA.

Typically, in the context of an endogenous CRISPR system, formation of a CRISPR complex (including a guide sequence hybridized to a target sequence and complexed with one or more Cas proteins) results in cleavage of one or both strands in or near (e.g., within 1, 2, 3, 4, 5, 6, 7, 8, 9, 10, 20, 50, or more base pairs from) the target sequence. All or a portion of the tracr sequence may also form part of a CRISPR complex, such as by hybridization to all or a portion of a tracr mate sequence that is operably linked to the guide sequence.

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr/, a tool designed to help scientists find CRISPR targeting sites in a wide range of species and generate the appropriate crRNA sequence.

In some embodiments, one or more vectors driving expression of one or more elements of a CRISPR system are introduced into a target cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element can be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector includes one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors. In some embodiments, a vector includes an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector includes two or more insertion sites, each insertion site being located between two tracr mate sequences so as to allow insertion of a guide sequence at each site. In such an arrangement, the two or more guide sequences can include two or more copies of a single guide sequence, two or more different guide sequences, or combinations of these. When multiple different guide sequences are used, a single expression construct may be used to target CRISPR activity to multiple different, corresponding target sequences within a cell. For example, a single vector can include about or more than about 1, 2, 3, 4, 5, 6, 7, 8, 9, 10, 15, 20 guide sequences. In some embodiments, about or more than about 1, 2, 3, 4, 5, 6, 7, 8, 9, 10, such guide-sequence-containing vectors may be provided, and optionally delivered to a cell.

In some embodiments, a vector includes a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence.

In some embodiments, a vector encodes a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III) can be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%>, 1%>, 0.1%>, 0.01%, or lower with respect to its non-mutated form.

In some embodiments, an enzyme coding sequence encoding a CRISPR enzyme is codon optimized for expression in particular cells, such as eukaryotic cells. The eukaryotic cells can be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules.

The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al., *Nucl. Acids Res.*, 28:292 (2000). Computer algorithms for codon optimizing a particular sequence for expression in a particular host cell, for example Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme including one or more nuclear localization sequences (NLSs). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus.

In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors.

Detection of accumulation in the nucleus may be performed by any suitable technique. For example, a detectable marker may be fused to the CRISPR enzyme, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g., assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

In some embodiments, one or more of the elements of CRISPR system are under the control of an inducible promoter, which can include inducible Cas, such as Cas9.

Cong, *Science*, 15:339(6121):819-823 (2013) reported heterologous expression of Cas9, tracrRNA, pre-crRNA (or Cas9 and sgRNA) can achieve targeted cleavage of mammalian chromosomes. Therefore, CRISPR system utilized in the methods disclosed herein, and thus the cargo nucleic acid, be a vector system which can include one or more vectors encoding elements of the CRISPR system which can include a first regulatory element operably linked to a CRISPR/Cas system chimeric RNA (chiRNA) polynucleotide sequence, wherein the polynucleotide sequence includes (a) a guide sequence capable of hybridizing to a target sequence in a eukaryotic cell, (b) a tracr mate sequence, and (c) a tracr sequence; and a second regulatory element operably linked to an enzyme-coding sequence encoding a CRISPR enzyme which can optionally include at least one or more nuclear localization sequences. Elements (a), (b) and (c) can arranged in a 5' to 3 orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex can include the CRISPR enzyme complexed with (1) the guide sequence that is hybridized to the target sequence, and (2) the tracr mate sequence that is hybridized to the tracr sequence, wherein the enzyme coding sequence encoding the CRISPR enzyme further encodes a heterologous functional domain. In some embodiments, one or more of the vectors also encodes a suitable Cas enzyme, for example, Cas9. The different genetic elements can be under the control of the same or different promoters.

While the specifics can be varied in different engineered CRISPR systems, the overall methodology is similar. A practitioner interested in using CRISPR technology to target a DNA sequence (identified using one of the many available online tools) can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

ii. Zinc Finger Nucleases

In some embodiments, the element that induces a single or a double strand break in the target cell's genome is a nucleic acid construct or constructs encoding a zinc finger nucleases (ZFNs). Thus, the nucleic acid cargo can encode a ZFN.

ZFNs are typically fusion proteins that include a DNA-binding domain derived from a zinc-finger protein linked to a cleavage domain. The most common cleavage domain is the Type IIS enzyme Fok1. Fok1 catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. *Proc., Natl. Acad. Sci. USA* 89 (1992):4275-4279; Li et al. *Proc. Natl. Acad. Sci. USA*, 90:2764-2768 (1993); Kim et al. *Proc. Natl. Acad. Sci. USA.* 91:883-887 (1994a); Kim et al. *J. Biol. Chem.* 269:31, 978-31, 982 (1994b). One or more of these enzymes (or enzymatically functional fragments thereof) can be used as a source of cleavage domains.

The DNA-binding domain, which can, in principle, be designed to target any genomic location of interest, can be a tandem array of $Cys_2His_2$ zinc fingers, each of which generally recognizes three to four nucleotides in the target DNA sequence. The $Cys_2His_2$ domain has a general structure: Phe (sometimes Tyr)-Cys-(2 to 4 amino acids)-Cys-(3 amino acids)-Phe(sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

Engineering methods include, but are not limited to, rational design and various types of empirical selection methods. Rational design includes, for example, using databases including triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Published Application Nos. 2002/0165356; 2004/0197892; 2007/0154989; 2007/0213269; and International Patent Application Publication Nos. WO 98/53059 and WO 2003/016496.

iii. Transcription Activator-Like Effector Nucleases

In some embodiments, the element that induces a single or a double strand break in the target cell's genome is a nucleic acid construct or constructs encoding a transcription activator-like effector nuclease (TALEN). Thus, the nucleic acid cargo can encode a TALEN.

TALENs have an overall architecture similar to that of ZFNs, with the main difference that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer) and appear to have less stringent requirements than ZFNs for the length of the spacer between binding sites. Monomeric and dimeric TALENs can include more than 10, more than 14, more than 20, or more than 24 repeats.

Methods of engineering TAL to bind to specific nucleic acids are described in Cermak, et al, *Nucl. Acids Res.* 1-11 (2011). US Published Application No. 2011/0145940, which discloses TAL effectors and methods of using them to modify DNA. Miller et al. Nature Biotechnol 29: 143 (2011) reported making TALENs for site-specific nuclease architecture by linking TAL truncation variants to the catalytic domain of Fok1 nuclease. The resulting TALENs were shown to induce gene modification in immortalized human cells. General design principles for TALE binding domains can be found in, for example, WO 2011/072246.

b. Donor Polynucleotides

The nuclease activity of the genome editing systems described herein cleave target DNA to produce single or double strand breaks in the target DNA. Double strand breaks can be repaired by the cell in one of two ways: non-homologous end joining, and homology-directed repair. In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair (HDR), a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site.

Therefore, in some embodiments, the nucleic acid cargo is or includes a donor polynucleotide. The modifications of the target DNA due to NHEJ and/or homology-directed repair can be used to induce gene correction, gene replacement, gene tagging, transgene insertion, nucleotide deletion, gene disruption, gene mutation, etc.

Accordingly, cleavage of DNA by the genome editing composition can be used to delete nucleic acid material from a target DNA sequence by cleaving the target DNA sequence and allowing the cell to repair the sequence in the absence of an exogenously provided donor polynucleotide. Alternatively, if the genome editing composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, the compositions can be used to modify DNA in a site-specific, i.e., "targeted", way, for example gene knock-out, gene knock-in, gene editing, gene tagging, etc. as used in, for example, gene therapy.

In applications in which it is desirable to insert a polynucleotide sequence into a target DNA sequence, a polynucleotide including a donor sequence to be inserted is also provided to the cell. By a "donor sequence" or "donor polynucleotide" or "donor oligonucleotide" it is meant a nucleic acid sequence to be inserted at the cleavage site. The donor polynucleotide typically contains sufficient homology to a genomic sequence at the cleavage site, e.g., 70%, 80%, 85%, 90%, 95%, or 100% homology with the nucleotide sequences flanking the cleavage site, e.g., within about 50 bases or less of the cleavage site, e.g., within about 30 bases, within about 15 bases, within about 10 bases, within about 5 bases, or immediately flanking the cleavage site, to support homology-directed repair between it and the genomic sequence to which it bears homology. The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence includes a non-homologous sequence flanked by two regions of homology, such that homology-directed repair between the target DNA region and the two flanking sequences results in insertion of the non-homologous sequence at the target region.

2. Immunomodulation a. CAR T Cells

The disclosed compositions and methods are particularly useful in the context of preparing lymphocytes expressing immune receptors, particularly chimeric immune receptors (CIR) such as chimeric antigen receptors (CAR). Artificial immune receptors (also known and referred to herein, as chimeric T cell receptors, chimeric immunoreceptors, chimeric antigen receptors (CARs), and chimeric immune receptors (CIR)) are engineered receptors, which graft a selected specificity onto a cell. Cells modified according to the discussed methods can be utilized, as discussed in more detail below, in a variety of immune therapies for treatment of cancers, infections, inflammation, and autoimmune diseases.

In particularly preferred embodiments, mRNA or DNA encoding a chimeric antigen receptor cargo is delivered to immune cells, such as lymphocytes.

The cargo can be delivered to immune cells in vivo, ex vivo, or in vitro. In preferred embodiments, the cargo is mRNA, which may allow for one or more of reduced cost, ease of manufacturing, reduced side effects (e.g., cytokine storm, neurotoxicity, graft vs. host diseases, etc.). In a particular embodiments, immune cells (e.g., T cells) are harvested from a subject in need of CAR T cell therapy, the compositions and methods disclosed herein are used to deliver mRNA encoding one or more CAR T cell constructs into the harvested cells, and the cells are returned to the subject. In some embodiments, the process, from initially harvesting the cells to returning them to the subject, takes 1 week or less, for example, 1, 2, 3, 4, 5, 6, or 7 days. In particular embodiments, the process, from initially harvesting the cells to returning them to subject is carried in out in 1 or 2 days, or in less than 1 days, e.g., 1, 2, 3, 4, 5, 6, 7, 8, 9, 10, 11, 12, 13, 14, 15, 16, 17, 18, 19, 20, 21, 22, or 23 hours.

Strategies for the design and development of chimeric antigen receptors are reviewed in Dotti, et al., *Immunol Rev.* 2014 January; 257(1):. doi:10.1111/imr.12131 (35 pages), which is a specifically incorporated by reference herein in its entirety, as well as Dotti, *Molecular Therapy*, 22(5):899-890 (2014), Karlsson, et al., *Cancer Gene Therapy*, 20:386-93 (2013), Charo, et al., *Cancer Res.*, 65(5):2001-8 (2005), Jensen, et al., *Immunol Rev.*, 257(1): 127-144 (2014), Eaton, et al., *Gene Therapy*, 9:527-35 (2002), Barrett, et al., *Annu Rev Med.*, 65: 333-347 (2014), Cartellieri, et al., *Journal of Biomedicine and Biotechnology*, Volume 2010, Article ID 956304, 13 pages doi:10.1155/2010/956304; and U.S. Published Application Nos. 2015/0017120, 2015/0283178, 2015/0290244, 2014/0050709, and 2013/0071414.

CARs combine the antigen-binding property of monoclonal antibodies with the lytic capacity and self-renewal of T cells and have several advantages over conventional T cells (Ramos and Dotti, *Expert Opin Biol Ther.*, 11:855-873 (2011), Curran, et al., *J Gene Med.*, 14:405-415 (2012), Maher, *ISRN Oncol.* 2012:278093 (2012)). CAR-T cells recognize and kill cancer cells independently of the major histocompatibility complex (MHC). Thus target cell recognition is unaffected by some of the mechanisms by which tumors evade MHC-restricted T-cell recognition, for example downregulation of human leukocyte antigen (HLA) class I molecules and defective antigen processing.

Chimeric immune receptors were initially developed in the 1980s and originally included the variable (antigen binding) regions of a monoclonal antibody and the constant regions of the T-cell receptor (TCR) α and β chains (Kuwana, et al., *Biochem Biophys Res Commun.*, 149:960-968 (1987)). In 1993 this design was modified to include an ectodomain, from a single chain variable fragment (scFv) from the antigen binding regions of both heavy and light chains of a monoclonal antibody, a transmembrane domain, and an endodomain with a signaling domain derived from CD3-ζLater CARs have generally followed a similar structural design, with a costimulatory signaling endodomain. Accordingly, the CAR constructs utilized in the methods herein can include an antigen binding domain or ectodomain, a hinge domain, a transmembrane domain, an endodomain, and combinations thereof.

In some embodiments the ectodomain is an scFv. The affinity of the scFv predicts CAR function (Hudecek, et al., *Clin Cancer Res.*, 19(12):3153-64 (2013), Chmielewski, et al., *J Immunol.*, 173:7647-7653 (2004)). Antigen binding and subsequent activation can also be modified by adding a flexible linker sequence in the CAR, which allows for expression of two distinct scFvs that can recognize two different antigens (Grada, et al., *Mol Ther Nucleic Acids*, 2:e105 (2013)) (referred to as tandem CARs (TanCARs)). Tandem CARS may be more effective in killing cancers expressing low levels of each antigen individually and may also reduce the risk of tumor immune escape due by single antigen loss variants. Other ectodomains include IL13Rα2 (Kahlon, et al., *Cancer Res.*, 64:9160-9166 (2004), Brown, et al., *Clin Cancer Res.*, 18(8):2199-209 (2012), Kong, et al., *Clin Cancer Res.*, 18:5949-5960 (2012), NKG2D-ligand and CD70 receptor, peptide ligands (e.g., TIE peptide ligand), and so-called "universal ectodomains" (e.g., avidin ectodomain designed to recognize targets that have been contacted with biotinylated monoclonal antibodies, or FITC-specific scFv designed to recognize targets that have been contacted with FITC-labeled monoclonal antibodies (Zhang, et al., *Blood*, 106:1544-1551 (2005), Barber, et al., *Exp Hematol.*, 36:1318-1328 (2008), Shaffer, et al., Blood, 117:4304-4314 (2011), Davies, et al., *Mol Med.*, 18:565-576 (2012), Urbanska, et al., *Cancer Res.*, 72:1844-1852 (2012), Tamada, et al., *Clin Cancer Res.*, 18:6436-6445 (2012)).

In some embodiments, the CAR includes a hinge region. While the ectodomain is important for CAR specificity, the sequence connecting the ectodomain to the transmembrane domain (the hinge region) can also influence CAR-T-cell function by producing differences in the length and flexibility of the CAR. Hinges can include, for example, a CH2CH3 hinge, or a fragment thereof, derived from an immunoglobulin such as IgG1. For example, Hudecek et al. (Hudecek, et al., *Clin Cancer Res.*, 19(12):3153-64 (2013)) compared the influence of a CH2-CH3 hinge [229 amino acids (AA)], CH3 hinge (119 AA), and short hinge (12 AA) on the effector function of T cells expressing 3rd generation ROR1-specific CARs and found that T cells expressing 'short hinge' CARs had superior antitumor activity, while other investigators found that a CH2-CH3 hinge impaired epitope recognition of a 1st generation CD30-specific CAR (Hombach, et al., *Gene Ther.*, 7:1067-1075 (2000)).

Between the hinge (or ectodomain if no hinge domain) and the signaling endodomains typically lies a transmembrane domain, most typically derived from CD3-ζ, CD4, CD8, or CD28 molecules. Like hinges, the transmembrane domain can also influence CAR-T-cell effector function.

Upon antigen recognition, CAR endodomains transmit activation and costimulatory signals to T cells. T-cell activation relies on the phosphorylation of immunoreceptor tyrosine-based activation motifs (ITAMs) present in the cytoplasmic domain to the cytoplasmic CD3-(domain of the TCR complex (Irving, et al., *Cell*, 64:891-901 (1991)). Although the majority of CAR endomains contain an activation domain derived from CD3-ζ, others can include ITAM-containing domains such as the Fc receptor for IgE-γ domain (Haynes, et al., *J Immunol.*, 166:182-187 (2001)).

The target specificity of the cell expressing a CAR is determined by the antigen recognized by the antibody/ectodomain. The disclosed compositions and methods can be used to create constructs, and cells expressing the constructs, that target any antigen. In the context of immunotherapy, particularly cancer immunotherapy, numerous antigens, and suitable ectodomains for targeting them, are well known. Unlike the native TCR, the majority of scFv-based CARs recognize target antigens expressed on the cell surface rather than internal antigens that are processed and presented by the cells' MHC, however, CARs have the advantage over the classical TCR that they can recognize structures other than protein epitopes, including carbohydrates and glycolipids Dotti, et al., *Immunol Rev.* 2014 January; 257(1):. doi:10.1111/imr.12131 (35 pages) thus increasing the pool of potential target antigens. Preferred targets include antigens that are only expressed on cancer cells or their surrounding stroma (Cheever, et al., *Clin Cancer Res.,* 15:5323-5337 (2009)), such as the splice variant of EGFR (EGFRvIII), which is specific to glioma cells (Sampson, et al., *Semin Immunol.,* 20(5):267-75 (2008)). However, human antigens meet this requirement, and the majority of target antigens are expressed either at low levels on normal cells (e.g. GD2, CAIX, HER2) and/or in a lineage restricted fashion (e.g. CD19, CD20).

Preferred targets, and CARs that target them are known in the art (see, e.g., Dotti, et al., *Immunol Rev.* 2014 January; 257(1):. doi:10.1111/imr.12131 (35 pages). For example, CAR targets for hematological malignancies include, but are not limited to, CD 19 (e.g., B-cell) (Savoldo, et al., *J Clin Invest.,* 121:1822-1826 (2011), Cooper, et al., *Blood,* 105: 1622-1631 (2005); Jensen, et al., *Biol Blood Marrow Transplant* (2010), Kochenderfer, et al., *Blood,* 119:2709-2720 (2012), Brentjens, et al., *Molecular Therapy,* 17:5157 (2009), Brentjens, et al., *Nat Med.,* 9:279-286 (2003), Brentjens, et al., *Blood,* 118:4817-4828 (2011), Porter, et al., *N Engl J Med.,* 365:725-733 (2011), Kalos, et al., *Sci Transl Med.,* 3:95ra73 (2011), Brentjens, et al., *Sci Transl Med.,* 5:177ra38 (2013), Grupp, et al., *N Engl J Med* (2013)); CD20 (e.g., B-cell) (Jensen, et al., *Biol Blood Marrow Transplant* (2010), Till, et al., *Blood,* 112:2261-2271 (2008), Wang, et al., *Hum Gene Ther.,* 18:712-725 (2007), Wang, et al., *Mol Ther.,* 9:577-586 (2004), Jensen, et al., *Biol Blood Marrow Transplant,* 4:75-83 (1998)); CD22 (e.g., B-cell) (Haso, et al., *Blood,* 121:1165-1174 (2013)); CD30 (e.g., B-cell) (Di Stasi, et al., *Blood,* 113:6392-6402 (2009), Savoldo, et al., *Blood,* 110:2620-2630 (2007), Hombach, et al., *Cancer Res.,* 58:1116-1119 (1998)); CD33 (e.g., Myeloid) (Finney, et al., *JImmunol.,* 161:2791-2797 (1998)); CD70 (e.g., B-cell/T-cell) (Shaffer, et al., *Blood,* 117:4304-4314 (2011)); CD123 (e.g., Myeloid) (Tettamanti, et al., *Br J Haematol.,* 161:389-401 (2013)); Kappa (e.g., B-cell) (Vera, et al., *Blood,* 108:3890-3897 (2006)); Lewis Y (e.g., Myeloid) (Peinert, et al., *Gene Ther.,* 17:678-686 (2010), Ritchie, et al., *Mol Ther.* (2013)); NKG2D ligands (e.g., Myeloid) (Barber, et al., *Exp Hematol.,* 36:1318-1328 (2008), Lehner, et al., *PLoS One.,* 7:e31210 (2012), Song, et al., *Hum Gene Ther.,* 24:295-305 (2013), Spear, et al., *J Immunol.* 188:6389-6398 (2012)); ROR1 (e.g., B-cell) (Hudecek, et al., *Clin Cancer Res.* (2013)).

CAR targets for solid tumors include, but are not limited to, B7H3 (e.g., sarcoma, glioma) (Cheung, et al., *Hybrid Hybridomics,* 22:209-218 (2003)); CAIX (e.g., kidney) (Lamers, et al., *J Clin Oncol.,* 24:e20-e22. (2006)), Weijtens, et al., *Int J Cancer,* 77:181-187 (1998)); CD44 v6/v7 (e.g., cervical) (Hekele, et al., *Int J Cancer,* 68:232-238 (1996)), Dall, et al., *Cancer Immunol Immunother,* 54:51-60 (2005); CD171 (e.g., neuroblastoma) (Park, et al., *Mol Ther.,* 15:825-833 (2007)); CEA (e.g., colon) (Nolan, et al., *Clin Cancer Res.,* 5:3928-3941 (1999)); EGFRvIII (e.g., glioma) (Bullain, et al., *J Neurooncol.* (2009), Morgan, et al., *Hum Gene Ther.,* 23:1043-1053 (2012)); EGP2 (e.g., carcinomas) (Meier, et al., *Magn Reson Med.,* 65:756-763 (2011), Ren-Heidenreich, et al., *Cancer Immunol Immunother.,* 51:417-423 (2002)); EGP40 (e.g., colon) (Daly, et al., *Cancer Gene Ther.,* 7:284-291 (2000); EphA2 (e.g., glioma, lung) (Chow, et al., *Mol Ther.,* 21:629-637 (2013)); ErbB2(HER2) (e.g., breast, lung, prostate, glioma) (Zhao, et al., *J Immunol.,* 183:5563-5574 (2009), Morgan, et al., *Mol Ther.,* 18:843-851 (2010), Pinthus, et al., 114:1774-1781 (2004), Teng, et al., *Hum Gene Ther.,* 15:699-708 (2004), Stancovski, et al., *J Immunol.,* 151:6577-6582 (1993), Ahmed, et al., *Mol Ther.,* 17:1779-1787 (2009), Ahmed, et al., *Clin Cancer Res.,* 16:474-485 (2010), Moritz, et al., *Proc Natl Acad Sci U.S.A.,* 91:4318-4322 (1994)); ErbB receptor family (e.g., breast, lung, prostate, glioma) (Davies, et al., *Mol Med.,* 18:565-576 (2012)); ErbB3/4 (e.g., breast, ovarian) (Muniappan, et al., *Cancer Gene Ther.,* 7:128-134 (2000), Altenschmidt, et al., *Clin Cancer Res.,* 2:1001-1008 (1996)); HLA-A1/MAGE1 (e.g., melanoma) (Willemsen, et al., *Gene Ther.,* 8:1601-1608 (2001), Willemsen, et al., *J Immunol.,* 174:7853-7858 (2005)); HLA-A2/NY-ESO-1 (e.g., sarcoma, melanoma) (Schuberth, et al., *Gene Ther.,* 20:386-395 (2013)); FR-α (e.g., ovarian) (Hwu, et al., *J Exp Med.,* 178:361-366 (1993), Kershaw, et al., *Nat Biotechnol.,* 20:1221-1227 (2002), Kershaw, et al., *Clin Cancer Res.,* 12:6106-6115 (2006), Hwu, et al., *Cancer Res.,* 55:3369-3373 (1995)); FAP (e.g., cancer associated fibroblasts) (Kakarla, et al., *Mol Ther.* (2013)); FAR (e.g., rhabdomyosarcoma) (Gattenlohner, et al., *Cancer Res.,* 66:24-28 (2006)); GD2 (e.g., neuroblastoma, sarcoma, melanoma) (Pule, et al., *Nat Med.,* 14:1264-1270 (2008), Louis, et al., *Blood,* 118: 6050-6056 (2011), Rossig, et al., *Int J Cancer.,* 94:228-236 (2001)); GD3 (e.g., melanoma, lung cancer) (Yun, et al., *Neoplasia.,* 2:449-459 (2000)); HMW-MAA (e.g., melanoma) (Burns, et al., *Cancer Res.,* 70:3027-3033 (2010)); IL11Rα (e.g., osteosarcoma) (Huang, et al., *Cancer Res.,* 72:271-281 (2012)); IL13Rα2 (e.g., glioma) (Kahlon, et al., *Cancer Res.,* 64:9160-9166 (2004), Brown, et al., *Clin Cancer Res.* (2012), Kong, et al., *Clin Cancer Res.,* 18:5949-5960 (2012), Yaghoubi, et al., *Nat Clin Pract Oncol.,* 6:53-58 (2009)); Lewis Y (e.g., breast/ovarian/pancreatic) (Peinert, et al., *Gene Ther.,* 17:678-686 (2010), Westwood, et al., *Proc Natl Acad Sci U.S.A.,* 102:19051-19056 (2005), Mezzanzanica, et al., *Cancer Gene Ther.,* 5:401-407 (1998)); Mesothelin (e.g., mesothelioma, breast, pancreas) (Lanitis, et al., *Mol Ther.,* 20:633-643 (2012), Moon, et al., *Clin Cancer Res.,* 17:4719-4730 (2011)); Muel (e.g., ovarian, breast, prostate) (Wilkie, et al., *J Immunol.,* 180:4901-4909 (2008)); NCAM (e.g., neuroblastoma, colorectal) (Gilham, et al., *J Immunother.,* 25:139-151 (2002)); NKG2D ligands (e.g., ovarian, sacoma) (Barber, et al., *Exp Hematol.,* 36:1318-1328 (2008), Lehner, et al., *PLoS One,* 7:e31210 (2012), Song, et al., *Gene Ther.,* 24:295-305 (2013), Spear, et al., *J Immunol.,* 188:6389-6398 (2012)); PSCA (e.g., prostate, pancreatic) (Morgenroth, et al., *Prostate,* 67:1121-1131 (2007), Katari, et al., *HPB,* 13:643-650 (2011)); PSMA (e.g., prostate) (Maher, et al., *Nat Biotechnol.,* 20:70-75 (2002), Gong, et al., *Neoplasia.,* 1:123-127 (1999)); TAG72 (e.g., colon) (Hombach, et al., *Gastroenterology,* 113:1163-1170 (1997), McGuinness, et al., *Hum Gene Ther.,* 10:165-173 (1999)); VEGFR-2 (e.g., tumor vasculature) (*J Clin Invest.,* 120:3953-3968 (2010), Niederman, et al., *Proc Natl Acad Sci U.S.A.,* 99:7009-7014 (2002)).

b. Metabolic Stability

In some embodiments, cells' (e.g., CAR cells') metabolic stability is improved by equipping them with the capacity to make the very growth factors that are limiting in vivo. In some embodiments, nucleic acid cargo encoding an anti-apoptotic factor such as BCL-XL is transiently delivered to cells. B-cell lymphoma-extra large (Bcl-XL, or BCL2-like 1 isoform 1) is a transmembrane protein in the mitochondria. It is a member of the Bcl-2 family of proteins, and acts as a pro-survival protein in the intrinsic apoptotic pathway by preventing the release of mitochondrial contents such as cytochrome c, which would lead to caspase activation. Both amino acid and nucleic acid sequences encoding BCL-XL are known in the art and include, for example, UniProtKB—Q07817 (B2CL1_HUMAN), Isoform Bcl-X(L) (identifier: Q07817-1) (amino acid sequence); ENA|U72398|U72398.1 Human Bcl-x beta (bcl-x) gene, complete cds (genomic nucleic acid sequences); ENA|Z23115|Z23115.1 *H. sapiens* bcl-XL mRNA (mRNA/cDNA nucleic acid sequences).

In some embodiments, the nucleic cargo encodes a proliferation inducing factor such as IL-2. Both amino acid and nucleic acid sequences encoding IL-2 are known in the art and include, for example, UniProtKB—P60568 (IL2_HUMAN) (amino acid sequence); ENA|X00695|X00695.1 Human interleukin-2 (IL-2) gene and 5'-flanking region (genic nucleic acid sequence); and ENA|V00564|V00564.1 Human mRNA encoding interleukin-2 (IL-2) (mRNA/cDNA nucleic acid sequence).

However, the production of secreted IL-2 may have the unwanted side effect of also stimulating the proliferation of the lymphoma and Treg cells, and impairing the formation of memory T cells (Zhang, et al., *Nature Medicine*, 11:1238-1243 (2005)). In addition, the use of IL-2 in patients treated with Tumor Infiltrating Lymphocytes (TILs) led to increased toxicity (Heemskerk, et al., *Human Gene Therapy*, 19:496-510 (2008)). To avoid this potentiality, in addition or alternative to IL-2, the nucleic acid cargo can encode a chimeric γc cytokine receptor (CyCR) such as one composed of Interleukin-7 (IL-7) tethered to IL-7Rα/CD127 that confers exogenous cytokine independent, cell intrinsic, STAT5 cytokine signals (Hunter, et al., *Molecular Immunology*, 56:1-11 (2013)). The design is modular in that the IL-2Rβ/CD122 cytoplasmic chain can be exchanged for that of IL-7Rα/CD127, to enhance Shc activity. The constructs mimic wild type IL-2 signaling in human CD8+ T cells (Hunter, et al., *Molecular Immunology*, 56:1-11 (2013)) and should, therefore, work similarly to the IL-2 mRNA, without the unwanted to side effects.

Additionally and alternatively other antiapoptotic molecules and cytokines can be used to preserve cell viability in the native state.

Exemplary factors include, but are not limited to: Myeloid Cell Leukemia 1 (MCL-1) (e.g., UniProtKB—Q07820 (MCL1_HUMAN) (amino acid sequence); ENA|AF147742|AF147742.1 *Homo sapiens* myeloid cell differentiation protein (MCL1) gene, promoter and complete cds (genomic nucleic acid sequence); ENA|AF118124|AF118124.1 *Homo sapiens* myeloid cell leukemia sequence 1 (MCL1) mRNA, complete cds. (mRNA/cDNA nucleic acid sequence)) which is an antiapoptotic factor;

IL-7 (e.g., UniProtKB—P13232 (IL7_HUMAN) (amino acid sequence); ENA|EF064721|EF064721.1 *Homo sapiens* interleukin 7 (IL7) gene, complete cds. (genomic nucleic acid sequence); ENA|J04156|J04156.1 Human interleukin 7 (IL-7) mRNA, complete cds. (mRNA/cDNA nucleic acid sequence) which is important for T cell survival and development, and IL-15 (e.g., UniProtKB—P40933 (IL15_HUMAN) (amino acid sequence); ENA|X91233|X91233.1 *H. sapiens* IL15 gene (genomic nucleic acid sequence); ENA|U14407|U14407.1 Human interleukin 15 (IL15) mRNA, complete cds. (mRNA/cDNA nucleic acid sequence)) which promotes T and NK cell survival (Opferman, et al., *Nature*, 426: 671-676 (2003); Meazza, et al., *Journal of Biomedicine & Biotechnology*, 861920, doi: 10.1155/2011/861920 (2011); Michaud, et al., *Journal of Immunotherapy*, 33:382-390 (2010)). These cytokine mRNAs can be used either independently or in combination with BCL-XL, IL-2, and/or CyCR mRNA. Accordingly, in some embodiments, an mRNA encoding MCL-1, IL-7, IL-15, or a combination thereof is delivered to cells.

c. Inhibitory CAR (iCAR)

In some embodiments, T cell therapies are delivered to the CAR cells that have demonstrated long-term efficacy and curative potential for the treatment of some cancers, however, their use is limited by damage to non-cancerous tissues reminiscent of graft-versus-host disease after donor lymphocyte infusion. Any of the disclosed compositions and methods can be used in combination with a non-specific immunosuppression (e.g., high-dose corticosteroid therapy, which exert cytostatic or cytotoxic effects on T cells, to restrain immune responses), irreversible T cell elimination (e.g., so-called suicide gene engineering strategies), or a combination thereof. However, in some preferred embodiments, off-target effects are reduced by introducing into the CAR cell a construct encoding an inhibitory chimeric antigen receptor (iCAR). T cells with specificity for both tumor and off-target tissues can be restricted to tumor only by using an antigen-specific iCAR introduced into the T cells to protect the off-target tissue (Fedorov, et al., *Science Translational Medicine*, 5:215ra172 (2013)). The iCAR can include a surface antigen recognition domain combined with a powerful acute inhibitory signaling domain to limit T cell responsiveness despite concurrent engagement of an activating receptor (e.g., a CAR). In preferred embodiments, the iCAR includes a single-chain variable fragment (scFv) specific for an inhibitory antigen fused to the signaling domains of an immunoinhibitory receptor (e.g., CTLA-4, PD-1, LAG-3, 2B4 (CD244), BTLA (CD272), KIR, TIM-3, TGF beta receptor dominant negative analog etc.) via a transmembrane region that inhibits T cell function specifically upon antigen recognition. Once the CAR cell encounters a cell (e.g., a cancer cell) that does not express the inhibitory antigen, iCAR-transduced T cells can mount a CAR-induced response against the CAR's target antigen. A DNA iCAR using an scFv specific for PSMA with the inhibitory signaling domains of either CTLA-4 or PD-1 is discussed in (Fedorov, et al., *Science Translational Medicine*, 5:215ra172 (2013)).

Design considerations include that observation that PD-1 was a stronger inhibitor than CTLA-4, CTLA-4 exhibited cytoplasmic localization unless a Y165G mutant was used, and that the iCAR expression level is important.

iCAR can be designed against cell type specific surface molecules. In some embodiments the iCAR is designed to prevent T cells, NK cells, or other immune cell reactivity against certain tissues or cell types.

d. Reducing Endogenous Inhibitory Signaling

In some embodiments the cells are contacted with a nucleic acid cargo that reprograms the cells to prevent expression of one or more antigens. For example, in some embodiments the nucleic acid cargo is or encodes an interfering RNA that prevents expression of an mRNA encoding antigens such as CTLA-4 or PD-1. This method can be used to prepare universal donor cells. RNAs used to alter the expression of allogenic antigens may be used alone or in combination with RNAs that result in de-differentiation of the target cell.

Although the section above provides compositions and methods that utilized inhibitory signaling domains e.g., from CTLA-4 or PD-1 in an artificial iCAR to restrict on-target/off-tumor cytotoxicity, additionally or alternatively overall CAR cell on-tumor effector efficiency can be increased by reducing the expression of endogenous inhibitory signaling in the CAR cells so that the CAR cells become resistant to the inhibitory signals of the hostile tumor microenvironment.

CTLA-4 and PD-1 inhibit T cells at different stages in activation and function. CTLA-4 regulates T cell responses to self-antigens, as knockout mice spontaneously develop organ damage due to highly active, tissue-infiltrating T cells without specific antigen exposure (Tivol, et al., *Immunity*, 3:541-547 (1995); Waterhouse, et al., *Science*, 270:985-988 (1995)). Interestingly, conditional knockout of CTLA-4 in Treg cells recapitulates the global knockout indicating that it normally functions within Tregs (Wing, et al., *Science*, 322:271-275 (2008)). In contrast, PD-L1 knockout mice are autoimmune prone, but do not spontaneously develop massive inflammatory cell infiltration of normal organs, indicating that it's major physiological function is to mediate negative feedback control of ongoing tissue inflammation in an inducible manner (Dong, et al., *Immunity*, 20:327-336 (2004)). Indeed, according to the "adaptive resistance" hypothesis most tumors up-regulate PD-L1 in response to IFNγ; a key cytokine released by effector T cells including CART cells (Greenwald, et al., *Annu Rev Immunol*, 23:515-548 (2005); Carreno, et al., *Annu Rev Immunol*, 20:29-53 (2002); Chen, et al., *The Journal of Clinical Investigation*, 125:3384-3391 (2015); Keir, et al., *Annu Rev Immunol*, 26:677-704 (2008); Pentcheva-Hoang, et al., *Immunological Reviews*, 229:67-87 (2009)). PD-L1 then delivers an inhibitory signal to T cells decreasing their proliferation, and cytokine and perforin production (Butte, et al., *Immunity*, 27:111-122 (2007); Chen, et al., *Immunology*, 4:336-347 (2004); Park, et al., *Blood*, 116:1291-1298 (2010); Wherry, et al., *Nat Immunol*, 12:492-499 (2011); Zou, et al., *Immunology*, 8:467-477 (2008)). In addition, reverse signaling from the T cell through B7-H1 on cancer cells induces an anti-apoptotic effect that counteracts Fas-L signaling (Azuma, et al., *Blood*, 111:3635-3643 (2008)). Azuma, et al., *Blood*, 111:3635-3643 (2008)

In light of the up-regulation of B7-H1 by cancer cells and the association of its expression with cancer progression and poor clinical outcome (Flies, et al., *Journal of Immunotherapy*, 30:251-260 (2007); Nishimura, et al., *Immunity*, 11:141-151 (1999); Wang, et al., *Curr Top Microbiol Immunol*, 344:245-267 (2011)), antibodies antagonizing the PD-1 and CTLA-4 pathways have shown dramatic efficacy in solid tumors, particularly melanoma, with the combination of the two showing even more activity. The anti-CTLA-4 antibody, ipilimumab, improves overall survival in metastatic melanoma with increased T cell infiltration into tumors and increased intratumoral CD8+:Treg ratios, predominantly through inhibition of Treg cells (Hamid, et al., *J Transl Med*, 9:204 (2011); Ribas, et al., *Clinical Cancer Research: An Official Journal of the American Association for Cancer Research*, 15:6267-6276 (2009); Twyman-Saint, et al., *Nature*, 520:373-377 (2015)). The anti-PD-1 antibody, nivolumab, shows an overall response rate of 30-40% in metastatic melanoma (Robert, et al., *The New England Journal of Medicine*, 372:320-330 (2015); Topalian, et al., *J Clin Oncol*, 32:1020-1030 (2014)), with similar findings in early phase clinical trials for other solid tumors including metastatic renal cancer, non-small cell lung cancer and relapsed Hodgkin's Lymphoma (Ansell, et al., *The New England Journal of Medicine*, 372:311-319 (2015); Brahmer, et al., *J Clin Oncol*, 28:3167-3175 (2010); Topalian, et al., *The New England Journal of Medicine*, 366:2443-2454 (2012)). As resistance to anti-CTLA-4 antibodies in mouse melanoma models is due to up-regulation of PD-L181, the combination of both ipilimumab and nivolumab demonstrates further efficacy in both mouse models and human patients (Larkin, et al., *The New England Journal of Medicine*, 373:23-34 (2015); Spranger, et al., *J Immunother Cancer*, 2, 3, doi:10.1186/2051-1426-2-3 (2014); Yu, et al., *Clinical Cancer Research: An Official Journal of the American Association for Cancer Research*, 16:6019-6028 (2010)). Given the importance of the checkpoint inhibition pathway, it is believed that PD-1/CTLA-4 inhibition will release the brake, while the chimeric antigen receptor will push on the gas pedal. Importantly, transient delivery can be utilized to only transiently release the brake so that these cells will not lead to future autoimmune disease.

i. CRISPRi

To avoid permanent genome modification and inactivation of inhibitory signals such as PD-1 and CTLA-4, the dCAS9 CRISPRi system (Larson, et al., *Nat Protoc*, 8:2180-2196 (2013)) can be utilized. Nucleic acids encoding the enzymatically-inactive dCAS9-KRAB-repression domain, fusion protein, and sgRNAs to the inhibitory signaling protein (e.g. CTLA-4, PD-1, LAG-3, 2B4 (CD244), BTLA (CD272), KIR, TIM-3, TGF beta receptor dominant negative analog, etc.) can be co-delivered into the CAR cell. One or multiple sgRNA can be utilized. sgRNA can be designed to target the proximal promoter region and the coding region (nontemplate strand). An alternative approach utilizes the single-component Cpf1 CRISPR system, which is a smaller RNA to electroporate and express (Zetsche, et al., *Cell*, doi:10.1016/j.cell.2015.09.038 (2015)). Any of the foregoing RNA components can also be encoded by DNA expression construct such as a vector, for example a plasmid. Thus, either RNA, DNA, or a combination thereof can serve as the nucleic acid cargo.

Although broad inhibition of CTLA-4 with ipilimumab results in autoimmune sequelae, it is believed these side-effects will be decreased by restricting loss to CAR cells and transient nature of the mRNA delivery. Inhibitory function will be regained in time.

ii. Inhibitory RNAs

Nucleic acid cargo that can be delivered to cells can be or encode a functional nucleic acid or polypeptide designed to target and reduce or inhibit expression or translation of an inhibitory signaling molecule mRNA; or to reduce or inhibit expression, reduce activity, or increase degradation of inhibitory signaling molecule protein. Suitable technologies include, but are not limited to, antisense molecules, siRNA, miRNA, aptamers, ribozymes, triplex forming molecules, RNAi, etc. In some embodiments, the mRNA encode antagonist polypeptide that reduce inhibitory signaling.

In some embodiments, cargo that is or encodes functional RNAs suitable to reducing or silencing expression of CTLA-4, PD-1, LAG-3, 2B4 (CD244), BTLA (CD272), KIR, TIM-3, TGF beta receptor dominant negative analog, etc. alone or in combination can be delivered to cells.

In some embodiments, the cargo is an RNA or DNA that encodes a polypeptide that reduces bioavailability or serves as an antagonist or other negative regulator or inhibitor of CTLA-4, PD-1, LAG-3, 2B4 (CD244), BTLA (CD272), KIR, TIM-3, TGF beta receptor dominant negative analog, or another protein in an immune inhibitory pathway. The protein can be a paracrine, endocrine, or autocrine. It can regulate the cell intracellularly. It can be secreted and regulate the expressing cell and/or other (e.g., neighboring) cells. It can be a transmembrane protein that regulates the expressing cell and/or other cells. The protein can be fusion protein, for example an Ig fusion protein.

e. Pro-apoptotic Factors

Compositions and methods for activating and reactivating apoptotic pathways are also provided. In some embodiments, the nucleic acid is or encodes a factor or agent that activates, reactivates, or otherwise enhances or increases the intrinsic apoptosis pathway. Preferably the factor activates, reactivates, or otherwise enhances the intrinsic apoptosis pathway in cancer (e.g., tumor) cells, and is more preferably specific or targeted to the cancer cells.

In some embodiments, cells, following delivery of an anti-apoptotic factor or pro-proliferation factor, such as those discussed above or otherwise known in the art, are more resistant or less sensitive to induced apoptosis than untreated cells. A pro-apoptotic factor can induce or increase apoptosis in, for example, untreated cells relative to the treated T cells, and is preferably selective for cancer cells. The regimen results in a two-pronged attack, one cellular and one molecular, against the cancer cells.

The intrinsic apoptosis pathway can be activated, reactivated, or otherwise enhanced by targeting BCL-2 family members. BCL-2 family members are classified into three subgroups based on function and Bcl-2 Homology (BH) domains: multi-domain anti-apoptotic (e.g. BCL-2 or BCL-XL), multi-domain pro-apoptotic (e.g. BAX and BAK), and BH3-only pro-apoptotic (e.g. BIM) proteins. Members of the BH3-only subgroup, such as BIM, function as death sentinels that are situated throughout the cell, poised to transmit a variety of physiological and pathologic signals of cellular injury to the core apoptotic machinery located at the mitochondrion (Danial, et al., *Cell,* 116:205-219 (2004)).

In some embodiments, the pro-apoptotic factor is a pro-apoptotic BH3-mimetic. Various pro-apoptotic BH3-mimetics can simulate the native pro-apoptotic activities of BIM and afford the ability to manipulate multiple points of the apoptotic pathway. For example, BIM SAHB (Stabilized Alpha Helix of BCL-2 domains), ABT-737, and ABT-199 are pro-apoptotic BH3-mimetics designed by structural studies of the interaction between the pro-apoptotic BH3-only helical domain and the hydrophobic groove formed by the confluence of the BH1, BH2 and BH3 domains of anti-apoptotic proteins (Oltersdorf, et al., *Nature,* 435:677-681 (2005)).

D. Target Cells

In some embodiments, one or more particular cell types or tissue is the target of the disclosed complexes. The target cells can be in vitro, ex vivo or in a subject (i.e., in vivo). The application discussed herein can be carried out in vitro, ex vivo, or in vivo. For ex vivo application, the cells can be collected or isolated and treated in culture. Ex vivo treated cells can be administered to a subject in need thereof in therapeutically effective amount. For in vivo applications, cargo can be delivered to target cells passively, e.g., based on circulation of the composition, local delivery, etc., or can be actively targeted, e.g., with the additional a cell, tissue, organ specific targeting moiety. Thus, in some embodiments, cargo is delivered to the target cells to the exclusion of other cells. In some embodiments, cargo is delivered to target cells and non-target cells.

Target cells can be selected by the practitioner based on the desired treatment and therapy, and the intended effect of the nucleic acid cargo. For example, when the nucleic acid cargo is intended to induce cell death, the target cells may be cancer cells; when the nucleic acid cargo is intended to induce a genomic alteration, the target cells may be stem cells; when the nucleic acid cargo encodes a chimeric antigen receptor, the target cells may be immune cells.

3E10 scFv has previously been shown capable of penetrating into cell nuclei in an ENT2-dependent manner, with efficiency of nuclear uptake greatly impaired in ENT2-deficient cells (Hansen et al., *J Biol Chem* 282, 20790-20793 (2007)). ENT2 (SLC29A2) is a sodium-independent transporter that participates in the transport of purine and pyrimidine nucleosides and nucleobases, and is less sensitive to nitrobenzylmercaptopurine riboside (NBMPR) than ENT1.

In some embodiments, the target cells express ENT2 on their plasma member, their nuclear membrane, or both. Expression of ENT2 is relatively ubiquitous but varies in abundance among tissues and cell types. It has been confirmed in the brain, heart, placenta, thymus, pancreas, prostate and kidney (Griffiths, et al., *Biochem J,* 1997. 328 (Pt 3): p. 739-43, Crawford, et al., *J Biol Chem,* 1998. 273(9): p. 5288-93). Relative to other transporters, ENT2 has one of the highest mRNA expressions in skeletal muscle (Baldwin, et al., *Pflugers Arch,* 2004. 447(5): p. 735-43, Govindarajan, et al., *Am J Physiol Regul Integr Comp Physiol,* 2007. 293(5): p. R1809-22.). Thus, in some embodiments the target cells are brain, heart, placenta, thymus, pancreas, prostate, kidney, or skeletal muscle. Due to the high expression of ENT2 by skeletal muscle, the disclosed compositions and methods may be particularly effective for delivering nucleic acid cargo to these cells, and/or higher levels of cargo may be delivered to these cells compared to other cells expressing lower levels of ENT2.

Additional, non-limiting, exemplary target cells are discussed below.

1. Progenitor and Stem Cells

The cells can be hematopoietic progenitor or stem cells. In some embodiments, particularly those related to gene editing and gene therapy the target cells are CD34$^+$ hematopoietic stem cells. Hematopoietic stem cells (HSCs), such as CD34+ cells are multipotent stem cells that give rise to all the blood cell types including erythrocytes.

Stem cells can be isolated and enriched by one of skill in the art. Methods for such isolation and enrichment of CD34$^+$ and other cells are known in the art and disclosed for example in U.S. Pat. Nos. 4,965,204; 4,714,680; 5,061,620; 5,643,741; 5,677,136; 5,716,827; 5,750,397 and 5,759,793. As used herein in the context of compositions enriched in hematopoietic progenitor and stem cells, "enriched" indicates a proportion of a desirable element (e.g. hematopoietic progenitor and stem cells) which is higher than that found in the natural source of the cells. A composition of cells may be enriched over a natural source of the cells by at least one order of magnitude, preferably two or three orders, and more preferably 10, 100, 200 or 1000 orders of magnitude.

In humans, CD34$^+$ cells can be recovered from cord blood, bone marrow or from blood after cytokine mobilization effected by injecting the donor with hematopoietic growth factors such as granulocyte colony stimulating factor (G-CSF), granulocyte-monocyte colony stimulating factor (GM-CSF), stem cell factor (SCF) subcutaneously or intravenously in amounts sufficient to cause movement of hematopoietic stem cells from the bone marrow space into the peripheral circulation. Initially, bone marrow cells may be obtained from any suitable source of bone marrow, e.g. tibiae, femora, spine, and other bone cavities. For isolation of bone marrow, an appropriate solution may be used to flush the bone, which solution will be a balanced salt solution, conveniently supplemented with fetal calf serum or other naturally occurring factors, in conjunction with an acceptable buffer at low concentration, generally from about 5 to 25 mM. Convenient buffers include Hepes, phosphate buffers, lactate buffers, etc.

Cells can be selected by positive and negative selection techniques. Cells can be selected using commercially available antibodies which bind to hematopoietic progenitor or stem cell surface antigens, e.g. CD34, using methods known to those of skill in the art. For example, the antibodies may be conjugated to magnetic beads and immunogenic procedures utilized to recover the desired cell type. Other techniques involve the use of fluorescence activated cell sorting (FACS). The CD34 antigen, which is found on progenitor cells within the hematopoietic system of non-leukemic individuals, is expressed on a population of cells recognized by the monoclonal antibody My-10 (i.e., express the CD34 antigen) and can be used to isolate stem cell for bone marrow transplantation. My-10 deposited with the American Type Culture Collection (Rockville, Md.) as HB-8483 is commercially available as anti-HPCA 1. Additionally, negative selection of differentiated and "dedicated" cells from human bone marrow can be utilized, to select against substantially any desired cell marker. For example, progenitor or stem cells, most preferably CD34$^+$ cells, can be characterized as being any of CD3$^-$, CD7$^-$, CD8$^-$, CD10$^-$, CD14$^-$, CD15$^-$, CD19$^-$, CD20$^-$, CD33$^-$, Class II HLA$^+$ and Thy-1$^+$.

Once progenitor or stem cells have been isolated, they may be propagated by growing in any suitable medium. For example, progenitor or stem cells can be grown in conditioned medium from stromal cells, such as those that can be obtained from bone marrow or liver associated with the secretion of factors, or in medium including cell surface factors supporting the proliferation of stem cells. Stromal cells may be freed of hematopoietic cells employing appropriate monoclonal antibodies for removal of the undesired cells.

The isolated cells are contacted ex vivo with antibody and nucleic acid cargo complexes. Cells to which cargo has been delivered can be referred to as modified cells. A solution of the complexes may simply be added to the cells in culture. It may be desirable to synchronize the cells in S-phase. Methods for synchronizing cultured cells, for example, by double thymidine block, are known in the art (Zielke, et al., *Methods Cell Biol.,* 8:107-121 (1974)).

The modified cells can be maintained or expanded in culture prior to administration to a subject. Culture conditions are generally known in the art depending on the cell type. Conditions for the maintenance of CD34$^+$ in particular have been well studied, and several suitable methods are available. A common approach to ex vivo multi-potential hematopoietic cell expansion is to culture purified progenitor or stem cells in the presence of early-acting cytokines such as interleukin-3. It has also been shown that inclusion, in a nutritive medium for maintaining hematopoietic progenitor cells ex vivo, of a combination of thrombopoietin (TPO), stem cell factor (SCF), and flt3 ligand (Flt-3L; i.e., the ligand of the flt3 gene product) was useful for expanding primitive (i.e., relatively non-differentiated) human hematopoietic progenitor cells in vitro, and that those cells were capable of engraftment in SCID-hu mice (Luens et al., 1998, *Blood* 91:1206-1215). In other known methods, cells can be maintained ex vivo in a nutritive medium (e.g., for minutes, hours, or 3, 6, 9, 13, or more days) including murine prolactin-like protein E (mPLP-E) or murine prolactin-like protein F (mPIP-F; collectively mPLP-E/IF) (U.S. Pat. No. 6,261,841). It will be appreciated that other suitable cell culture and expansion methods can be used as well. Cells can also be grown in serum-free medium, as described in U.S. Pat. No. 5,945,337.

In another embodiment, the modified hematopoietic stem cells are differentiated ex vivo into CD4$^+$ cells culture using specific combinations of interleukins and growth factors prior to administration to a subject using methods well known in the art. The cells may be expanded ex vivo in large numbers, preferably at least a 5-fold, more preferably at least a 10-fold and even more preferably at least a 20-fold expansion of cells compared to the original population of isolated hematopoietic stem cells.

In another embodiment cells, can be dedifferentiated somatic cells. Somatic cells can be reprogrammed to become pluripotent stem-like cells that can be induced to become hematopoietic progenitor cells. The hematopoietic progenitor cells can then be treated with the compositions as described above with respect to CD34$^+$ cells. Representative somatic cells that can be reprogrammed include, but are not limited to fibroblasts, adipocytes, and muscles cells. Hematopoietic progenitor cells from induced stem-like cells have been successfully developed in the mouse (Hanna, J. et al. *Science,* 318:1920-1923 (2007)).

To produce hematopoietic progenitor cells from induced stem-like cells, somatic cells are harvested from a host. In a preferred embodiment, the somatic cells are autologous fibroblasts. The cells are cultured and transduced with vectors encoding Oct4, Sox2, Klf4, and c-Myc transcription factors. The transduced cells are cultured and screened for embryonic stem cell (ES) morphology and ES cell markers including, but not limited to AP, SSEA1, and Nanog. The transduced ES cells are cultured and induced to produce induced stem-like cells. Cells are then screened for CD41 and c-kit markers (early hematopoietic progenitor markers) as well as markers for myeloid and erythroid differentiation.

The modified hematopoietic stem cells or modified cells including, e.g., induced hematopoietic progenitor cells, are then introduced into a subject. Delivery of the cells may be affected using various methods and includes most preferably intravenous administration by infusion as well as direct depot injection into periosteal, bone marrow and/or subcutaneous sites.

The subject receiving the modified cells may be treated for bone marrow conditioning to enhance engraftment of the cells. The recipient may be treated to enhance engraftment, using a radiation or chemotherapeutic treatment prior to the administration of the cells. Upon administration, the cells will generally require a period of time to engraft. Achieving significant engraftment of hematopoietic stem or progenitor cells typically takes weeks to months.

A high percentage of engraftment of modified hematopoietic stem cells may not be necessary to achieve significant prophylactic or therapeutic effect. It is believed that the engrafted cells will expand over time following engraftment to increase the percentage of modified cells. It is believed that in some cases, engraftment of only a small number or small percentage of modified hematopoietic stem cells will be required to provide a prophylactic or therapeutic effect.

In preferred embodiments, the cells to be administered to a subject will be autologous, e.g. derived from the subject, or syngenic.

2. Embryos

In some embodiments, the compositions and methods can be used to deliver cargo to embryonic cells in vitro. The methods typically include contacting an embryo in vitro with an effective amount of antibody-cargo DNA to improve cargo transduction into the embryo. The embryo can be a single cell zygote, however, treatment of male and female gametes prior to and during fertilization, and embryos having 2, 4, 8, or 16 cells and including not only zygotes, but also morulas and blastocytes, are also provided. In some embodiments, the embryo is contacted with the compositions on culture days 0-6 during or following in vitro fertilization.

The contacting can be adding the compositions to liquid media bathing the embryo. For example, the compositions can be pipetted directly into the embryo culture media, whereupon they are taken up by the embryo.

3. Immune Cells

In some embodiments, the target cells are one or more types of immune cells. For example, different type of cells can be utilized or otherwise targeted for immunodulation and CAR-based therapies. The preferred targeted/engineered T cells may vary depending on the tumor and goals of the adoptive therapy. Effector T cells are typically preferred because they secreted high levels of effector cytokines and were proficient killers of tumor targets in vitro (Barrett, et al., *Annu Rev Med.,* 65: 333-347 (2014). Two complimentary lymphocyte populations with robust CAR mediated cytotoxicity are CD3-CD56+ NK cells and CD3+CD8+ T cells. Use of CD8+ T cells with CD4+ helper T cells leads to the increased presence of suppressive T-reg cells and dampened CD8+ T cell cytotoxicity. Since reprogrammed CD8+ T cells are pre-activated so that they act directly on tumor cells without the need for activation in the lymph node, CD4+ T cell support is not essential.

Additionally, there is evidence that infusion of naive T cells (Rosenberg, et al. *Adv. Cancer Res.,* 25:323-388 (1977)), central memory T cells (TCM cells) (Berger, et al. *J. Clin. Invest.,* 118:294-305 (2008)), Th17 cells (Paulos, et al., *Sci. Transl. Med.,* 2:55-78 (2010)), and T stem memory cells (Gattinoni, et al., *Nat. Med.,* 17:1290-1297 (2012)) may all have certain advantages in certain applications due, for example, to their high replicative capacity. Tumor Infiltrating Lymphocytes (TILs) also have certain advantages due to their antigen specificity and may be used in the delivery strategies disclosed herein.

Although sometime referred to as CAR cells, CAR immune cells, and CART cells (or CAR T cells), it will be appreciated that the CAR and other delivery strategies disclosed herein can also be carried out in other cell types, particularly different types of immune cells, including those discussed herein (e.g., lymphocytes, Natural Killer Cells, dendritic cells, B cells, antigen presenting cells, macrophage, etc.) and described elsewhere (see, e.g., Barrett, et al., *Annu Rev Med.,* 65: 333-347 (2014)).

4. Cancer Cells and Tumors

In some embodiments, the target cells are cancer cells. In such embodiments, methods of treatment are provided that may be useful in the context of cancer, including tumor therapy. The Examples below may indicate that DNA cargo may be delivered more generally to multiple tissues and not restricted to tumors, while RNA delivery may be more selective for tumor tissue. Thus, in some embodiments, when cancer cells are the target cells, the cargo may be composed of RNA (e.g., RNA alone).

Cargos that may be delivered to cancer cells include, but are not limited to, constructs for the expression of one or more pro-apoptotic factors, immunogenic factors, or tumor suppressors; gene editing compositions, inhibitory nucleic acids that target oncogenes; as well as other strategies discussed herein and elsewhere. In some embodiments, the cargo is mRNA that encodes a pro-apoptotic factor, or immunogenic factor that increases and immune response against the cells. In other embodiments, the cargo is siRNA the reduces expression of an oncogene or other cancer-causing transcript.

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The compositions and methods described herein may be useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. The disclosed compositions are particularly effective in treating carcinomas. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, cancers such as vascular cancer such as multiple myeloma, adenocarcinomas and sarcomas, of bone, bladder, brain, breast, cervical, colo-rectal, esophageal, kidney, liver, lung, nasopharangeal, pancreatic, prostate, skin, stomach, and uterine. In some embodiments, the disclosed compositions are used to treat multiple cancer types concurrently. The compositions can also be used to treat metastases or tumors at multiple locations.

The disclosed compositions and methods can be further understood through the following numbered paragraphs.

1. A composition comprising or consisting of
   (a) a 3E10 monoclonal antibody, cell-penetrating fragment thereof; a monovalent, divalent, or multivalent single chain variable fragment (scFv); or a diabody; or humanized form or variant thereof, and (b) a nucleic acid cargo comprising a nucleic acid encoding a polypeptide, a functional nucleic acid, a nucleic acid encoding a functional nucleic acid, or a combination thereof.

2. The composition of paragraph 1, wherein (a) comprises:
   (i) the CDRs of any one of SEQ ID NO:1-6, 12, 13, 46-48, or 50-52 in combination with the CDRs of any one of SEQ ID NO:7-11, 14, or 53-58;
   (ii) first, second, and third heavy chain CDRs selected from any of SEQ ID NOS:15-23, 42, or 43 in combination with first, second and third light chain CDRs selected from any of SEQ ID NOS:24-30, 44, or 45;
   (iii) a humanized form of (i) or (ii);
   (iv) a heavy chain comprising an amino acid sequence comprising at least 85% sequence identity to any one of SEQ ID NO:1 or 2 in combination with a light chain comprising an amino acid sequence comprising at least 85% sequence identity to SEQ ID NO:7 or 8;
   (v) a humanized form or (iv); or
   (vi) a heavy chain comprising an amino acid sequence comprising at least 85% sequence identity to any one of SEQ ID NO:3-6, 46-48, or 50-52 in combination with a light chain comprising an amino acid sequence comprising at least 85% sequence identity to SEQ ID NO:9-11 or 53-58.

3. The composition of paragraphs 1 or 2, wherein (a) comprises the same or different epitope specificity as monoclonal antibody 3E10, produced by ATCC Accession No. PTA 2439 hybridoma.

4. The composition of any one of paragraphs 1-3, wherein (a) is a recombinant antibody having the paratope of monoclonal antibody 3E10.

5. A composition comprising
   (a) a binding protein comprising
   (i) the CDRs of any one of SEQ ID NO:1-6, 12, 13, 46-48, or 50-52 in combination with the CDRs of any one of SEQ ID NO:7-11, 14, or 53-58;
   (ii) first, second, and third heavy chain CDRs selected from SEQ ID NOS:15-23, 42, or 43 in combination with first, second and third light chain CDRs selected from SEQ ID NOS:24-30, 44, or 45;
   (iii) a humanized form of (i) or (ii);
   (iv) a heavy chain comprising an amino acid sequence comprising at least 85% sequence identity to any one of SEQ ID NO:1 or 2 in combination with a light chain comprising an amino acid sequence comprising at least 85% sequence identity to SEQ ID NO:7 or 8;
   (v) a humanized form or (iv); or
   (vi) a heavy chain comprising an amino acid sequence comprising at least 85% sequence identity to any one of SEQ ID NO:3-6, 46-48, or 50-52 in combination with a light chain comprising an amino acid sequence comprising at least 85% sequence identity to SEQ ID NO:9-11 or 53-58, and
   (b) a nucleic acid cargo comprising a nucleic acid encoding a polypeptide, a functional nucleic acid, a nucleic acid encoding a functional nucleic acid, or a combination thereof.

6. The composition of any one of paragraphs 1-5, wherein (a) is bispecific.

7. The composition of paragraph 6, wherein (a) targets a cell type of interest.

8. The composition of any one of paragraphs 1-7, wherein (a) and (b) are non-covalently linked.

9. The composition of any one of paragraphs 1-8, wherein (a) and (b) are in a complex.

10. The composition of any one of paragraphs 1-9 wherein (b) comprises DNA, RNA, PNA or other modified nucleic acids, or nucleic acid analogs, or a combination thereof.

11. The composition of any one of paragraphs 1-10, wherein (b) comprises mRNA.

12. The composition of any one of paragraphs 1-11, wherein (b) comprises a vector.

13. The composition of paragraph 12, wherein the vector comprises a nucleic acid sequence encoding a polypeptide of interest operably linked to expression control sequence.

14. The composition of paragraph 13, wherein the vector is a plasmid.

15. The composition of any one of paragraphs 1-14, wherein (b) comprises a nucleic acid encoding a Cas endonuclease, a gRNA, or a combination thereof.

16. The composition of any one of paragraphs 1-15, wherein (b) comprises a nucleic acid encoding a chimeric antigen receptor polypeptide.

17. The composition of any one of paragraphs 1-16, wherein (b) comprises a functional nucleic acid.

18. The composition of any one of paragraphs 1-17, wherein (b) comprises a nucleic acid encoding a functional nucleic acid.

19. The composition of paragraphs 17 or 18, wherein the functional nucleic acid is antisense molecules, siRNA, miRNA, aptamers, ribozymes, RNAi, or external guide sequences.

20. The composition of any one of paragraphs 1-19, wherein (b) comprises a plurality of a single nucleic acid molecules.

21. The composition of any one of paragraphs 1-19, wherein (b) comprises a plurality of 2, 3, 4, 5, 6, 7, 8, 9, 10, or more different nucleic acid molecules.

22. The composition of any one of paragraphs 1-21, wherein (b) comprises or consists of nucleic acid molecules between about 1 and 25,000 nucleobases in length.

23. The composition of any one of paragraphs 1-22, wherein (b) comprises or consists of single stranded nucleic acids, double stranded nucleic acids, or a combination thereof.

24. The composition of any one of paragraphs 1-23, further comprising carrier DNA.

25. The composition of paragraph 24, wherein the carrier DNA is non-coding DNA.

26. The composition of paragraphs 24 or 25, wherein (b) is composed of RNA.

27. A pharmaceutical composition comprising the composition of any one of paragraphs 1-26 and a pharmaceutically acceptable excipient.

28. The composition of paragraph 27 further comprising polymeric nanoparticles encapsulating a complex of (a) and (b).

29. The composition of paragraph 28, wherein a targeting moiety, a cell penetrating peptide, or a combination thereof is associated with, linked, conjugated, or otherwise attached directly or indirectly to the nanoparticle.

30. A method of delivering a nucleic acid cargo to a cell comprising contacting the cell with an effective amount of the composition of any one of paragraphs 1-29.

31. The method of paragraph 30, wherein the contacting occurs ex vivo.

32. The method of paragraph 31, wherein the cells are hematopoietic stem cells, or T cells.

33. The method of any one of paragraphs 30-32, further comprising administering the cells to a subject in need thereof.

34. The method of paragraph 33, wherein the cells are administered to the subject in an effective amount to treat one or more symptoms of a disease or disorder.

35. The method of paragraph 30 wherein the contacting occurs in vivo following administration to a subject in need thereof.

36. The method of any one of paragraphs 33-35, wherein the subject has a disease or disorder.

37. The method of paragraph 36, wherein the disease or disorder is a genetic disorder, cancer, or an infection or infectious disease.

38. The method of paragraphs 36 or 37, wherein (b) is delivered into cells of the subject in an effective amount to reduce one or more symptoms of the disease or disorder in the subject.

39. A method of making the composition of any one of paragraphs 1-29 comprising incubating and/or mixing of (a) and (b) for an effective amount of time and at a suitable temperature to form complexes of (a) and (b), prior to contact with cells.

40. A method of making the composition of any one of paragraphs 1-29, comprising incubating and/or mixing of (a) and (b) for between about 1 min and about 30 min, about 10 min and about 20 min, or about 15 min, optionally at room temperature or 37 degrees Celsius.

41. A composition or method of any one of paragraphs 1-40 wherein 3E10 monoclonal antibody, cell-penetrating fragment thereof; a monovalent, divalent, or multivalent single chain variable fragment (scFv); or a diabody; or humanized form or variant thereof comprising the nucleic acid binding pocket of SEQ ID NOS:92 or 93, or a variant thereof with same or improved ability to bind to a nucleic acid.

42. A composition or method of any one of paragraphs 1-41 wherein the amino acid residue corresponding with D31 or N31 of a heavy chain amino acid sequence or a CDR thereof is substituted with R.

43. A composition or method of any one of paragraphs 1-42 wherein the amino acid residue corresponding with D31 or N31 of a heavy chain amino acid sequence or a CDR thereof is substituted with L.

44. A binding protein comprising
(i) a variant of CDRs of any one of SEQ ID NO:1-6, 12, 13, 46-48, or 50-52 in combination with the CDRs of any one of SEQ ID NO:7-11, 14, or 53-58;
(ii) a variant of the first heavy chain CDR, in combination with the second, and third heavy chain CDRs selected from SEQ ID NOS:15-23, 42, or 43 in combination with first, second and third light chain CDRs selected from SEQ ID NOS:24-30, 44, or 45;
(iii) a humanized form of (i) or (ii);
(iv) a heavy chain comprising an amino acid sequence comprising at least 85% sequence identity to any one of SEQ ID NO:1 or 2 in combination with a light chain comprising an amino acid sequence comprising at least 85% sequence identity to SEQ ID NO:7 or 8;
(v) a humanized form or (iv); or
(vi) a heavy chain comprising an amino acid sequence comprising at least 85% sequence identity to any one of SEQ ID NO:3-6, 46-48, or 50-52 in combination with a light chain comprising an amino acid sequence comprising at least 85% sequence identity to SEQ ID NO:9-11 or 53-58,
wherein the amino acid residue corresponding with D31 or N31 is substituted with R or L.

45. The binding protein of paragraph 44, comprising the nucleic acid binding pocket of SEQ ID NOS:92 or 93, or a variant thereof with same or improved ability to bind to a nucleic acid.

EXAMPLES

With respect to the experiments below, standard 3E10 sequence was used except wherein noted to be the D31N variant (e.g., Example 4). Both standard 3E10 and the D31N variant were used as full length antibodies.

Example 1: 3E10 Increases Cellular Uptake of PNA after 1 Hour

Materials and Methods

PNA alone (1 nmole) (MW=9984.39; 29 nucleotides in length), or PNA complexed with 3E10 (0.75 mg), was mixed at room temperature for 5 minutes. 200,000 K562 cells were then added to the suspension of 3E10, or PNA alone, in serum free media. Additional serum free media was added to a final volume of 500 ul. Following incubation with cells at 37° C. for 1 hr, the cells were centrifuged and washed three times with PBS prior to analysis by flow cytometry. The PNA was labeled by attachment to the fluorescent dye, tetramethylrhodamine (TAMRA).

Results

Figure 1B:
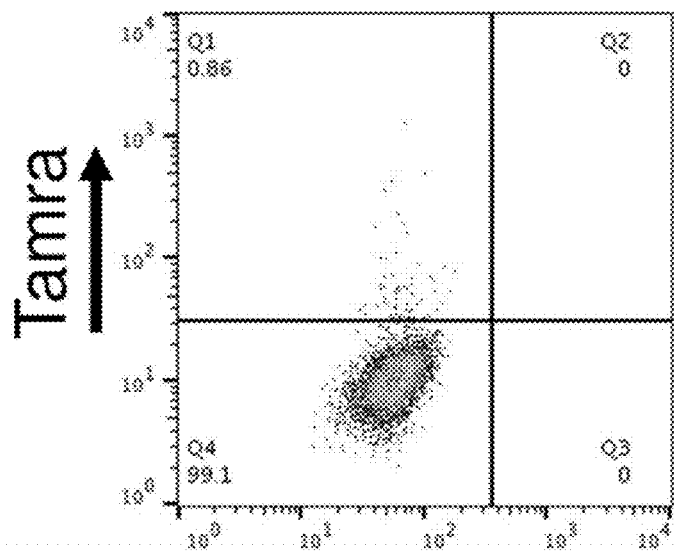
Figure 1C:
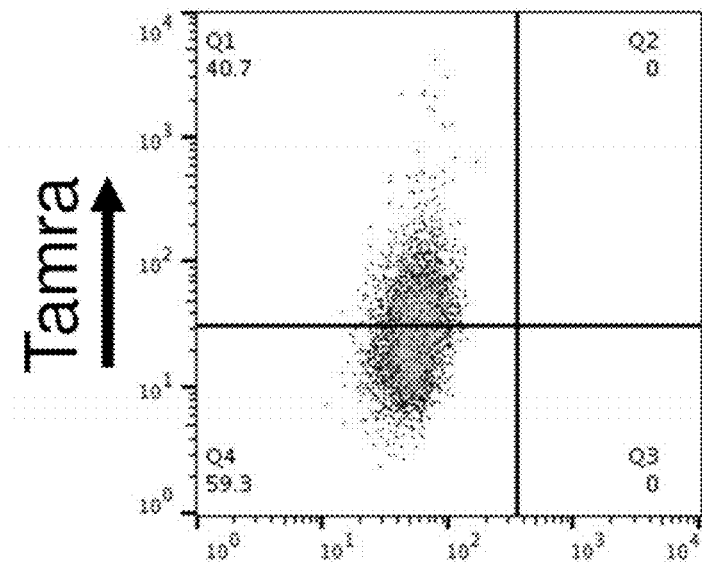
Figure 1D:
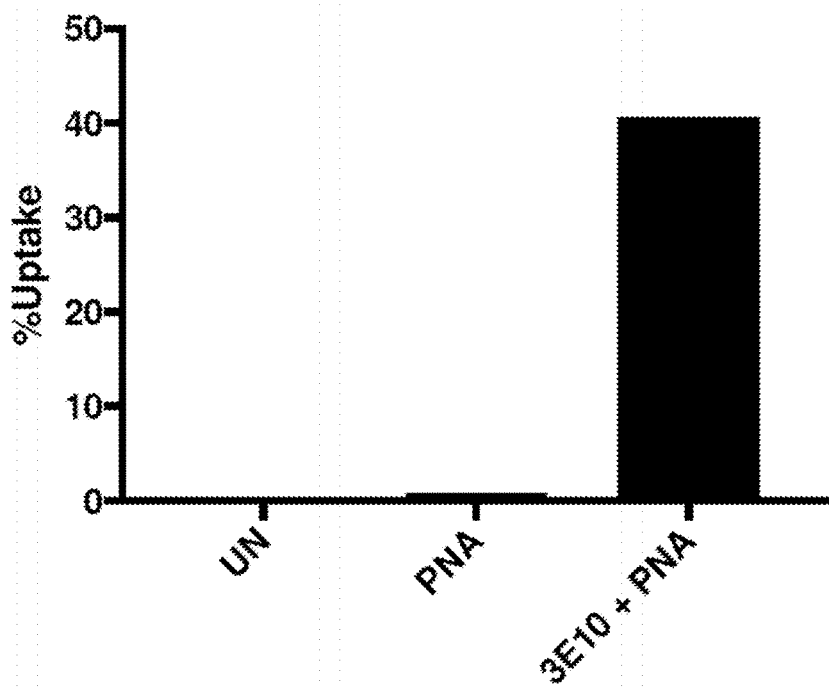
FIG. 1D is a bar graph quantifying the data in FIGS. 1A-1C.

The results are illustrated in flow cytometry dot plots (FIG. 1A-1C). % uptake was quantified (FIG. 1D).

The results show increased uptake of PNA when mixed with 3E10.

Example 2: 3E10 Increases Cellular Uptake of PNA after 24 Hours

Materials and Methods

PNA alone (1 nmole) (MW=9984.39; 29 nucleotides in length), or PNA complexed with 3E10 (0.75 mg), was mixed at room temperature for 5 minutes. 200,000 K562 cells were then added to the suspension of 3E10, or PNA alone, in serum free media. Additional serum free media was added to a final volume of 500 ul. Following incubation with cells at 37° C. for 24 hrs, the cells were centrifuged and washed three times with PBS prior to analysis by flow cytometry.

20,000 U2OS cells were seeded in 8-well chamber slides and allowed to adhere for 24 hours. Cells were subsequently treated with PNA alone (1 nmole), or PNA complexed with 3E10 (10 uM). Following incubation at 37° C. for 24 hrs, PNA or PNA mixed with 3E10 was washed with PBS prior to fixation and nuclear staining. PNA uptake was subsequently quantified by flow cytometry and imaged using fluorescent microscopy. The PNA was labeled by attachment to the fluorescent dye, tetramethylrhodamine (TAMRA).

Results

Figure 2A:
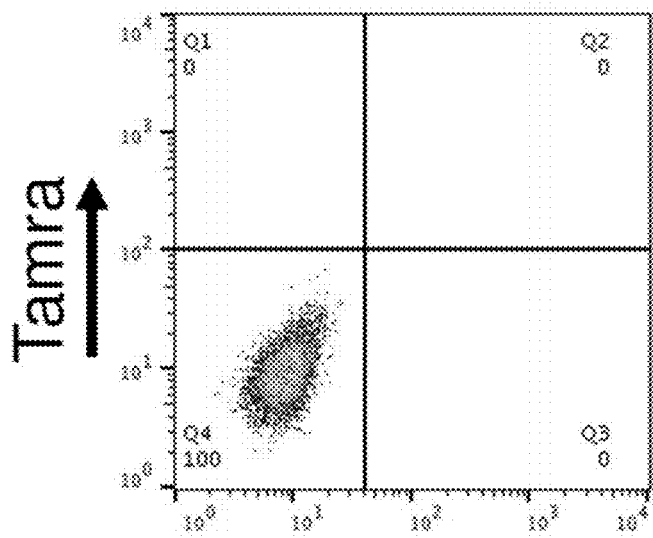
FIGS. 2A-2C are scatter plots showing control (2A), and uptake of PNA when alone (2B) and when mixed with 3E10 for 24 hour (2C).
Figure 2B:
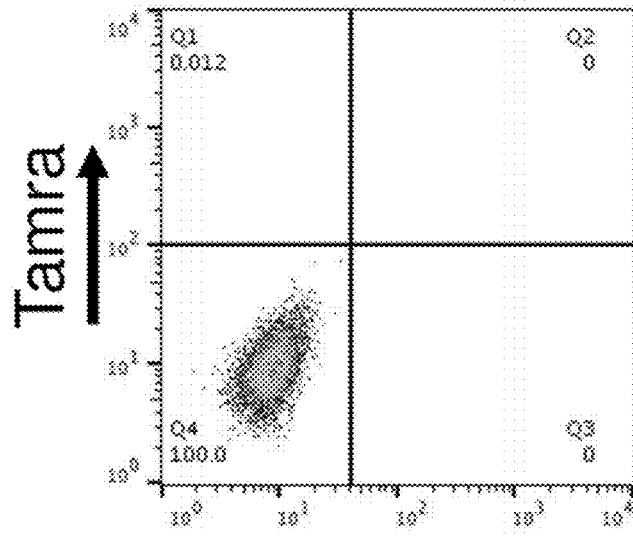
Figure 2C:
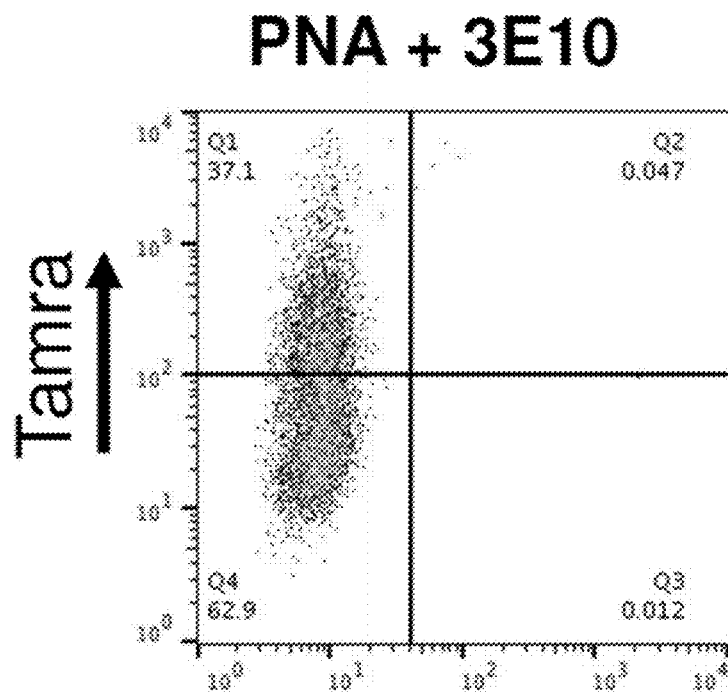
Figure 2D:
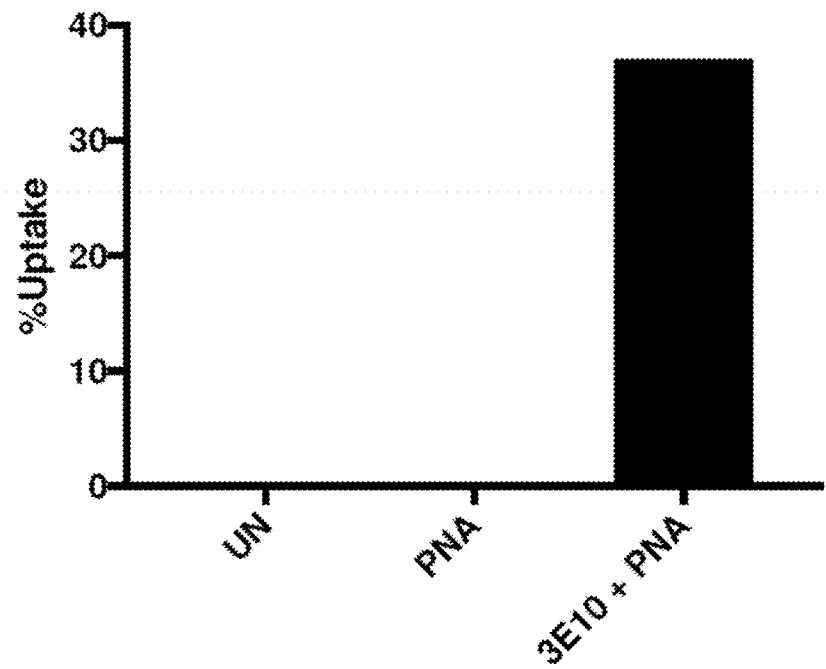
FIG. 2D is a bar graph quantifying the data in FIGS. 2A-2C.

The results are illustrated in flow cytometry dot plots (FIG. 2A-2C). % uptake was quantified (FIG. 2D).

The results show increased uptake of PNA when mixed with 3E10.

Fluorescent microscopy showed co-localization of nuclear DNA (DAPI in blue) and PNA (Tamra in red) evident by the production of a distinct pink hue.

Example 3: 3E10 Increases Cellular Uptake of siRNA after 24 Hours

Materials and Methods

Labeled siRNA (via attachment to fluorescein amidite, FAM) (1 nmole), or siRNA complexed with 3E10 (0.75 mg), was mixed at room temperature for 5 minutes. 200,000 K562 cells were then added to the suspension of 3E10, or siRNA alone, in serum free media. Additional serum free media was added to a final volume of 500 ul. Following incubation with cells at 37° C. for 24 hrs, the cells were centrifuged and washed three times with PBS prior to analysis by flow cytometry.

Results

Figure 3A:
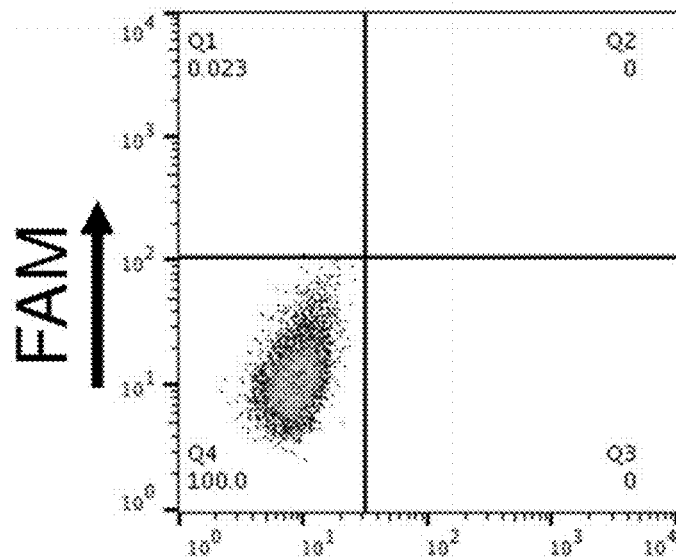
FIGS. 3A-3C are scatter plots showing control (3A), and uptake of siRNA when alone (3B) and when mixed with 3E10 for 24 hour (3C).
Figure 3B:
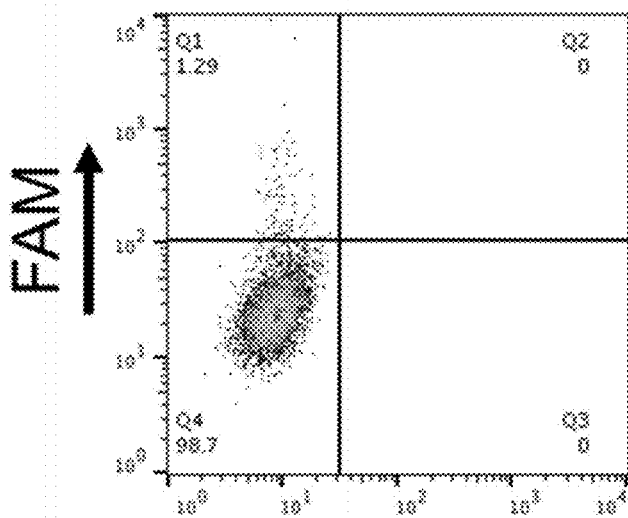
Figure 3C:
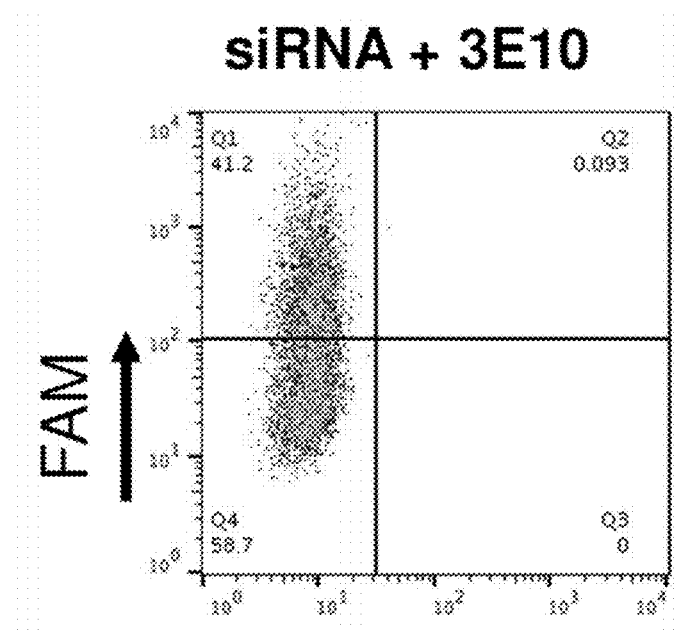
Figure 3D:
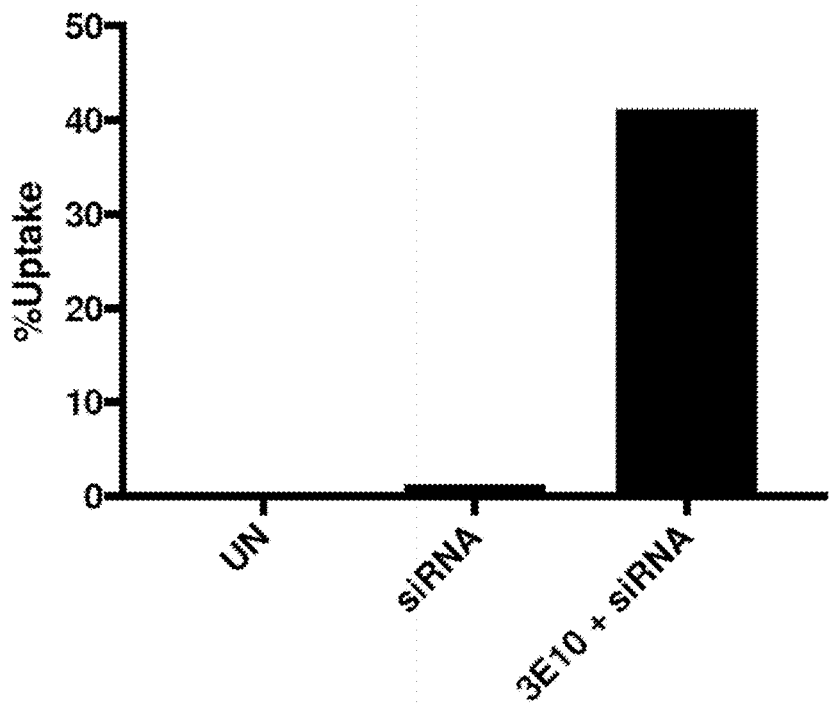
FIG. 3D is a bar graph quantifying the data in FIGS. 3A-3C.

The results are illustrated in flow cytometry dot plots (FIG. 3A-3C). % uptake was quantified (FIG. 3D).

The results show increased cell uptake of siRNA when mixed with 3E10.

Example 4: 3E10 Increases Cellular Uptake of mRNA after 24 Hours

Materials and Methods

Labeled mRNA (by attachment to cyanine 5, Cy5) (2 ug) alone or labeled mRNA complexed with 3E10 (2.5, 5, and 10 uM), were mixed at room temperature for 5 minutes. The suspensions of 3E10 plus mRNA, or mRNA alone, were added to 200,000 K562 cells in serum free media. Additional serum free media was added to a final volume of 500 ul. Following incubation with cells at 37° C. for 24 hrs, the cells were centrifuged and washed three times with PBS prior to analysis by flow cytometry.

Results

Figure 4A:
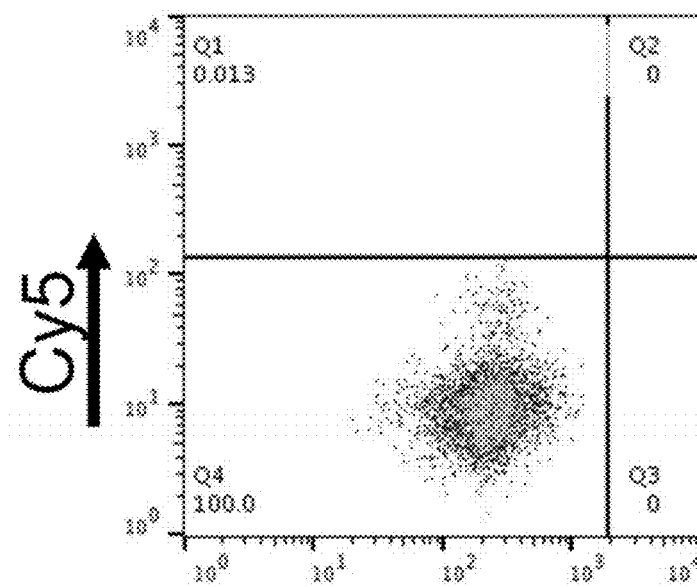
FIGS. 4A-4H are scatter plots showing control (4A), and uptake of mRNA when alone (4B) and when mixed at various concentrations with 3E10 for 24 hour (4C-4H).
Figure 4B:
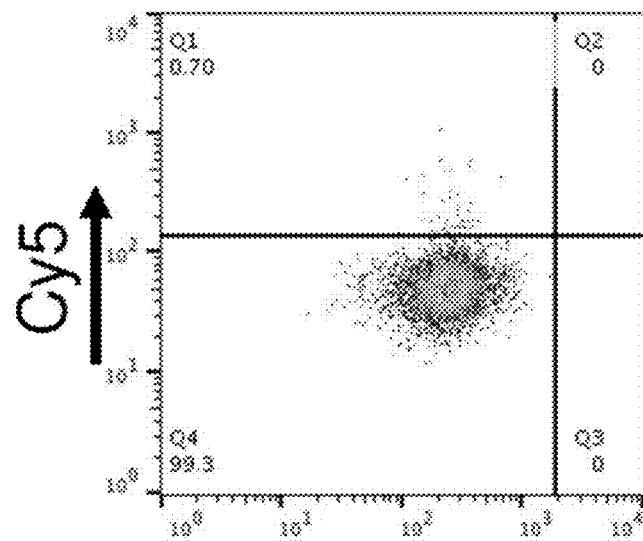
Figure 4C:
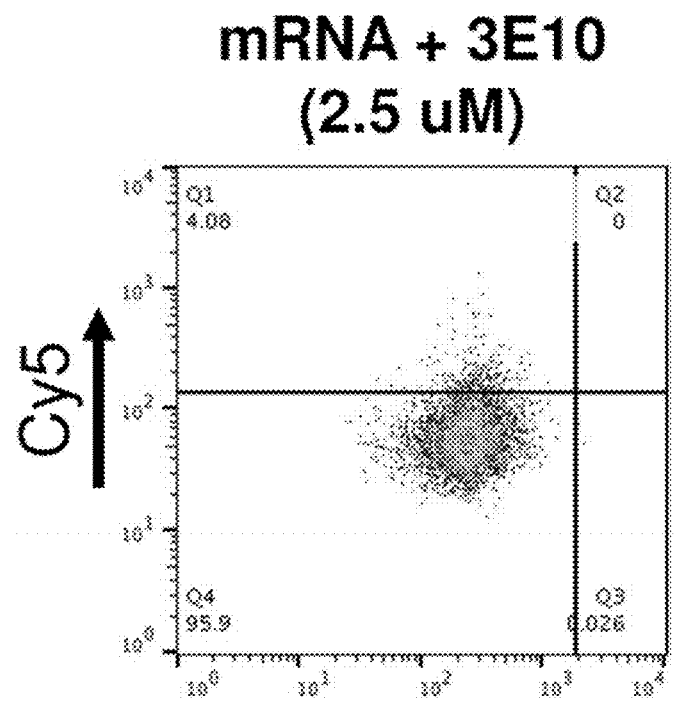
Figure 4D:
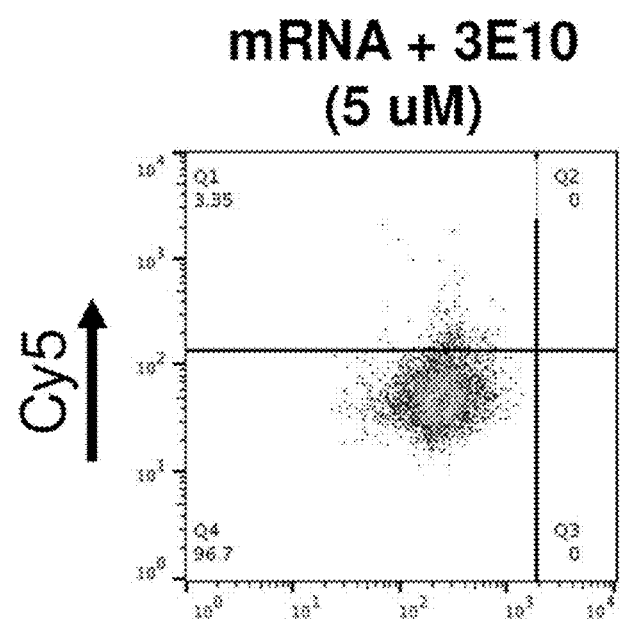
Figure 4E:
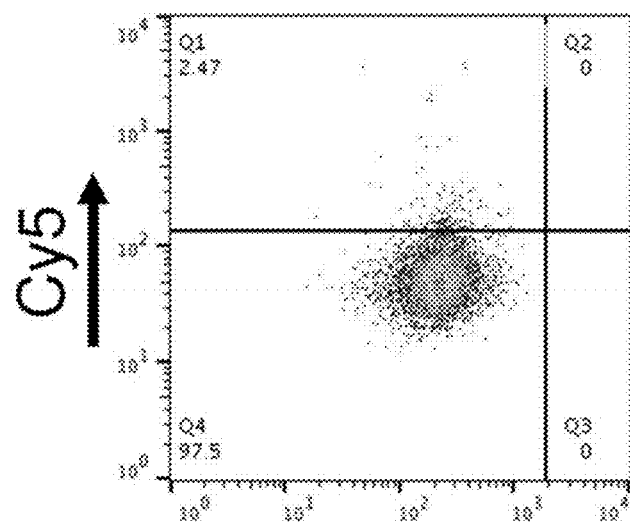
Figure 4F:
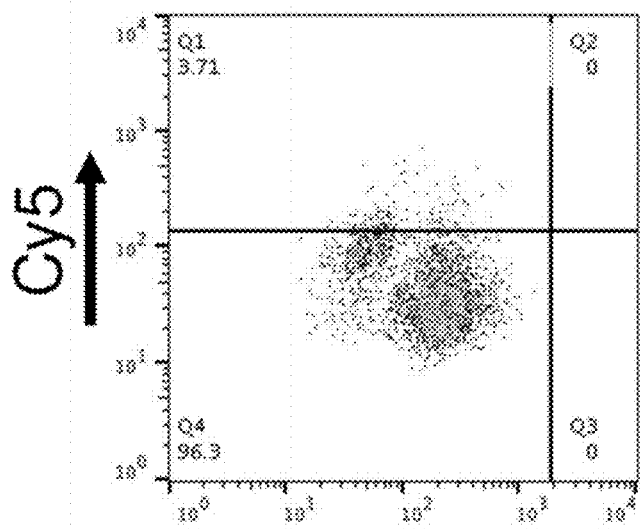
Figure 4G:
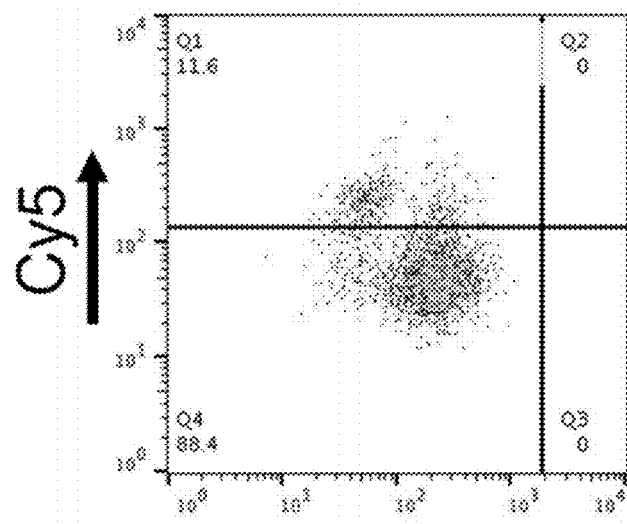
Figure 4H:
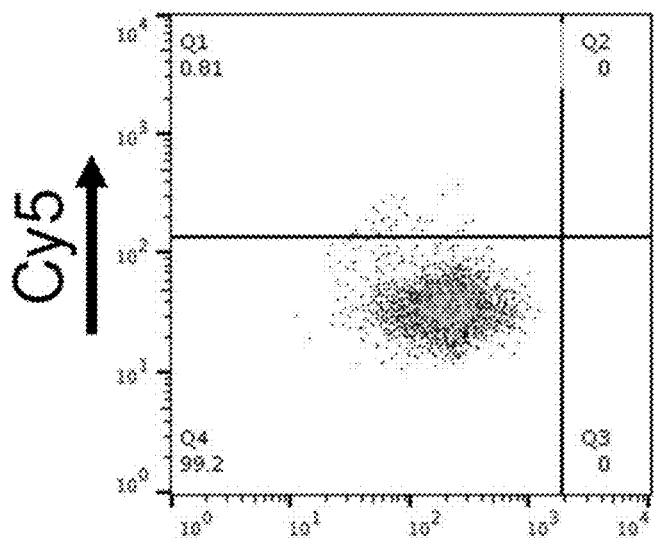
Figure 4I:
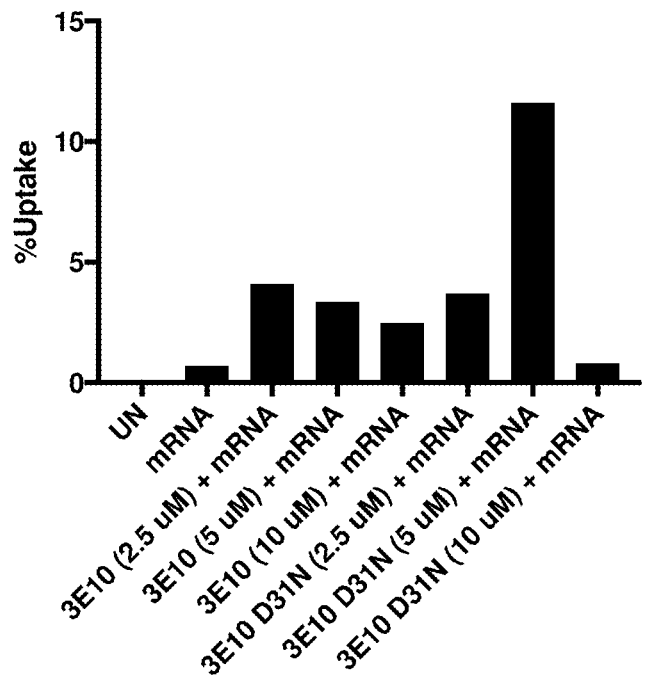
FIG. 4I is a bar graph quantifying the data in FIGS. 4A-4H.

The results are illustrated in flow cytometry dot plots (FIG. 4A-4H). % uptake was quantified (FIG. 4I).

The results show increased uptake of mRNA when mixed with 3E10. Note that delivery of mRNA by the D31N variant of 3E10 resulted in the highest levels of mRNA cell uptake.

Fluorescent microscopy showed functional GFP expression in U2OS cells after translation of the same Cy5 labeled mRNA, which encodes for a green fluorescent protein (GFP) reporter.

Example 5: 3E10 Increases Cellular Uptake of mRNA after 1 Hours

Materials and Methods

Labeled mRNA (Cy5) (2 ug) or labeled mRNA complexed with the D31N variant of 3E10 (0.1-10 uM) were mixed at room temperature for 5 minutes. The suspensions of 3E10 plus mRNA, or mRNA alone, were added to 200,000 K562 cells in serum free media. Additional serum free media was added to a final volume of 500 ul. Following incubation with cells at 37° C. for 1 hr, the cells were centrifuged and washed three times with PBS prior to analysis by flow cytometry.

Results

Figure 5A:
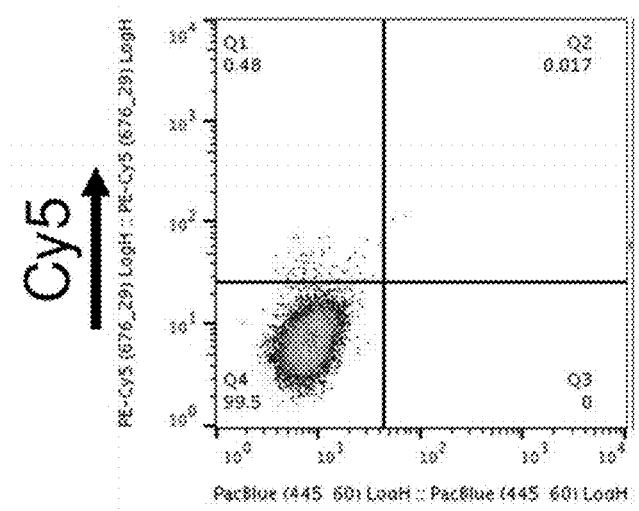
FIGS. 5A-5H are scatter plots showing control (5A), and uptake of mRNA when alone (5B) and when mixed at various concentrations with 3E10 for 1 hour (5C-5H).
Figure 5B:
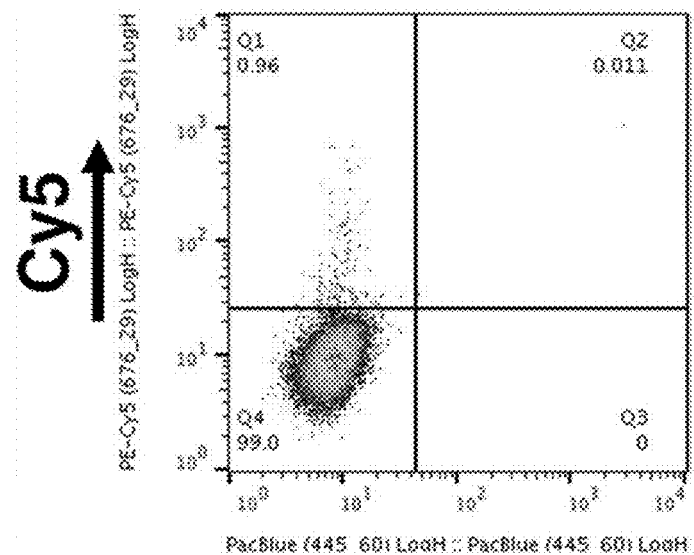
Figure 5C:
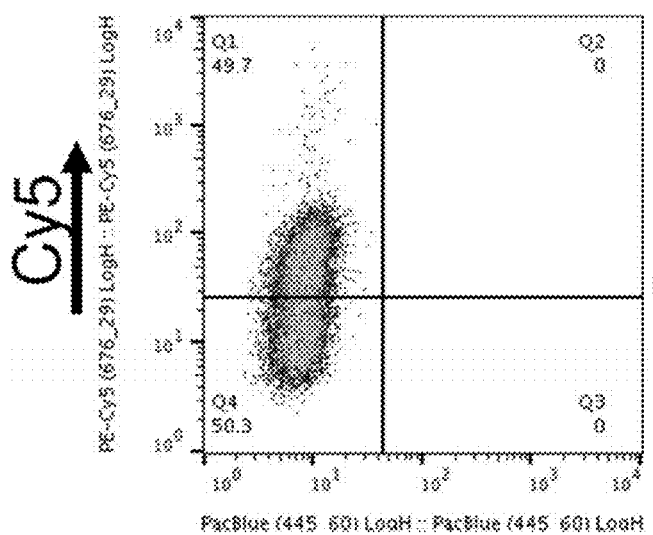
Figure 5D:
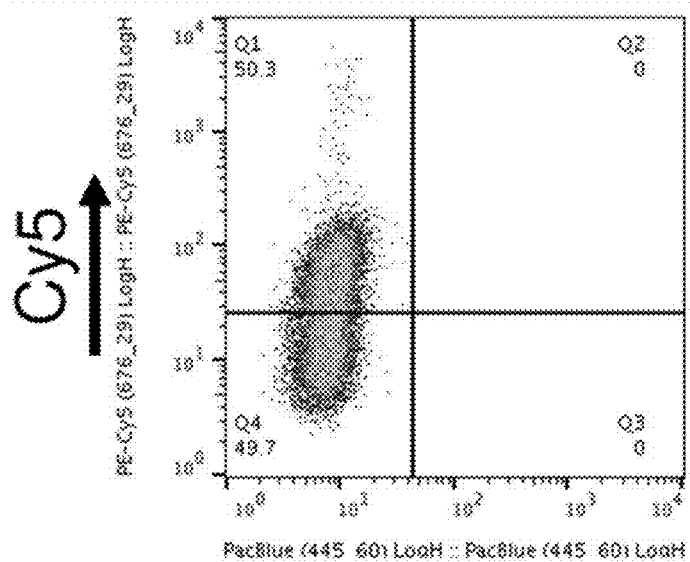
Figure 5E:
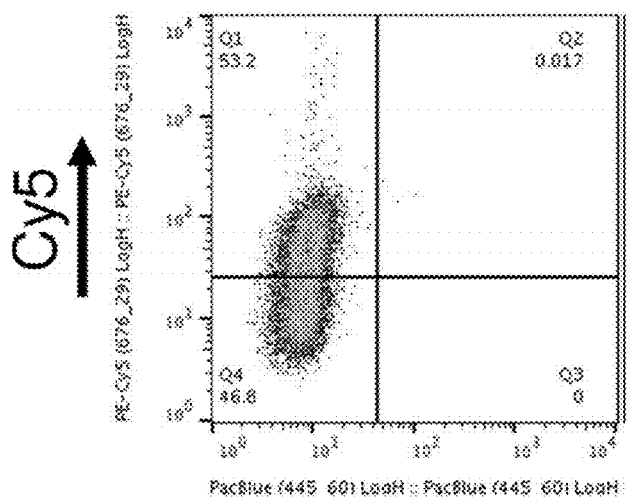
Figure 5F:
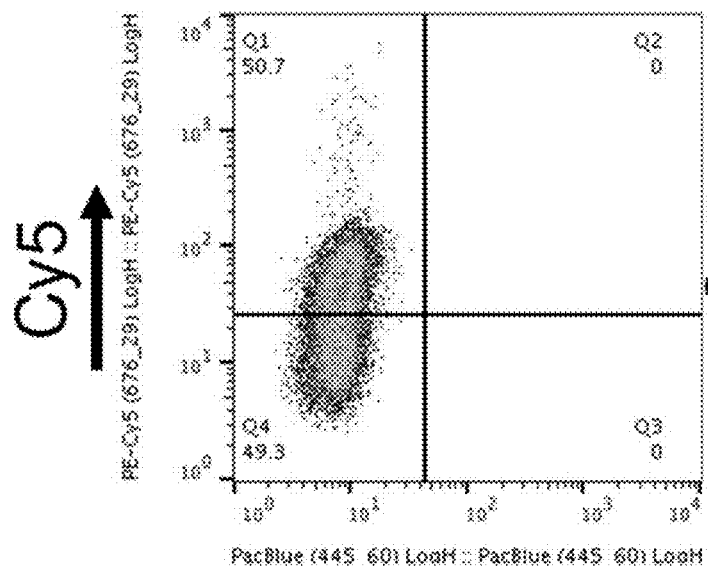
Figure 5G:
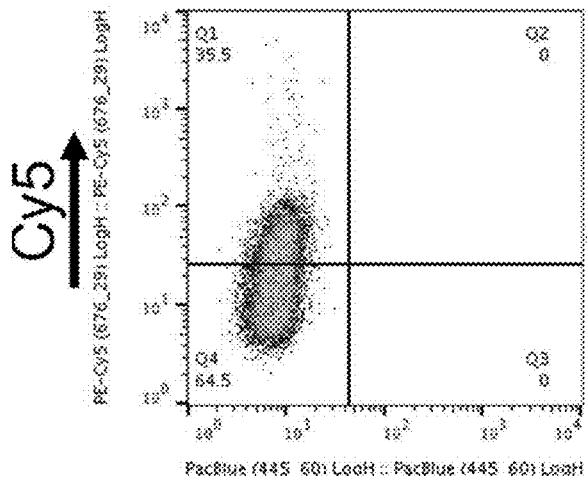
Figure 5H:
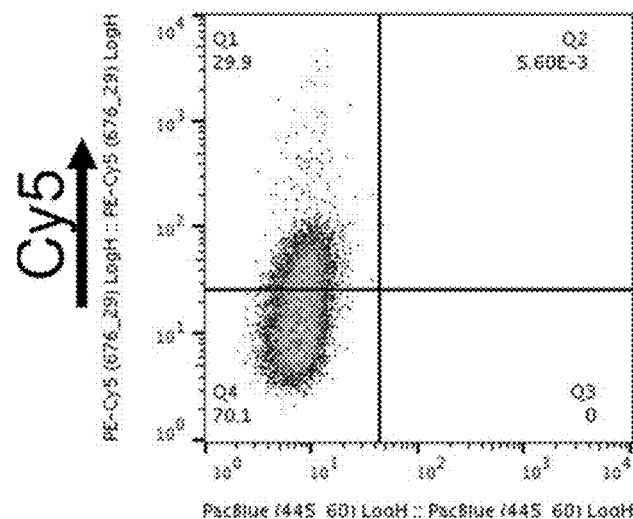
Figure 5I:
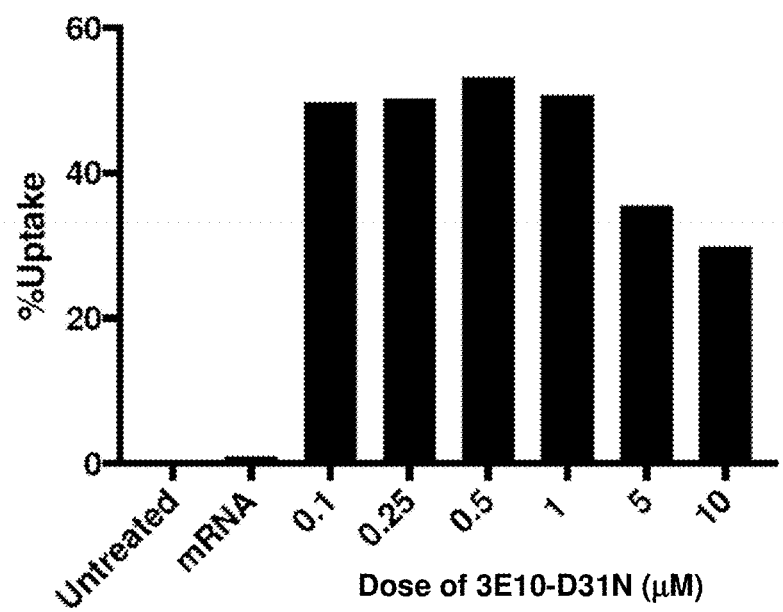
FIG. 5I is a bar graph quantifying the data in FIGS. 5A-5H.

The results are illustrated in flow cytometry dot plots (FIG. 5A-5H). % uptake was quantified (FIG. 5I).

Example 6: 3E10 Increases Cellular Uptake of Plasmid DNA

Materials and Methods

GFP reporter plasmid DNA (250 ug) was complexed with 3E10 (10 uM) at room temperature for 5 minutes. The suspension of 3E10 plus plasmid DNA, or plasmid DNA alone, were added to 200,000 K562 cells in serum free media. Additional serum free media was added to a final volume of 500 ul. Following incubation with cells at 37° C. for 24 hrs, the cells were centrifuged and washed three times with PBS. 72 hours after the initial treatment, cells were imaged and analyzed for GFP expression.

Results

Figure 6:
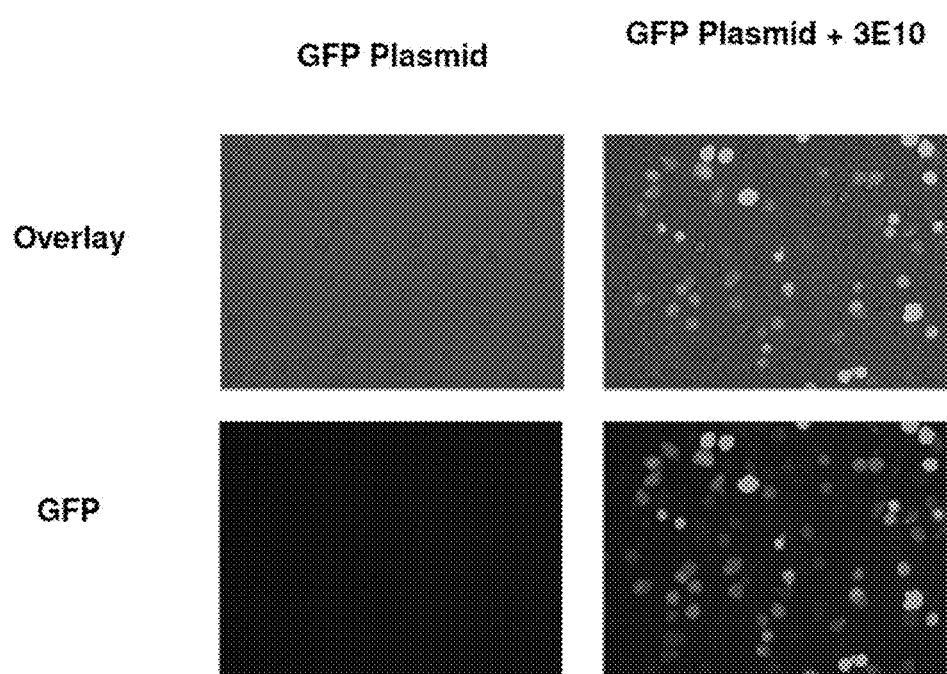
FIG. 6 is a series of images showing cellular expression of a GFP reporter plasmid DNA 72 hours after mixture with 3E10 and 24 hours of incubation with cells.

Results indicate that GFP plasmid was robustly taken up by cells when 3E10 was combined with the plasmid DNA, as measured by green fluorescence, indicating uptake and functional expression of the GFP construct. No uptake or green fluorescence was seen when plasmid DNA alone was used. (FIG. 6).

Example 7: 3E10 Mediates mRNA Delivery In Vivo

Materials and Methods 10 ug of mRNA encoding GFP was mixed with 0.1 mg of 3E10 for 15 minutes at room temperature. mRNA complexed to 3E10 was injected systemically to BALB/c mice bearing EMT6 flank tumors measuring 100 mm$^3$. 20 hours after treatment, tumors were harvested and analyzed for mRNA expression (GFP) using IVIS imaging.

Results

3E10-mediated delivery of mRNA resulted in significantly higher levels of GFP expression in the tumor compared to freely injected mRNA, which did not yield any GFP expression in the tumor. There was no detectable expression of GFP in any of the normal tissues examined with either treatment, including liver, spleen, heart, and kidney. The results indicate robust delivery of mRNA into tumors, with functional translation and expression.

Example 8: 3E10 Mediates siRNA Delivery In Vivo

Materials and Methods 40 ug of fluorescently labeled siRNA was mixed with increased doses of 3E10 (0.25, 0.5, and 1 mg) for 15 minutes at room temperature. siRNA complexed to 3E10 was injected systemically to BALB/c mice bearing EMT6 flank tumors measuring 100 mm$^3$. 20 hours after treatment, tumors were harvested and analyzed for siRNA delivery using IVIS imaging.

40 ug of fluorescently labeled siRNA was mixed with 1 mg 3E10 or 0.1 mg of the D31N variant of 3E10 for 15 minutes at room temperature. siRNA complexed to 3E10 was injected systemically to BALB/c mice bearing EMT6 flank tumors measuring 100 mm$^3$. 20 hours after treatment, tumors were harvested and analyzed for siRNA delivery using IVIS imaging.

Results

Figure 7A:
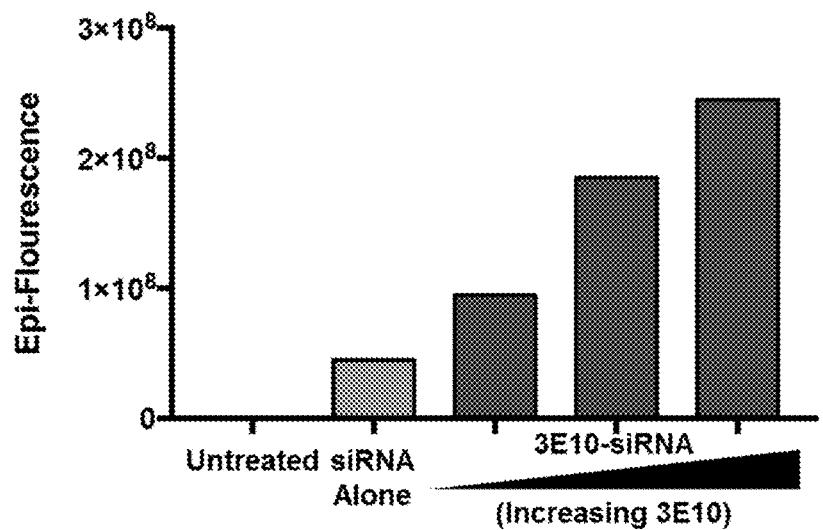
FIG. 7A is a bar graph showing accumulation in tumors of fluorescently labeled siRNA mixed with increasing doses of 3E10 (0.25, 0.5, and 1 mg) for 15 minutes at room temperature prior to systemic injection in mice.

As shown in FIG. 7A, increasing doses of 3E10 result in higher accumulation of siRNA in tumors.

Figure 7B:
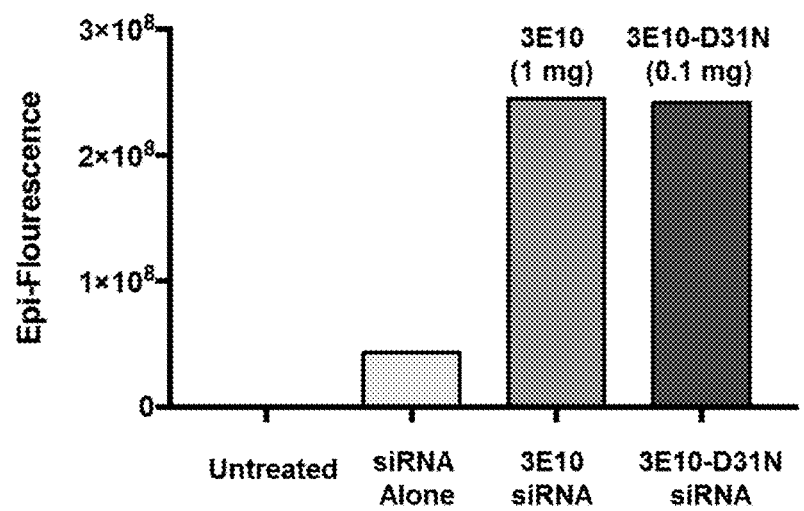
FIG. 7B is a bar graph showing accumulation in tumors of fluorescently labeled siRNA mixed with 1 mg 3E10 or 0.1 mg D31N variant 3E10 for 15 minutes at room temperature prior to systemic injection in mice. All tumors were analyzed 24 hours after injection.

As shown in FIG. 7B, a tenfold lower dose of D31N 3E10 resulted in similar levels of siRNA delivery as 3E10.

Unless defined otherwise, all technical and scientific terms used herein have the same meanings as commonly understood by one of skill in the art to which the disclosed invention belongs. Publications cited herein and the materials for which they are cited are specifically incorporated by reference.

Example 9: Carrier DNA Enhances mRNA to Non-Tumor Tissue

Materials and Methods 2 ug of fluorescently labeled mRNA was mixed with 20 ug of 3E10-D31N with or without carrier DNA (5 ug) for 15 minutes at room temperature. mRNA complexed to 3E10 was injected to fetuses at E15.5. 24-48 hours after treatment, fetuses were harvested and analyzed for mRNA delivery using IVIS imaging.

Results

Without carrier DNA, 3E10-D31N complexed to mRNA was rapidly cleared from fetuses at 24 hours. The addition of carrier DNA, however, resulted in detectable mRNA signal in multiple tissues of the fetus at 48 hours.

The Examples above may indicate that DNA cargo delivery may be more general to multiple tissues and not restricted to tumors, while RNA delivery may be more selective for tumor tissue.

Example 10: 3E10 (D31N) Complexed with mRNA and Carrier DNA Results in Sustained Levels Protein Expression Materials and Methods 10 ug of luciferase mRNA and 10 ug of single stranded carrier DNA (60 nts) was mixed with 100 ug of 3E10 (WT) or 3E10 (D31N) for 15 minutes at room temperature. mRNA complexed to 3E10 was injected intramuscularly (IM) in the right quadricep of each mouse. Luciferase expression was monitored over 6 days.

Results

Figure 8:
FIG. 8 is a line graph showing 3E10-mediated delivery of mRNA (bioluminescene (Photons/second)) to mouse muscles (IM) over time (days post-IM injection).

As seen in FIG. 8, administration of 3E10 (D31N) complexed with mRNA and carrier DNA resulted in sustained levels of luciferase expression, while 3E10 (WT) complexed to mRNA and carrier DNA failed to produce any appreciable signal above background.

Example 11: Distribution of IV Injected 3E10 In Vivo

Figures 9A, 9B:
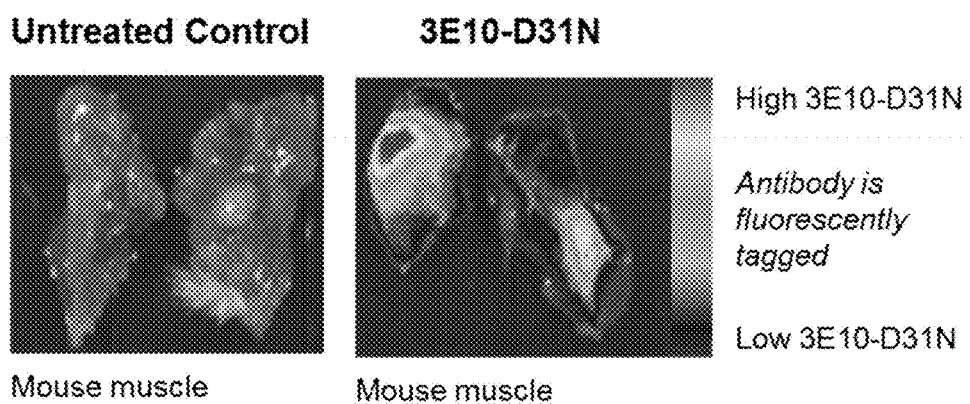
FIGS. 9A and 9B are images showing control (FIG. 9A) and distribution of IV Injected 3E10-D31N to muscle (FIG. 9B), imaged by IVIS (Perkin Elmer) 24 hours after injection.
Figure 9C:
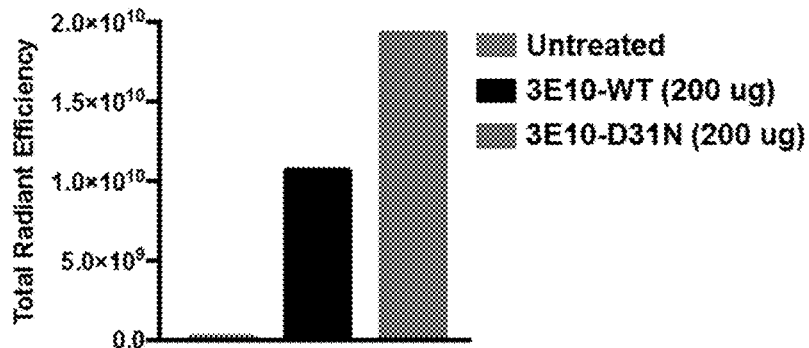
FIG. 9C is a bar graph quantifying the fluorescence in the IVIS images.

Distribution of IV injected 3E10 to muscle was investigated. Mice were injected intravenously with 200 μg of 3E10, WT or D31N, labeled with VivoTag680 (Perkin Elmer). Four hours after injection, muscle was harvested and imaged by IVIS (Perkin Elmer) (FIGS. 9A and 9B). Quantification of IVIS image demonstrates that 3E10-D31N achieves higher distribution to muscle when compared to 3E10-WT (FIG. 9C).

Figure 10:
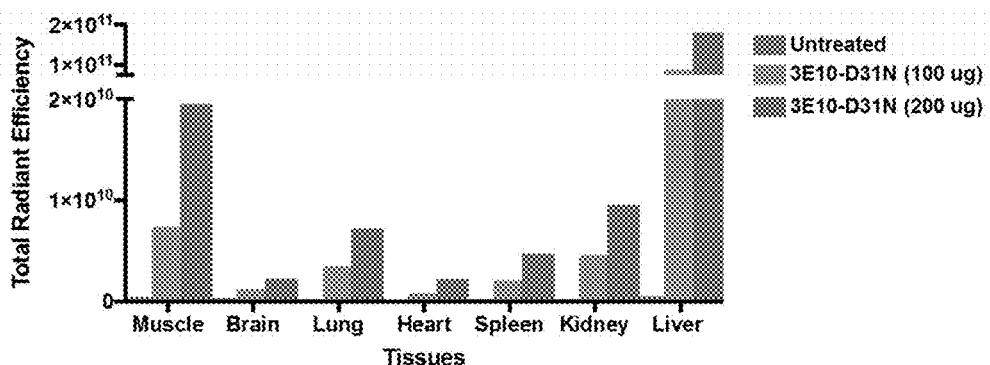
FIG. 10 is a bar graph quantifying the fluorescence in the IVIS images of dose-dependent biodistribution of 3E10-D31N to tissues 24 hours following 100 μg or 200 μg intravenous injection of 3E10-D31N labeled with VivoTag680 into mice (Perkin Elmer).

Dose-dependent biodistribution of 3E10-D31N to tissues was investigated. Mice were injected intravenously with 100 μg or 200 μg of 3E10-D31N labeled with VivoTag680 (Perkin Elmer). 24 hours after injection, tissues were harvested and imaged by IVIS (Perkin Elmer). Quantification of tissue distribution demonstrated a dose-dependent, two-fold increase in muscle accumulation without a commensurate increase in multiple tissues including liver (FIG. 10).

Figures 11A, 11B:
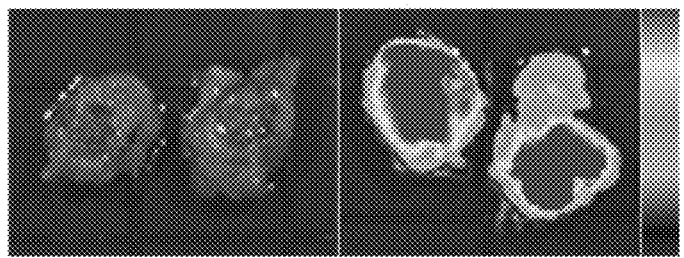
FIGS. 11A and 11B are images showing control (FIG. 11A) and distribution of IV Injected 3E10-D31N to syngeneic colon tumors (CT26) (FIG. 11B), imaged by IVIS (Perkin Elmer) 24 hours after injection.
Figure 11C:
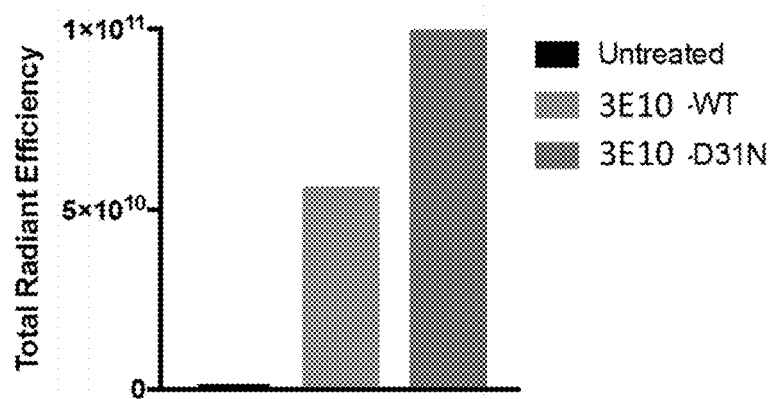
FIG. 11C is a bar graph quantifying the fluorescence in the IVIS images.

Distribution of 3E10 to tumors. Mice bearing flank syngeneic colon tumors (CT26) were injected intravenously with 200 μg of 3E10, WT or D31N, labeled with VivoTag680 (Perkin Elmer). 24 hours after injection, tumors were harvested and imaged by IVIS (Perkin Elmer) (FIG. 11A-11B). Quantification of tumor distribution demonstrated that 3E10-D31N had higher accumulation in tumors when compared to 3E10-WT (FIG. 11C).

Figures 12A, 12B, 12C:
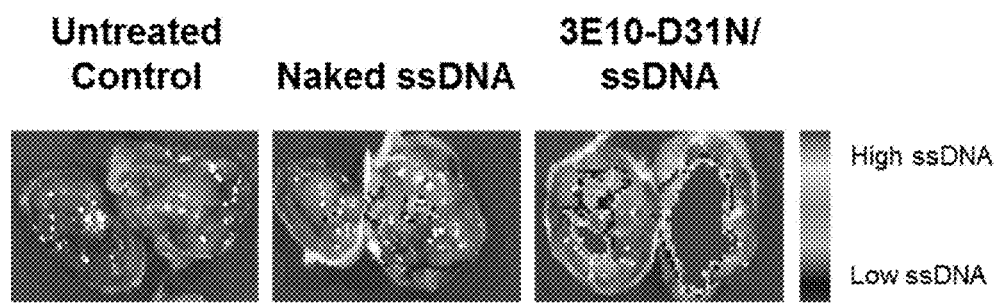
FIGS. 12A, 12B, and 12C are images showing control (FIG. 12A), and distribution of IV Injected naked single stranded DNA (ssDNA) (FIG. 12B) and 3E10-D31N+ssDNA (FIG. 12C) syngeneic colon tumors (CT26), imaged by IVIS (Perkin Elmer) 24 hours after injection.
Figure 12D:
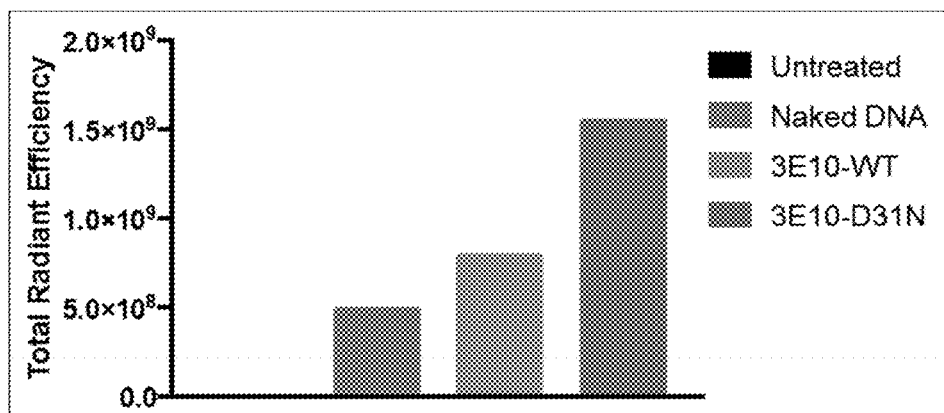
FIG. 12D is a bar graph quantifying the fluorescence in the IVIS images.
Figure 13:
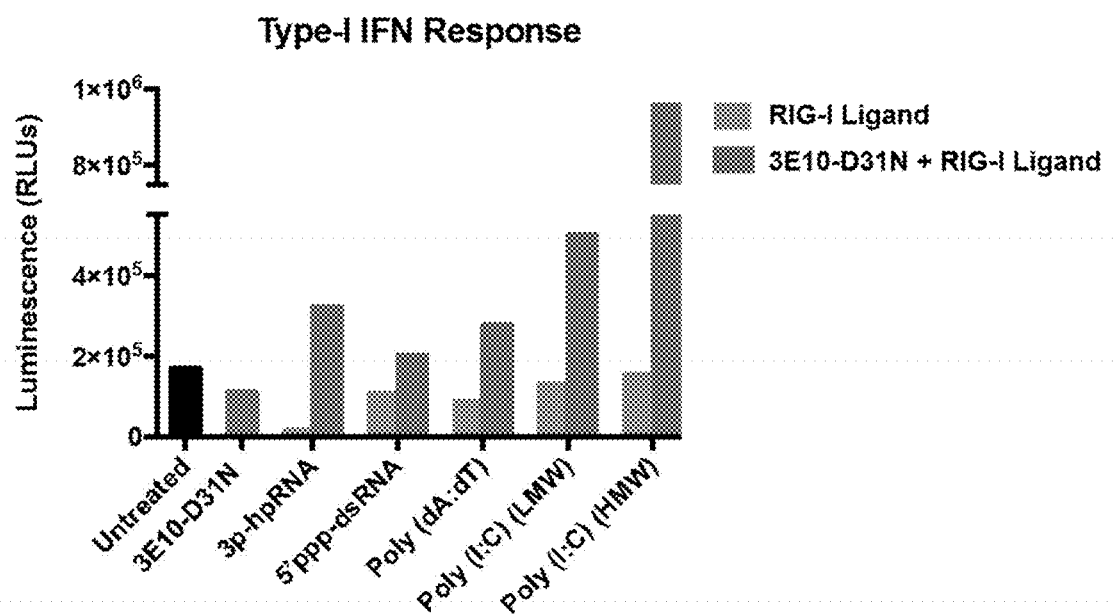
FIG. 13 is a bar graph showing 3E10-mediated delivery and stimulation of RIG-I.

Distribution of ssDNA non-covalently associated with 3E10 was investigated. Mice bearing flank syngeneic colon tumors (CT26) were injected intravenously with 200 ug of 3E10, WT or D31N, mixed with 40 ug of labeled ssDNA (IR680). 24 hours after injection, tumors were harvested and imaged by IVIS (Perkin Elmer) (FIG. 12A-12C). Quantification of tissue distribution demonstrated that delivery of ssDNA by 3E10-D31N resulted in higher tumor accumulation when compared to 3E10-WT (FIG. 12D).

Example 12: 3E10-Mediates Delivery of RIG-I Ligand, and Stimulation of RIG-I Activity Materials and Methods RIG-I reporter cells (HEK-Lucia RIG-I, Invivogen) were seeded at 50,000 cells per well and treated with RIG-I ligands (1 ug) or ligands complexed to 3E10-D31N (20 ug). This assay uses a cell line with a luciferase reporter that is activated when there is induction of interferons.

Results

In all cases, RIG-I ligands alone did not stimulate IFN-γ secretion. Delivery of RIG-ligands with 3E10-D31N, however, stimulated IFN-γ secretion above controls, with the highest secretion observed for poly (I:C), both low and high molecular weight (LMW and HMW).

Example 13: Molecular Modeling of 3E10 and Engineered Variants Thereof

```
WT HEAVY CHAIN scFv SEQUENCE
                                        (SEQ ID NO: 92)
E VQLVESGGGL VKPGGSRKLS CAASGFTFSD YGMHWVRQAP

EKGLEWVAYI SSGSSTIYYA DTVKGRFTIS RDNAKNTLFL

QMTSLRSEDT AMYYCARRGL LLDYWGQGTT LTVS

LIGHT CHAIN scFv SEQUENCE
                                        (SEQ ID NO: 93)
D IVLTQSPASL AVSLGQRATI SCRASKSVST SSYSYMHWYQ

QKPGQPPKLL IKYASYLESG VPARFSGSGS GTDFTLNIHP

VEEEDAATYY CQHSREFPWT FGGGTKLEIK RADAAPGGGG

SGGGGSGGGGS
```

Molecular modeling of 3E10 (Pymol) revealed a putative Nucleic Acid Binding pocket (NAB1) (FIGS. 14A-14B). Mutation of aspartic acid at residue 31 of CDR1 to asparagine increased the cationic charge of this residue and enhanced nucleic acid binding and delivery in vivo (3E10-D31N).

Mutation of aspartic acid at residue 31 of CDR1 to arginine (3E10-D31R), further expanded the cationic charge while mutation to lysine (3E10-D31K) changed charge orientation (FIG. 14A).

NAB1 amino acids predicted from molecular modeling have been underlined in the heavy and light chain sequences above. FIG. 14B is an illustration showing molecular modeling of 3E10-scFv (Pymol) with NAB1 amino acid residues illustrated with punctate dots.

Those skilled in the art will recognize, or be able to ascertain using no more than routine experimentation, many equivalents to the specific embodiments of the invention described herein. Such equivalents are intended to be encompassed by the following claims.

We claim:

1. A method for treating a cancer in a subject in need thereof, the method comprising administering to the subject a therapeutically effective amount of a composition comprising a non-covalent complex of (a) an antibody or antigen-binding fragment thereof, and (b) a therapeutic polynucleotide, wherein the antibody or antigen-binding fragment thereof comprises $V_H$ complementarity determining regions (CDRs) having the amino acid sequences of SEQ ID NO:16, SEQ ID NO:17, and SEQ ID NO:18, and $V_L$ CDRs having the amino acid sequences of SEQ ID NO:24, SEQ ID NO:25, and SEQ ID NO:26;

and wherein the cancer comprises one or more cells that express a functional ENT2 transporter.

2. The method according to claim 1, wherein the antibody or antigen-binding fragment thereof comprises a heavy chain variable region ($V_H$) having an amino acid sequence that is at least 95% identical to SEQ ID NO:2 and a light chain variable region ($V_L$) having an amino acid sequence that is at least 95% identical to SEQ ID NO:7 or 8.

3. The method according to claim 2, wherein the $V_H$ has the amino acid sequence of SEQ ID NO:2 and the $V_L$ has the amino acid sequence of SEQ ID NO:7 or 8.

4. The method according to claim 1, wherein the antibody or antigen-binding fragment thereof comprises a $V_H$ having an amino acid sequence that is at least 95% identical to SEQ ID NO: 6 and a $V_L$ having an amino acid sequence that is at least 95% identical to an amino acid sequence selected from the group consisting of SEQ ID NOs: 11 and 53-55.

5. The method according to claim 4, wherein the $V_H$ has an amino acid sequence of SEQ ID NO: 6 and the $V_L$ has an amino acid sequence selected from the group consisting of SEQ ID NOs: 11 and 53-55.

6. The method according to claim 1, wherein the antibody or antigen-binding fragment thereof is a humanized antibody.

7. The method according to claim 1, wherein the antibody or antigen-binding fragment thereof is a monovalent, divalent, or multivalent single chain variable fragment (scFv).

8. The method according to claim 1, wherein the antibody or antigen-binding fragment thereof is a bispecific antibody.

9. The method according to claim 8, wherein the bispecific antibody comprises:

a first heavy chain or antigen-binding fragment thereof comprising CDRs having the amino acid sequences of SEQ ID NO:16, SEQ ID NO:17, and SEQ ID NO:18, and a first light chain or antigen binding fragment thereof comprising CDRs having the amino acid sequences of SEQ ID NO:24, SEQ ID NO:25, and SEQ ID NO:26; and a second heavy chain, or antigen-binding fragment thereof, and a second light chain, or antigen binding fragment thereof, that associate to specifically bind a target cell-type, tissue, or organ.

10. The method according to claim 1, wherein the therapeutic polynucleotide is a polynucleotide inhibitor of protein translation.

11. The method according to claim 10, wherein the polynucleotide inhibitor of protein translation is an antisense oligonucleotide.

12. The method according to claim 10, wherein the polynucleotide inhibitor of protein translation is selected from the group consisting of an siRNA, an miRNA, a shRNA, and an external guide sequence (EGS).

13. The method according to claim 10, wherein the polynucleotide inhibitor targets mRNA encoding an oncogenic protein.

14. The method according to claim 10, wherein the composition comprises:
- a first complex of (a) an antibody or antigen-binding fragment thereof comprising $V_H$ CDRs having the amino acid sequences of SEQ ID NO:16, SEQ ID NO:17, and SEQ ID NO:18, and $V_L$ CDRs having the amino acid sequences of SEQ ID NO:24, SEQ ID NO:25, and SEQ ID NO:26, and (b) a first polynucleotide inhibitor of protein translation; and
- a second complex of (a) an antibody or antigen-binding fragment thereof comprising $V_H$ CDRs having the amino acid sequences of SEQ ID NO:16, SEQ ID NO:17, and SEQ ID NO:18, and $V_L$ CDRs having the amino acid sequences of SEQ ID NO:24, SEQ ID NO:25, and SEQ ID NO:26, and (b) a second polynucleotide inhibitor of protein translation;
- wherein the first polynucleotide inhibitor of protein translation and the second inhibitor of protein translation are different inhibitors of protein translation.

15. The method according to claim 1, wherein the therapeutic polynucleotide is an mRNA or plasmid.

16. The method according to claim 15, wherein the mRNA encodes a polypeptide ligand for a receptor of an immune cell.

17. The method according to claim 16, wherein the polypeptide ligand stimulates the immune system of the subject.

18. The method according to claim 15, wherein the mRNA encodes an antigen.

19. The method according to claim 18, wherein the antigen is a viral antigen.

20. The method according to claim 1, wherein the cancer is selected from the group consisting of a pancreatic cancer, a skin cancer, a brain cancer, a colorectal cancer, and a breast cancer.

21. The method according to claim 1, wherein the cancer is selected from the group consisting of a vascular cancer, multiple myeloma, an adenocarcinoma, a sarcoma, a bone cancer, a bladder cancer, a cervical cancer, an esophageal cancer, a kidney cancer, a liver cancer, a lung cancer, a nasopharangeal cancer, a prostate cancer, a stomach cancer, and a uterine cancer.

22. The method according to claim 1, wherein the composition further comprises a pharmaceutically acceptable excipient.

* * * * *

SEQUENCE LISTING

```
Sequence total quantity: 93
SEQ ID NO: 1              moltype = AA  length = 116
FEATURE                   Location/Qualifiers
source                    1..116
                          mol_type = protein
                          note = synthetic polypeptide
                          organism = synthetic construct
SEQUENCE: 1
EVQLVESGGG LVKPGGSRKL SCAASGFTFS DYGMHWVRQA PEKGLEWVAY ISSGSSTIYY    60
ADTVKGRFTI SRDNAKNTLF LQMTSLRSED TAMYYCARRG LLLDYWGQGT TLTVSS        116

SEQ ID NO: 2              moltype = AA  length = 116
FEATURE                   Location/Qualifiers
source                    1..116
                          mol_type = protein
                          note = synthetic polypeptide
                          organism = synthetic construct
SEQUENCE: 2
EVQLVESGGG LVKPGGSRKL SCAASGFTFS NYGMHWVRQA PEKGLEWVAY ISSGSSTIYY    60
ADTVKGRFTI SRDNAKNTLF LQMTSLRSED TAMYYCARRG LLLDYWGQGT TLTVSS        116

SEQ ID NO: 3              moltype = AA  length = 116
FEATURE                   Location/Qualifiers
source                    1..116
                          mol_type = protein
                          note = synthetic polypeptide
                          organism = synthetic construct
SEQUENCE: 3
EVQLVQSGGG LIQPGGSLRL SCAASGFTFS NYGMHWVRQA PGKGLEWVSY ISSGSSTIYY    60
ADSVKGRFTI SRDNSKNTLY LQMNSLRAED TAVYYCARRG LLLDYWGQGT TVTVSS        116

SEQ ID NO: 4              moltype = AA  length = 116
FEATURE                   Location/Qualifiers
source                    1..116
                          mol_type = protein
                          note = synthetic polypeptide
                          organism = synthetic construct
SEQUENCE: 4
EVQLVESGGG LIQPGGSLRL SCAASGFTFS NYGMHWVRQA PGKGLEWVSY ISSGSSTIYY    60
ADSVKGRFTI SRDNSKNTLY LQMTSLRAED TAVYYCARRG LLLDYWGQGT TLTVSS        116

SEQ ID NO: 5              moltype = AA  length = 116
FEATURE                   Location/Qualifiers
source                    1..116
                          mol_type = protein
                          note = synthetic polypeptide
                          organism = synthetic construct
SEQUENCE: 5
EVQLQESGGG VVQPGGSLRL SCAASGFTFS NYGMHWIRQA PGKGLEWVSY ISSGSSTIYY    60
ADSVKGRFTI SRDNSKNTLY LQMNSLRSED TAVYYCARRG LLLDYWGQGT LVTVSS        116

SEQ ID NO: 6              moltype = AA  length = 116
FEATURE                   Location/Qualifiers
source                    1..116
                          mol_type = protein
                          note = synthetic polypeptide
                          organism = synthetic construct
SEQUENCE: 6
EVQLVESGGG LVQPGGSLRL SCSASGFTFS NYGMHWVRQA PGKGLEYVSY ISSGSSTIYY    60
ADTVKGRFTI SRDNSKNTLY LQMSSLRAED TAVYYCVKRG LLLDYWGQGT LVTVSS        116

SEQ ID NO: 7              moltype = AA  length = 111
FEATURE                   Location/Qualifiers
source                    1..111
                          mol_type = protein
                          note = synthetic polypeptide
                          organism = synthetic construct
SEQUENCE: 7
DIVLTQSPAS LAVSLGQRAT ISCRASKSVS TSSYSYMHWY QQKPGQPPKL LIKYASYLES    60
GVPARFSGSG SGTDFTLNIH PVEEEDAATY YCQHSREFPW TFGGGTKLEI K             111

SEQ ID NO: 8              moltype = AA  length = 111
FEATURE                   Location/Qualifiers
source                    1..111
                          mol_type = protein
                          note = synthetic polypeptide
                          organism = synthetic construct
SEQUENCE: 8
```

```
DIVLTQSPAS LAVSLGQRAT ISCRASKSVS TSSYSYMHWY QQKPGQPPKL LIKYASYLES    60
GVPARFSGSG SGTDFHLNIH PVEEEDAATY YCQHSREFPW TFGGGTKLEL K            111

SEQ ID NO: 9              moltype = AA  length = 111
FEATURE                   Location/Qualifiers
source                    1..111
                          mol_type = protein
                          note = synthetic polypeptide
                          organism = synthetic construct
SEQUENCE: 9
DIQMTQSPSS LSASVGDRVT ITCRASKSVS TSSYSYLAWY QQKPEKAPKL LIKYASYLQS    60
GVPSRFSGSG SGTDFTLTIS SLQPEDFATY YCQHSREFPW TFGAGTKLEL K            111

SEQ ID NO: 10             moltype = AA  length = 111
FEATURE                   Location/Qualifiers
source                    1..111
                          mol_type = protein
                          note = synthetic polypeptide
                          organism = synthetic construct
SEQUENCE: 10
DIQMTQSPSS LSASVGDRVT ISCRASKSVS TSSYSYMHWY QQKPEKAPKL LIKYASYLQS    60
GVPSRFSGSG SGTDFTLTIS SLQPEDVATY YCQHSREFPW TFGAGTKLEL K            111

SEQ ID NO: 11             moltype = AA  length = 111
FEATURE                   Location/Qualifiers
source                    1..111
                          mol_type = protein
                          note = synthetic polypeptide
                          organism = synthetic construct
SEQUENCE: 11
DIVLTQSPAS LAVSPGQRAT ITCRASKSVS TSSYSYMHWY QQKPGQPPKL LIYYASYLES    60
GVPARFSGSG SGTDFTLTIN PVEANDTANY YCQHSREFPW TFGQGTKVEI K            111

SEQ ID NO: 12             moltype = AA  length = 465
FEATURE                   Location/Qualifiers
source                    1..465
                          mol_type = protein
                          note = synthetic polypeptide
                          organism = synthetic construct
SEQUENCE: 12
MGWSCIILFL VATATGVHSE VQLVESGGGL VKPGGSRKLS CAASGFTFSD YGMHWVRQAP    60
EKGLEWVAYI SSGSSTIYYA DTVKGRFTIS RDNAKNTLFL QMTSLRSEDT AMYYCARRGL   120
LLDYWGQGTT LTVSAASTKG PSVFPLAPSS KSTSGGTAAL GCLVKDYFPE PVTVSWNSGA   180
LTSGVHTFPA VLQSSGLYSL SSVVTVPSSS LGTQTYICNV NHKPSNTKVD KKVEPKSCDK   240
THTCPPCPAP ELLGGPSVFL FPPKPKDTLM ISRTPEVTCV VVDVSHEDPE VKFNWYVDGV   300
EVHNAKTKPR EEQYNSTYRV VSVLTVLHQD WLNGKEYKCK VSNKALPAPI EKTISKAKGQ   360
PREPQVYTLP PSRDELTKNQ VSLTCLVKGF YPSDIAVEWE SNGQPENNYK TTPPVLDSDG   420
SFFLYSKLTV DKSRWQQGNV FSCSVMHEAL HNHYTQKSLS LSPGK                  465

SEQ ID NO: 13             moltype = AA  length = 465
FEATURE                   Location/Qualifiers
source                    1..465
                          mol_type = protein
                          note = synthetic polypeptide
                          organism = synthetic construct
SEQUENCE: 13
MGWSCIILFL VATATGVHSE VQLVESGGGL VKPGGSRKLS CAASGFTFSN YGMHWVRQAP    60
EKGLEWVAYI SSGSSTIYYA DTVKGRFTIS RDNAKNTLFL QMTSLRSEDT AMYYCARRGL   120
LLDYWGQGTT LTVSAASTKG PSVFPLAPSS KSTSGGTAAL GCLVKDYFPE PVTVSWNSGA   180
LTSGVHTFPA VLQSSGLYSL SSVVTVPSSS LGTQTYICNV NHKPSNTKVD KKVEPKSCDK   240
THTCPPCPAP ELLGGPSVFL FPPKPKDTLM ISRTPEVTCV VVDVSHEDPE VKFNWYVDGV   300
EVHNAKTKPR EEQYNSTYRV VSVLTVLHQD WLNGKEYKCK VSNKALPAPI EKTISKAKGQ   360
PREPQVYTLP PSRDELTKNQ VSLTCLVKGF YPSDIAVEWE SNGQPENNYK TTPPVLDSDG   420
SFFLYSKLTV DKSRWQQGNV FSCSVMHEAL HNHYTQKSLS LSPGK                  465

SEQ ID NO: 14             moltype = AA  length = 237
FEATURE                   Location/Qualifiers
source                    1..237
                          mol_type = protein
                          note = synthetic polypeptide
                          organism = synthetic construct
SEQUENCE: 14
MGWSCIILFL VATATGVHSD IVLTQSPASL AVSLGQRATI SCRASKSVST SSYSYMHWYQ    60
QKPGQPPKLL IKYASYLESG VPARFSGSGS GTDFTLNIHP VEEEDAATYY CQHSREFPWT   120
FGGGTKLEIK RTVAAPSVFI FPPSDEQLKS GTASVVCLLN NFYPREAKVQ WKVDNALQSG   180
NSQESVTEQD SKDSTYSLSS TLTLSKADYE KHKVYACEVT HQGLSSPVTK SFNRGEC      237

SEQ ID NO: 15             moltype = AA  length = 5
FEATURE                   Location/Qualifiers
```

```
                        -continued source                  1..5
                        mol_type = protein
                        note = synthetic polypeptide
                        organism = synthetic construct
SEQUENCE: 15
DYGMH                                                                       5

SEQ ID NO: 16           moltype = AA  length = 5
FEATURE                 Location/Qualifiers
source                  1..5
                        mol_type = protein
                        note = synthetic polypeptide
                        organism = synthetic construct
SEQUENCE: 16
NYGMH                                                                       5

SEQ ID NO: 17           moltype = AA  length = 17
FEATURE                 Location/Qualifiers
source                  1..17
                        mol_type = protein
                        note = synthetic polypeptide
                        organism = synthetic construct
SEQUENCE: 17
YISSGSSTIY YADTVKG                                                         17

SEQ ID NO: 18           moltype = AA  length = 7
FEATURE                 Location/Qualifiers
source                  1..7
                        mol_type = protein
                        note = synthetic polypeptide
                        organism = synthetic construct
SEQUENCE: 18
RGLLLDY                                                                     7

SEQ ID NO: 19           moltype = AA  length = 17
FEATURE                 Location/Qualifiers
source                  1..17
                        mol_type = protein
                        note = synthetic polypeptide
                        organism = synthetic construct
SEQUENCE: 19
YISSGSSTIY YADSVKG                                                         17

SEQ ID NO: 20           moltype = AA  length = 8
FEATURE                 Location/Qualifiers
source                  1..8
                        mol_type = protein
                        note = synthetic polypeptide
                        organism = synthetic construct
SEQUENCE: 20
GFTFSDYG                                                                    8

SEQ ID NO: 21           moltype = AA  length = 8
FEATURE                 Location/Qualifiers
source                  1..8
                        mol_type = protein
                        note = synthetic polypeptide
                        organism = synthetic construct
SEQUENCE: 21
GFTFSNYG                                                                    8

SEQ ID NO: 22           moltype = AA  length = 8
FEATURE                 Location/Qualifiers
source                  1..8
                        mol_type = protein
                        note = synthetic polypeptide
                        organism = synthetic construct
SEQUENCE: 22
ISSGSSTI                                                                    8

SEQ ID NO: 23           moltype = AA  length = 9
FEATURE                 Location/Qualifiers
source                  1..9
                        mol_type = protein
                        note = synthetic polypeptide
                        organism = synthetic construct
SEQUENCE: 23
ARRGLLLDY                                                                   9
```

```
SEQ ID NO: 24          moltype = AA   length = 15
FEATURE                Location/Qualifiers
source                 1..15
                       mol_type = protein
                       note = synthetic polypeptide
                       organism = synthetic construct
SEQUENCE: 24
RASKSVSTSS YSYMH                                                          15

SEQ ID NO: 25          moltype = AA   length = 7
FEATURE                Location/Qualifiers
source                 1..7
                       mol_type = protein
                       note = synthetic polypeptide
                       organism = synthetic construct
SEQUENCE: 25
YASYLES                                                                    7

SEQ ID NO: 26          moltype = AA   length = 9
FEATURE                Location/Qualifiers
source                 1..9
                       mol_type = protein
                       note = synthetic polypeptide
                       organism = synthetic construct
SEQUENCE: 26
QHSREFPWT                                                                  9

SEQ ID NO: 27          moltype = AA   length = 15
FEATURE                Location/Qualifiers
source                 1..15
                       mol_type = protein
                       note = synthetic polypeptide
                       organism = synthetic construct
SEQUENCE: 27
RASKSVSTSS YSYLA                                                          15

SEQ ID NO: 28          moltype = AA   length = 7
FEATURE                Location/Qualifiers
source                 1..7
                       mol_type = protein
                       note = synthetic polypeptide
                       organism = synthetic construct
SEQUENCE: 28
YASYLQS                                                                    7

SEQ ID NO: 29          moltype = AA   length = 10
FEATURE                Location/Qualifiers
source                 1..10
                       mol_type = protein
                       note = synthetic polypeptide
                       organism = synthetic construct
SEQUENCE: 29
KSVSTSSYSY                                                                10

SEQ ID NO: 30          moltype =     length =
SEQUENCE: 30
000

SEQ ID NO: 31          moltype = AA   length = 7
FEATURE                Location/Qualifiers
source                 1..7
                       mol_type = protein
                       note = synthetic polypeptide
                       organism = synthetic construct
SEQUENCE: 31
GQSSRSS                                                                    7

SEQ ID NO: 32          moltype = AA   length = 18
FEATURE                Location/Qualifiers
source                 1..18
                       mol_type = protein
                       note = synthetic polypeptide
                       organism = synthetic construct
SEQUENCE: 32
GQSSRSSSGG GSSGGGGS                                                       18

SEQ ID NO: 33          moltype = AA   length = 4
FEATURE                Location/Qualifiers
source                 1..4
```

```
                            mol_type = protein
                            note = synthetic polypeptide
                            organism = synthetic construct
SEQUENCE: 33
GSGS                                                                 4

SEQ ID NO: 34               moltype = AA  length = 4
FEATURE                     Location/Qualifiers
source                      1..4
                            mol_type = protein
                            note = synthetic polypeptide
                            organism = synthetic construct
SEQUENCE: 34
GGGS                                                                 4

SEQ ID NO: 35               moltype = AA  length = 10
FEATURE                     Location/Qualifiers
source                      1..10
                            mol_type = protein
                            note = synthetic polypeptide
                            organism = synthetic construct
SEQUENCE: 35
GGGGSGGGGS                                                          10

SEQ ID NO: 36               moltype = AA  length = 20
FEATURE                     Location/Qualifiers
source                      1..20
                            mol_type = protein
                            note = synthetic polypeptide
                            organism = synthetic construct
SEQUENCE: 36
GGGGSGGGGS GGGGSGGGGS                                               20

SEQ ID NO: 37               moltype = AA  length = 15
FEATURE                     Location/Qualifiers
source                      1..15
                            mol_type = protein
                            note = synthetic polypeptide
                            organism = synthetic construct
SEQUENCE: 37
GGGGSGGGGS GGGGS                                                    15

SEQ ID NO: 38               moltype = AA  length = 274
FEATURE                     Location/Qualifiers
source                      1..274
                            mol_type = protein
                            note = synthetic polypeptide
                            organism = synthetic construct
SEQUENCE: 38
AGIHDIVLTQ SPASLAVSLG QRATISCRAS KSVSTSSYSY MHWYQQKPGQ PPKLLIKYAS    60
YLESGVPARF SGSGSGTDFT LNIHPVEEED AATYYCQHSR EFPWTFGGGT KLEIKRADAA   120
PGGGGSGGGG SGGGGSEVQL VESGGGLVKP GGSRKLSCAA SGFTFSNYGM HWVRQAPEKG   180
LEWVAYISSG SSTIYYADTV KGRFTISRDN AKNTLFLQMT SLRSEDTAMY YCARRGLLLD   240
YWGQGTTLTV SSLEQKLISE EDLNSAVDHH HHHH                              274

SEQ ID NO: 39               moltype = AA  length = 541
FEATURE                     Location/Qualifiers
source                      1..541
                            mol_type = protein
                            note = synthetic polypeptide
                            organism = synthetic construct
SEQUENCE: 39
AGIHDIVLTQ SPASLAVSLG QRATISCRAS KSVSTSSYSY MHWYQQKPGQ PPKLLIKYAS    60
YLESGVPARF SGSGSGTDFT LNIHPVEEED AATYYCQHSR EFPWTFGGGT KLEIKRADAA   120
PGGGGSGGGG SGGGGSEVQL VESGGGLVKP GGSRKLSCAA SGFTFSNYGM HWVRQAPEKG   180
LEWVAYISSG SSTIYYADTV KGRFTISRDN AKNTLFLQMT SLRSEDTAMY YCARRGLLLD   240
YWGQGTTLTV SSASTKGPSV FPLAPLESSG SDIVLTQSPA SLAVSLGQRA TISCRASKSV   300
STSSYSYMHW YQQKPGQPPK LLIKYASYLE SGVPARFSGS GSGTDFTLNI HPVEEEDAAT   360
YYCQHSREFP WTFGGGTKLE IKRADAAPGG GGSGGGGSGG GGSEVQLVES GGGLVKPGGS   420
RKLSCAASGF TFSNYGMHWV RQAPEKGLEW VAYISSGSST IYYADTVKGR FTISRDNAKN   480
TLFLQMTSLR SEDTAMYYCA RRGLLLDYWG QGTTLTVSSL EQKLISEEDL NSAVDHHHHH   540
H                                                                  541

SEQ ID NO: 40               moltype = AA  length = 808
FEATURE                     Location/Qualifiers
source                      1..808
                            mol_type = protein
                            note = synthetic polypeptide
                            organism = synthetic construct
```

```
SEQUENCE: 40
AGIHDIVLTQ SPASLAVSLG QRATISCRAS KSVSTSSYSY MHWYQQKPGQ PPKLLIKYAS    60
YLESGVPARF SGSGSGTDFT LNIHPVEEED AATYYCQHSR EFPWTFGGGT KLEIKRADAA   120
PGGGGSGGGG SGGGGSEVQL VESGGGLVKP GGSRKLSCAA SGFTFSNYGM HWVRQAPEKG   180
LEWVAYISSG SSTIYYADTV KGRFTISRDN AKNTLFLQMT SLRSEDTAMY YCARRGLLLD   240
YWGQGTTLTV SSASTKGPSV FPLAPLESSG SDIVLTQSPA SLAVSLGQRA TISCRASKSV   300
STSSYSYMHW YQQKPGQPPK LLIKYASYLE SGVPARFSGS GSGTDFTLNI HPVEEEDAAT   360
YYCQHSREFP WTFGGGTKLE IKRADAAPGG GGSGGGGSGG GGSEVQLVES GGGLVKPGGS   420
RKLSCAASGF TFSNYGMHWV RQAPEKGLEW VAYISSGSST IYYADTVKGR FTISRDNAKN   480
TLFLQMTSLR SEDTAMYYCA RRGLLLDYWG QGTTLTVSSA STKGPSVFPL APLESSGSDI   540
VLTQSPASLA VSLGQRATIS CRASKSVSTS SYSYMHWYQQ KPGQPPKLLI KYASYLESGV   600
PARFSGSGSG TDFTLNIHPV EEEDAATYYC QHSREFPWTF GGGTKLEIKR ADAAPGGGGS   660
GGGGSGGGGS EVQLVESGGG LVKPGGSRKL SCAASGFTFS NYGMHWVRQA PEKGLEWVAY   720
ISSGSSTIYY ADTVKGRFTI SRDNAKNTLF LQMTSLRSED TAMYYCARRG LLLDYWGQGT   780
TLTVSSLEQK LISEEDLNSA VDHHHHHH                                      808

SEQ ID NO: 41            moltype = AA   length = 242
FEATURE                  Location/Qualifiers
source                   1..242
                         mol_type = protein
                         note = synthetic polypeptide
                         organism = synthetic construct
SEQUENCE: 41
DIVLTQSPAS LAVSPGQRAT ITCRASKSVS TSSYSYMHWY QQKPGQPPKL LIYYASYLES    60
GVPARFSGSG SGTDFTLTIN PVEANDTANY YCQHSREFPW TFGQGTKVEI KGGGGSGGGG   120
SGGGGSEVQL VESGGGLVQP GGSLRLSCSA SGFTFSNYGM HWVRQAPGKG LEYVSYISSG   180
SSTIYYADTV KGRFTISRDN SKNTLYLQMS SLRAEDTAVY YCVKRGLLLD YWGQGTLVTV   240
SS                                                                  242

SEQ ID NO: 42            moltype = AA   length = 17
FEATURE                  Location/Qualifiers
source                   1..17
                         mol_type = protein
                         note = synthetic polypeptide
                         organism = synthetic construct
SEQUENCE: 42
YISSSSSTIY YADSVKG                                                   17

SEQ ID NO: 43            moltype = AA   length = 8
FEATURE                  Location/Qualifiers
source                   1..8
                         mol_type = protein
                         note = synthetic polypeptide
                         organism = synthetic construct
SEQUENCE: 43
ISSSSSTI                                                              8

SEQ ID NO: 44            moltype = AA   length = 15
FEATURE                  Location/Qualifiers
source                   1..15
                         mol_type = protein
                         note = synthetic polypeptide
                         organism = synthetic construct
SEQUENCE: 44
RASKTVSTSS YSYMH                                                     15

SEQ ID NO: 45            moltype = AA   length = 10
FEATURE                  Location/Qualifiers
source                   1..10
                         mol_type = protein
                         note = synthetic polypeptide
                         organism = synthetic construct
SEQUENCE: 45
KTVSTSSYSY                                                           10

SEQ ID NO: 46            moltype = AA   length = 116
FEATURE                  Location/Qualifiers
source                   1..116
                         mol_type = protein
                         note = synthetic polypeptide
                         organism = synthetic construct
SEQUENCE: 46
EVQLVESGGG LVQPGGSLRL SCAASGFTFS NYGMHWVRQA PGKGLEWVSY ISSSSSTIYY    60
ADSVKGRFTI SRDNAKNSLY LQMNSLRAED TAVYYCARRG LLLDYWGQGT TVTVSS       116

SEQ ID NO: 47            moltype = AA   length = 116
FEATURE                  Location/Qualifiers
source                   1..116
                         mol_type = protein
```

```
                          note = synthetic polypeptide
                          organism = synthetic construct
SEQUENCE: 47
EVQLVESGGG VVQPGGSLRL SCAASGFTFS NYGMHWVRQA PEKGLEWVSY ISSSSSTIYY    60
ADSVKGRFTI SRDNSKNTLY LQMNSLRAED TAVYYCARRG LLLDYWGQGT TVTVSS       116

SEQ ID NO: 48             moltype = AA  length = 116
FEATURE                   Location/Qualifiers
source                    1..116
                          mol_type = protein
                          note = synthetic polypeptide
                          organism = synthetic construct
SEQUENCE: 48
EVQLVESGGG DVKPGGSLRL SCAASGFTFS NYGMHWVRQA PEKGLEWVSY ISSSSSTIYY    60
ADSVKGRFTI SRDNSKNTLY LQMNSLRAED TAVYYCARRG LLLDYWGQGT TVTVSS       116

SEQ ID NO: 49             moltype =    length =
SEQUENCE: 49
000

SEQ ID NO: 50             moltype = AA  length = 116
FEATURE                   Location/Qualifiers
source                    1..116
                          mol_type = protein
                          note = synthetic polypeptide
                          organism = synthetic construct
SEQUENCE: 50
EVQLVESGGG LVQPGGSLRL SCAASGFTFS NYGMHWVRQA PGKGLEWVSY ISSGSSTIYY    60
ADSVKGRFTI SRDNAKNSLY LQMNSLRAED TAVYYCARRG LLLDYWGQGT TVTVSS       116

SEQ ID NO: 51             moltype = AA  length = 116
FEATURE                   Location/Qualifiers
source                    1..116
                          mol_type = protein
                          note = synthetic polypeptide
                          organism = synthetic construct
SEQUENCE: 51
EVQLVESGGG VVQPGGSLRL SCAASGFTFS NYGMHWVRQA PEKGLEWVSY ISSGSSTIYY    60
ADSVKGRFTI SRDNSKNTLY LQMNSLRAED TAVYYCARRG LLLDYWGQGT TVTVSS       116

SEQ ID NO: 52             moltype = AA  length = 116
FEATURE                   Location/Qualifiers
source                    1..116
                          mol_type = protein
                          note = synthetic polypeptide
                          organism = synthetic construct
SEQUENCE: 52
EVQLVESGGG DVKPGGSLRL SCAASGFTFS NYGMHWVRQA PEKGLEWVSY ISSGSSTIYY    60
ADSVKGRFTI SRDNSKNTLY LQMNSLRAED TAVYYCARRG LLLDYWGQGT TVTVSS       116

SEQ ID NO: 53             moltype = AA  length = 111
FEATURE                   Location/Qualifiers
source                    1..111
                          mol_type = protein
                          note = synthetic polypeptide
                          organism = synthetic construct
SEQUENCE: 53
DIQMTQSPSS LSASLGDRAT ITCRASKSVS TSSYSYMHWY QQKPGQPPKL LIKYASYLES    60
GVPSRFSGSG SGTDFTLTIS SLQPEDAATY YCQHSREFPW TFGGGTKVEI K           111

SEQ ID NO: 54             moltype = AA  length = 111
FEATURE                   Location/Qualifiers
source                    1..111
                          mol_type = protein
                          note = synthetic polypeptide
                          organism = synthetic construct
SEQUENCE: 54
DIQMTQSPSS LSASLGDRAT ITCRASKSVS TSSYSYMHWY QQKPGQAPKL LIKYASYLES    60
GVPSRFSGSG SGTDFTLTIS SLQPEDFATY YCQHSREFPW TFGQGTKVEI K           111

SEQ ID NO: 55             moltype = AA  length = 111
FEATURE                   Location/Qualifiers
source                    1..111
                          mol_type = protein
                          note = synthetic polypeptide
                          organism = synthetic construct
SEQUENCE: 55
DIQMTQSPSS LSASVGDRVT ITCRASKSVS TSSYSYMHWY QQKPGKAPKL LIKYASYLES    60
GVPSRFSGSG SGTDFTLTIS SLQPEDFATY YCQHSREFPW TFGQGTKVEI K           111
```

```
SEQ ID NO: 56          moltype = AA  length = 111
FEATURE                Location/Qualifiers
source                 1..111
                       mol_type = protein
                       note = synthetic polypeptide
                       organism = synthetic construct
SEQUENCE: 56
DIQMTQSPSS LSASLGDRAT ITCRASKTVS TSSYSYMHWY QQKPGQPPKL LIKYASYLES    60
GVPSRFSGSG SGTDFTLTIS SLQPEDAATY YCQHSREFPW TFGGGTKVEI K            111

SEQ ID NO: 57          moltype = AA  length = 111
FEATURE                Location/Qualifiers
source                 1..111
                       mol_type = protein
                       note = synthetic polypeptide
                       organism = synthetic construct
SEQUENCE: 57
DIQMTQSPSS LSASVGDRVT ITCRASKTVS TSSYSYMHWY QQKPGKAPKL LIKYASYLES    60
GVPSRFSGSG SGTDFTLTIS SLQPEDFATY YCQHSREFPW TFGQGTKVEI K            111

SEQ ID NO: 58          moltype = AA  length = 111
FEATURE                Location/Qualifiers
source                 1..111
                       mol_type = protein
                       note = synthetic polypeptide
                       organism = synthetic construct
SEQUENCE: 58
DIQMTQSPSS LSASLGDRAT ITCRASKTVS TSSYSYMHWY QQKPGQAPKL LIKYASYLES    60
GVPSRFSGSG SGTDFTLTIS SLQPEDFATY YCQHSREFPW TFGQGTKVEI K            111

SEQ ID NO: 59          moltype = AA  length = 21
FEATURE                Location/Qualifiers
source                 1..21
                       mol_type = protein
                       note = synthetic polypeptide
                       organism = synthetic construct
SEQUENCE: 59
RADAAPGGGG SGGGGSGGGG S                                              21

SEQ ID NO: 60          moltype = AA  length = 19
FEATURE                Location/Qualifiers
source                 1..19
                       mol_type = protein
                       note = synthetic polypeptide
                       organism = synthetic construct
SEQUENCE: 60
ASTKGPSVFP LAPLESSGS                                                 19

SEQ ID NO: 61          moltype = AA  length = 515
FEATURE                Location/Qualifiers
source                 1..515
                       mol_type = protein
                       note = synthetic polypeptide
                       organism = synthetic construct
SEQUENCE: 61
DIQMTQSPSS LSASLGDRAT ITCRASKSVS TSSYSYMHWY QQKPGQPPKL LIKYASYLES    60
GVPSRFSGSG SGTDFTLTIS SLQPEDAATY YCQHSREFPW TFGGGTKVEI KRADAAPGGG   120
GSGGGGSGGG GSEVQLVESG GGLVQPGGSL RLSCAASGFT FSNYGMHWVR QAPGKGLEWV   180
SYISSSSSTI YYADSVKGRF TISRDNAKNS LYLQMNSLRA EDTAVYYCAR RGLLLDYWGQ   240
GTTVTVSSAS TKGPSVFPLA PLESSGSDIQ MTQSPSSLSA SLGDRATITC RASKSVSTSS   300
YSYMHWYQQK PGQPPKLLIK YASYLESGVP SRFSGSGSGT DFTLTISSLQ PEDAATYYCQ   360
HSREFPWTFG GGTKVEIKRA DAAPGGGGSG GGGSGGGGSE VQLVESGGGL VQPGGSLRLS   420
CAASGFTFSN YGMHWVRQAP GKGLEWVSYI SSSSSTIYYA DSVKGRFTIS RDNAKNSLYL   480
QMNSLRAEDT AVYYCARRGL LLDYWGQGTT VTVSS                              515

SEQ ID NO: 62          moltype = AA  length = 515
FEATURE                Location/Qualifiers
source                 1..515
                       mol_type = protein
                       note = synthetic polypeptide
                       organism = synthetic construct
SEQUENCE: 62
DIQMTQSPSS LSASLGDRAT ITCRASKSVS TSSYSYMHWY QQKPGQPPKL LIKYASYLES    60
GVPSRFSGSG SGTDFTLTIS SLQPEDAATY YCQHSREFPW TFGGGTKVEI KRADAAPGGG   120
GSGGGGSGGG GSEVQLVESG GGVVQPGGSL RLSCAASGFT FSNYGMHWVR QAPEKGLEWV   180
SYISSSSSTI YYADSVKGRF TISRDNSKNT LYLQMNSLRA EDTAVYYCAR RGLLLDYWGQ   240
GTTVTVSSAS TKGPSVFPLA PLESSGSDIQ MTQSPSSLSA SLGDRATITC RASKSVSTSS   300
YSYMHWYQQK PGQPPKLLIK YASYLESGVP SRFSGSGSGT DFTLTISSLQ PEDAATYYCQ   360
```

```
HSREFPWTFG GGTKVEIKRA DAAPGGGGSG GGGGSGGGSE VQLVESGGGV VQPGGSLRLS    420
CAASGFTFSN YGMHWVRQAP EKGLEWVSYI SSSSSTIYYA DSVKGRFTIS RDNSKNTLYL    480
QMNSLRAEDT AVYYCARRGL LLDYWGQGTT VTVSS                               515

SEQ ID NO: 63              moltype = AA   length = 515
FEATURE                    Location/Qualifiers
source                     1..515
                           mol_type = protein
                           note = synthetic polypeptide
                           organism = synthetic construct
SEQUENCE: 63
DIQMTQSPSS LSASLGDRAT ITCRASKSVS TSSYSYMHWY QQKPGQPPKL LIKYASYLES    60
GVPSRFSGSS SGTDFTLTIS SLQPEDAATY YCQHSREFPW TFGGGTKVEI KRADAAPGGG    120
GSGGGGGSGG GSEVQLVESG GDVKPGGSL RLSCAASGFT FSNYGMHWVR QAPEKGLEWV     180
SYISSSSSTI YYADSVKGRF TISRDNSKNT LYLQMNSLRA EDTAVYYCAR RGLLLDYWGQ    240
GTTVTVSSAS TKGPSVFPLA PLESSGSDIQ MTQSPSSLSA SLGDRATITC RASKSVSTSS    300
YSYMHWYQQK PGQPPKLLIK YASYLESGVP SRFSGSGSGT DFTLTISSLQ PEDAATYYCQ    360
HSREFPWTFG GGTKVEIKRA DAAPGGGGSG GGGGSGGGSE VQLVESGGGV VQPGGSLRLS    420
CAASGFTFSN YGMHWVRQAP EKGLEWVSYI SSSSSTIYYA DSVKGRFTIS RDNSKNTLYL    480
QMNSLRAEDT AVYYCARRGL LLDYWGQGTT VTVSS                               515

SEQ ID NO: 64              moltype = AA   length = 515
FEATURE                    Location/Qualifiers
source                     1..515
                           mol_type = protein
                           note = synthetic polypeptide
                           organism = synthetic construct
SEQUENCE: 64
DIQMTQSPSS LSASLGDRAT ITCRASKSVS TSSYSYMHWY QQKPGQAPKL LIKYASYLES    60
GVPSRFSGSG SGTDFTLTIS SLQPEDFATY YCQHSREFPW TFGQGTKVEI KRADAAPGGG    120
GSGGGGSGGG GSEVQLVESG GLVQPGGSL RLSCAASGFT FSNYGMHWVR QAPGKGLEWV     180
SYISSSSSTI YYADSVKGRF TISRDNAKNS LYLQMNSLRA EDTAVYYCAR RGLLLDYWGQ    240
GTTVTVSSAS TKGPSVFPLA PLESSGSDIQ MTQSPSSLSA SLGDRATITC RASKSVSTSS    300
YSYMHWYQQK PGQAPKLLIK YASYLESGVP SRFSGSGSGT DFTLTISSLQ PEDFATYYCQ    360
HSREFPWTFG QGTKVEIKRA DAAPGGGGSG GGGSGGGGSE VQLVESGGGL VQPGGSLRLS    420
CAASGFTFSN YGMHWVRQAP GKGLEWVSYI SSSSSTIYYA DSVKGRFTIS RDNAKNSLYL    480
QMNSLRAEDT AVYYCARRGL LLDYWGQGTT VTVSS                               515

SEQ ID NO: 65              moltype = AA   length = 515
FEATURE                    Location/Qualifiers
source                     1..515
                           mol_type = protein
                           note = synthetic polypeptide
                           organism = synthetic construct
SEQUENCE: 65
DIQMTQSPSS LSASLGDRAT ITCRASKSVS TSSYSYMHWY QQKPGQAPKL LIKYASYLES    60
GVPSRFSGSG SGTDFTLTIS SLQPEDFATY YCQHSREFPW TFGQGTKVEI KRADAAPGGG    120
GSGGGGSGGG GSEVQLVESG GVVQPGGSL RLSCAASGFT FSNYGMHWVR QAPEKGLEWV     180
SYISSSSSTI YYADSVKGRF TISRDNSKNT LYLQMNSLRA EDTAVYYCAR RGLLLDYWGQ    240
GTTVTVSSAS TKGPSVFPLA PLESSGSDIQ MTQSPSSLSA SLGDRATITC RASKSVSTSS    300
YSYMHWYQQK PGQAPKLLIK YASYLESGVP SRFSGSGSGT DFTLTISSLQ PEDFATYYCQ    360
HSREFPWTFG QGTKVEIKRA DAAPGGGGSG GGGSGGGGSE VQLVESGGGV VQPGGSLRLS    420
CAASGFTFSN YGMHWVRQAP EKGLEWVSYI SSSSSTIYYA DSVKGRFTIS RDNSKNTLYL    480
QMNSLRAEDT AVYYCARRGL LLDYWGQGTT VTVSS                               515

SEQ ID NO: 66              moltype = AA   length = 515
FEATURE                    Location/Qualifiers
source                     1..515
                           mol_type = protein
                           note = synthetic polypeptide
                           organism = synthetic construct
SEQUENCE: 66
DIQMTQSPSS LSASLGDRAT ITCRASKSVS TSSYSYMHWY QQKPGQAPKL LIKYASYLES    60
GVPSRFSGSG SGTDFTLTIS SLQPEDFATY YCQHSREFPW TFGQGTKVEI KRADAAPGGG    120
GSGGGGSGGG GSEVQLVESG GDVKPGGSL RLSCAASGFT FSNYGMHWVR QAPEKGLEWV     180
SYISSSSSTI YYADSVKGRF TISRDNSKNT LYLQMNSLRA EDTAVYYCAR RGLLLDYWGQ    240
GTTVTVSSAS TKGPSVFPLA PLESSGSDIQ MTQSPSSLSA SLGDRATITC RASKSVSTSS    300
YSYMHWYQQK PGQAPKLLIK YASYLESGVP SRFSGSGSGT DFTLTISSLQ PEDFATYYCQ    360
HSREFPWTFG QGTKVEIKRA DAAPGGGGSG GGGSGGGGSE VQLVESGGGD VKPGGSLRLS    420
CAASGFTFSN YGMHWVRQAP EKGLEWVSYI SSSSSTIYYA DSVKGRFTIS RDNSKNTLYL    480
QMNSLRAEDT AVYYCARRGL LLDYWGQGTT VTVSS                               515

SEQ ID NO: 67              moltype = AA   length = 515
FEATURE                    Location/Qualifiers
source                     1..515
                           mol_type = protein
                           note = synthetic polypeptide
                           organism = synthetic construct
SEQUENCE: 67
```

```
DIQMTQSPSS LSASVGDRVT ITCRASKSVS TSSYSYMHWY QQKPGKAPKL LIKYASYLES    60
GVPSRFSGSG SGTDFTLTIS SLQPEDFATY YCQHSREFPW TFGQGTKVEI KRADAAPGGG   120
GSGGGGSGGG GSEVQLVESG GGLVQPGGSL RLSCAASGFT FSNYGMHWVR QAPGKGLEWV   180
SYISSSSSTI YYADSVKGRF TISRDNAKNS LYLQMNSLRA EDTAVYYCAR RGLLLDYWGQ   240
GTTVTVSSAS TKGPSVFPLA PLESSGSDIQ MTQSPSSLSA SVGDRVTITC RASKSVSTSS   300
YSYMHWYQQK PGKAPKLLIK YASYLESGVP SRFSGSGSGT DFTLTISSLQ PEDFATYYCQ   360
HSREFPWTFG QGTKVEIKRA DAAPGGGGSG GGGSGGGGSE VQLVESGGGL VQPGGSLRLS   420
CAASGFTFSN YGMHWVRQAP GKGLEWVSYI SSSSSTIYYA DSVKGRFTIS RDNAKNSLYL   480
QMNSLRAEDT AVYYCARRGL LLDYWGQGTT VTVSS                              515

SEQ ID NO: 68           moltype = AA  length = 515
FEATURE                 Location/Qualifiers
source                  1..515
                        mol_type = protein
                        note = synthetic polypeptide
                        organism = synthetic construct
SEQUENCE: 68
DIQMTQSPSS LSASVGDRVT ITCRASKSVS TSSYSYMHWY QQKPGKAPKL LIKYASYLES    60
GVPSRFSGSG SGTDFTLTIS SLQPEDFATY YCQHSREFPW TFGQGTKVEI KRADAAPGGG   120
GSGGGGSGGG GSEVQLVESG GVVQPGGSL RLSCAASGFT FSNYGMHWVR QAPEKGLEWV   180
SYISSSSSTI YYADSVKGRF TISRDNSKNT LYLQMNSLRA EDTAVYYCAR RGLLLDYWGQ   240
GTTVTVSSAS TKGPSVFPLA PLESSGSDIQ MTQSPSSLSA SVGDRVTITC RASKSVSTSS   300
YSYMHWYQQK PGKAPKLLIK YASYLESGVP SRFSGSGSGT DFTLTISSLQ PEDFATYYCQ   360
HSREFPWTFG QGTKVEIKRA DAAPGGGGSG GGGSGGGGSE VQLVESGGGV VQPGGSLRLS   420
CAASGFTFSN YGMHWVRQAP EKGLEWVSYI SSSSSTIYYA DSVKGRFTIS RDNSKNTLYL   480
QMNSLRAEDT AVYYCARRGL LLDYWGQGTT VTVSS                              515

SEQ ID NO: 69           moltype = AA  length = 515
FEATURE                 Location/Qualifiers
source                  1..515
                        mol_type = protein
                        note = synthetic polypeptide
                        organism = synthetic construct
SEQUENCE: 69
DIQMTQSPSS LSASVGDRVT ITCRASKSVS TSSYSYMHWY QQKPGKAPKL LIKYASYLES    60
GVPSRFSGSG SGTDFTLTIS SLQPEDFATY YCQHSREFPW TFGQGTKVEI KRADAAPGGG   120
GSGGGGSGGG GSEVQLVESG GDVKPGGSL RLSCAASGFT FSNYGMHWVR QAPEKGLEWV   180
SYISSSSSTI YYADSVKGRF TISRDNSKNT LYLQMNSLRA EDTAVYYCAR RGLLLDYWGQ   240
GTTVTVSSAS TKGPSVFPLA PLESSGSDIQ MTQSPSSLSA SVGDRVTITC RASKSVSTSS   300
YSYMHWYQQK PGKAPKLLIK YASYLESGVP SRFSGSGSGT DFTLTISSLQ PEDFATYYCQ   360
HSREFPWTFG QGTKVEIKRA DAAPGGGGSG GGGSGGGGSE VQLVESGGGD VKPGGSLRLS   420
CAASGFTFSN YGMHWVRQAP EKGLEWVSYI SSSSSTIYYA DSVKGRFTIS RDNSKNTLYL   480
QMNSLRAEDT AVYYCARRGL LLDYWGQGTT VTVSS                              515

SEQ ID NO: 70           moltype = AA  length = 515
FEATURE                 Location/Qualifiers
source                  1..515
                        mol_type = protein
                        note = synthetic polypeptide
                        organism = synthetic construct
SEQUENCE: 70
DIQMTQSPSS LSASLGDRAT ITCRASKTVS TSSYSYMHWY QQKPGQPPKL LIKYASYLES    60
GVPSRFSGSG SGTDFTLTIS SLQPEDAATY YCQHSREFPW TFGGGTKVEI KRADAAPGGG   120
GSGGGGSGGG GSEVQLVESG GGLVQPGGSL RLSCAASGFT FSNYGMHWVR QAPGKGLEWV   180
SYISSGSSTI YYADSVKGRF TISRDNAKNS LYLQMNSLRA EDTAVYYCAR RGLLLDYWGQ   240
GTTVTVSSAS TKGPSVFPLA PLESSGSDIQ MTQSPSSLSA SLGDRATITC RASKTVSTSS   300
YSYMHWYQQK PGQPPKLLIK YASYLESGVP SRFSGSGSGT DFTLTISSLQ PEDAATYYCQ   360
HSREFPWTFG GGTKVEIKRA DAAPGGGGSG GGGSGGGGSE VQLVESGGGL VQPGGSLRLS   420
CAASGFTFSN YGMHWVRQAP GKGLEWVSYI SSGSSTIYYA DSVKGRFTIS RDNAKNSLYL   480
QMNSLRAEDT AVYYCARRGL LLDYWGQGTT VTVSS                              515

SEQ ID NO: 71           moltype = AA  length = 515
FEATURE                 Location/Qualifiers
source                  1..515
                        mol_type = protein
                        note = synthetic polypeptide
                        organism = synthetic construct
SEQUENCE: 71
DIQMTQSPSS LSASLGDRAT ITCRASKTVS TSSYSYMHWY QQKPGQPPKL LIKYASYLES    60
GVPSRFSGSG SGTDFTLTIS SLQPEDAATY YCQHSREFPW TFGGGTKVEI KRADAAPGGG   120
GSGGGGSGGG GSEVQLVESG GVVQPGGSL RLSCAASGFT FSNYGMHWVR QAPEKGLEWV   180
SYISSGSSTI YYADSVKGRF TISRDNSKNT LYLQMNSLRA EDTAVYYCAR RGLLLDYWGQ   240
GTTVTVSSAS TKGPSVFPLA PLESSGSDIQ MTQSPSSLSA SLGDRATITC RASKTVSTSS   300
YSYMHWYQQK PGQPPKLLIK YASYLESGVP SRFSGSGSGT DFTLTISSLQ PEDAATYYCQ   360
HSREFPWTFG GGTKVEIKRA DAAPGGGGSG GGGSGGGGSE VQLVESGGGV VQPGGSLRLS   420
CAASGFTFSN YGMHWVRQAP EKGLEWVSYI SSGSSTIYYA DSVKGRFTIS RDNSKNTLYL   480
QMNSLRAEDT AVYYCARRGL LLDYWGQGTT VTVSS                              515

SEQ ID NO: 72           moltype = AA  length = 515
```

```
FEATURE                 Location/Qualifiers
source                  1..515
                        mol_type = protein
                        note = synthetic polypeptide
                        organism = synthetic construct
SEQUENCE: 72
DIQMTQSPSS LSASLGDRAT ITCRASKTVS TSSYSYMHWY QQKPGQPPKL LIKYASYLES     60
GVPSRFSGSG SGTDFTLTIS SLQPEDAATY YCQHSREFPW TFGGGTKVEI KRADAAPGGG    120
GSGGGGSGGG GSEVQLVESG GGDVKPGGSL RLSCAASGFT FSNYGMHWVR QAPEKGLEWV    180
SYISSGSSTI YYADSVKGRF TISRDNSKNT LYLQMNSLRA EDTAVYYCAR RGLLLDYWGQ    240
GTTVTVSSAS TKGPSVFPLA PLESSGSDIQ MTQSPSSLSA SLGDRATITC RASKTVSTSS    300
YSYMHWYQQK PGQPPKLLIK YASYLESGVP SRFSGSGSGT DFTLTISSLQ PEDAATYYCQ    360
HSREFPWTFG GGTKVEIKRA DAAPGGGGSG GGGSGGGGSE VQLVESGGGD VKPGGSLRLS    420
CAASGFTFSN YGMHWVRQAP EKGLEWVSYI SSGSSTIYYA DSVKGRFTIS RDNSKNTLYL    480
QMNSLRAEDT AVYYCARRGL LLDYWGQGTT VTVSS                              515

SEQ ID NO: 73           moltype = AA  length = 515
FEATURE                 Location/Qualifiers
source                  1..515
                        mol_type = protein
                        note = synthetic polypeptide
                        organism = synthetic construct
SEQUENCE: 73
DIQMTQSPSS LSASVGDRVT ITCRASKTVS TSSYSYMHWY QQKPGKAPKL LIKYASYLES     60
GVPSRFSGSG SGTDFTLTIS SLQPEDFATY YCQHSREFPW TFGQGTKVEI KRADAAPGGG    120
GSGGGGSGGG GSEVQLVESG GGLVQPGGSL RLSCAASGFT FSNYGMHWVR QAPGKGLEWV    180
SYISSGSSTI YYADSVKGRF TISRDNAKNS LYLQMNSLRA EDTAVYYCAR RGLLLDYWGQ    240
GTTVTVSSAS TKGPSVFPLA PLESSGSDIQ MTQSPSSLSA SVGDRVTITC RASKTVSTSS    300
YSYMHWYQQK PGKAPKLLIK YASYLESGVP SRFSGSGSGT DFTLTISSLQ PEDFATYYCQ    360
HSREFPWTFG QGTKVEIKRA DAAPGGGGSG GGGSGGGGSE VQLVESGGGL VQPGGSLRLS    420
CAASGFTFSN YGMHWVRQAP GKGLEWVSYI SSGSSTIYYA DSVKGRFTIS RDNAKNSLYL    480
QMNSLRAEDT AVYYCARRGL LLDYWGQGTT VTVSS                              515

SEQ ID NO: 74           moltype = AA  length = 515
FEATURE                 Location/Qualifiers
source                  1..515
                        mol_type = protein
                        note = synthetic polypeptide
                        organism = synthetic construct
SEQUENCE: 74
DIQMTQSPSS LSASVGDRVT ITCRASKTVS TSSYSYMHWY QQKPGKAPKL LIKYASYLES     60
GVPSRFSGSG SGTDFTLTIS SLQPEDFATY YCQHSREFPW TFGQGTKVEI KRADAAPGGG    120
GSGGGGSGGG GSEVQLVESG GGVVQPGGSL RLSCAASGFT FSNYGMHWVR QAPEKGLEWV    180
SYISSGSSTI YYADSVKGRF TISRDNSKNT LYLQMNSLRA EDTAVYYCAR RGLLLDYWGQ    240
GTTVTVSSAS TKGPSVFPLA PLESSGSDIQ MTQSPSSLSA SVGDRVTITC RASKTVSTSS    300
YSYMHWYQQK PGKAPKLLIK YASYLESGVP SRFSGSGSGT DFTLTISSLQ PEDFATYYCQ    360
HSREFPWTFG QGTKVEIKRA DAAPGGGGSG GGGSGGGGSE VQLVESGGGV VQPGGSLRLS    420
CAASGFTFSN YGMHWVRQAP EKGLEWVSYI SSGSSTIYYA DSVKGRFTIS RDNSKNTLYL    480
QMNSLRAEDT AVYYCARRGL LLDYWGQGTT VTVSS                              515

SEQ ID NO: 75           moltype = AA  length = 515
FEATURE                 Location/Qualifiers
source                  1..515
                        mol_type = protein
                        note = synthetic polypeptide
                        organism = synthetic construct
SEQUENCE: 75
DIQMTQSPSS LSASVGDRVT ITCRASKTVS TSSYSYMHWY QQKPGKAPKL LIKYASYLES     60
GVPSRFSGSG SGTDFTLTIS SLQPEDFATY YCQHSREFPW TFGQGTKVEI KRADAAPGGG    120
GSGGGGSGGG GSEVQLVESG GGDVKPGGSL RLSCAASGFT FSNYGMHWVR QAPEKGLEWV    180
SYISSGSSTI YYADSVKGRF TISRDNSKNT LYLQMNSLRA EDTAVYYCAR RGLLLDYWGQ    240
GTTVTVSSAS TKGPSVFPLA PLESSGSDIQ MTQSPSSLSA SVGDRVTITC RASKTVSTSS    300
YSYMHWYQQK PGKAPKLLIK YASYLESGVP SRFSGSGSGT DFTLTISSLQ PEDFATYYCQ    360
HSREFPWTFG QGTKVEIKRA DAAPGGGGSG GGGSGGGGSE VQLVESGGGD VKPGGSLRLS    420
CAASGFTFSN YGMHWVRQAP EKGLEWVSYI SSGSSTIYYA DSVKGRFTIS RDNSKNTLYL    480
QMNSLRAEDT AVYYCARRGL LLDYWGQGTT VTVSS                              515

SEQ ID NO: 76           moltype = AA  length = 515
FEATURE                 Location/Qualifiers
source                  1..515
                        mol_type = protein
                        note = synthetic polypeptide
                        organism = synthetic construct
SEQUENCE: 76
DIQMTQSPSS LSASLGDRAT ITCRASKTVS TSSYSYMHWY QQKPGQAPKL LIKYASYLES     60
GVPSRFSGSG SGTDFTLTIS SLQPEDFATY YCQHSREFPW TFGQGTKVEI KRADAAPGGG    120
GSGGGGSGGG GSEVQLVESG GGLVQPGGSL RLSCAASGFT FSNYGMHWVR QAPGKGLEWV    180
SYISSGSSTI YYADSVKGRF TISRDNAKNS LYLQMNSLRA EDTAVYYCAR RGLLLDYWGQ    240
GTTVTVSSAS TKGPSVFPLA PLESSGSDIQ MTQSPSSLSA SLGDRATITC RASKTVSTSS    300
```

```
YSYMHWYQQK PGQAPKLLIK YASYLESGVP SRFSGSGSGT DFTLTISSLQ PEDFATYYCQ   360
HSREFPWTFG QGTKVEIKRA DAAPGGGGSG GGGSGGGGSE VQLVESGGGL VQPGGSLRLS   420
CAASGFTFSN YGMHWVRQAP GKGLEWVSYI SSGSSTIYYA DSVKGRFTIS RDNAKNSLYL   480
QMNSLRAEDT AVYYCARRGL LLDYWGQGTT VTVSS                              515

SEQ ID NO: 77             moltype = AA   length = 446
FEATURE                   Location/Qualifiers
source                    1..446
                          mol_type = protein
                          note = synthetic polypeptide
                          organism = synthetic construct
SEQUENCE: 77
EVQLVESGGG LVQPGGSLRL SCAASGFTFS NYGMHWVRQA PGKGLEWVSY ISSGSSTIYY   60
ADSVKGRFTI SRDNAKNSLY LQMNSLRAED TAVYYCARRG LLLDYWGQGT TVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                        446

SEQ ID NO: 78             moltype = AA   length = 98
FEATURE                   Location/Qualifiers
source                    1..98
                          mol_type = protein
                          note = synthetic polypeptide
                          organism = synthetic construct
SEQUENCE: 78
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKV                           98

SEQ ID NO: 79             moltype = AA   length = 12
FEATURE                   Location/Qualifiers
source                    1..12
                          mol_type = protein
                          note = synthetic polypeptide
                          organism = synthetic construct
SEQUENCE: 79
EPKSCDKTHT CP                                                       12

SEQ ID NO: 80             moltype = AA   length = 113
FEATURE                   Location/Qualifiers
source                    1..113
                          mol_type = protein
                          note = synthetic polypeptide
                          organism = synthetic construct
SEQUENCE: 80
PCPAPEAAGG PSVFLFPPKP KDTLMISRTP EVTCVVVDVS HEDPEVKFNW YVDGVEVHNA   60
KTKPREEQYN STYRVVSVLT VLHQDWLNGK EYKCKVSNKA LPAPIEKTIS KAK          113

SEQ ID NO: 81             moltype = AA   length = 107
FEATURE                   Location/Qualifiers
source                    1..107
                          mol_type = protein
                          note = synthetic polypeptide
                          organism = synthetic construct
SEQUENCE: 81
GQPREPQVYT LPPSRDELTK NQVSLTCLVK GFYPSDIAVE WESNGQPENN YKTTPPVLDS   60
DGSFFLYSKL TVDKSRWQQG NVFSCSVMHE ALHNHYTQKS LSLSPGK                 107

SEQ ID NO: 82             moltype = AA   length = 446
FEATURE                   Location/Qualifiers
source                    1..446
                          mol_type = protein
                          note = synthetic polypeptide
                          organism = synthetic construct
SEQUENCE: 82
EVQLVESGGG LVQPGGSLRL SCAASGFTFS NYGMHWVRQA PGKGLEWVSY ISSGSSTIYY   60
ADSVKGRFTI SRDNAKNSLY LQMNSLRAED TAVYYCARRG LLLDYWGQGT TVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYDSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                        446

SEQ ID NO: 83             moltype = AA   length = 113
FEATURE                   Location/Qualifiers
source                    1..113
```

```
                              mol_type = protein
                              note = synthetic polypeptide
                              organism = synthetic construct
SEQUENCE: 83
PCPAPELLGG PSVFLFPPKP KDTLMISRTP EVTCVVVDVS HEDPEVKFNW YVDGVEVHNA    60
KTKPREEQYD STYRVVSVLT VLHQDWLNGK EYKCKVSNKA LPAPIEKTIS KAK          113

SEQ ID NO: 84                 moltype = AA  length = 446
FEATURE                       Location/Qualifiers
source                        1..446
                              mol_type = protein
                              note = synthetic polypeptide
                              organism = synthetic construct
SEQUENCE: 84
EVQLVESGGG LVQPGGSLRL SCAASGFTFS NYGMHWVRQA PGKGLEWVSY ISSGSSTIYY    60
ADSVKGRFTI SRDNAKNSLY LQMNSLRAED TAVYYCARRG LLLDYWGQGT TVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PEAAGGPSVF   240
LFPPKPKDTL MISRTPEVTC VVVDVSHEDP EVKFNWYVDG VEVHNAKTKP REEQYDSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                        446

SEQ ID NO: 85                 moltype = AA  length = 113
FEATURE                       Location/Qualifiers
source                        1..113
                              mol_type = protein
                              note = synthetic polypeptide
                              organism = synthetic construct
SEQUENCE: 85
PCPAPEAAGG PSVFLFPPKP KDTLMISRTP EVTCVVVDVS HEDPEVKFNW YVDGVEVHNA    60
KTKPREEQYD STYRVVSVLT VLHQDWLNGK EYKCKVSNKA LPAPIEKTIS KAK          113

SEQ ID NO: 86                 moltype = AA  length = 113
FEATURE                       Location/Qualifiers
source                        1..113
                              mol_type = protein
                              note = synthetic polypeptide
                              organism = synthetic construct
SEQUENCE: 86
PCPAPELLGG PSVFLFPPKP KDTLMISRTP EVTCVVVDVS HEDPEVKFNW YVDGVEVHNA    60
KTKPREEQYN STYRVVSVLT VLHQDWLNGK EYKCKVSNKA LPAPIEKTIS KAK          113

SEQ ID NO: 87                 moltype = AA  length = 218
FEATURE                       Location/Qualifiers
source                        1..218
                              mol_type = protein
                              note = synthetic polypeptide
                              organism = synthetic construct
SEQUENCE: 87
DIQMTQSPSS LSASLGDRAT ITCRASKTVS TSSYSYMHWY QQKPGQPPKL LIKYASYLES    60
GVPSRFSGSG SGTDFTLTIS SLQPEDAATY YCQHSREFPW TFGGGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 88                 moltype = AA  length = 31
FEATURE                       Location/Qualifiers
source                        1..31
                              mol_type = protein
                              note = synthetic polypeptide
                              organism = synthetic construct
SEQUENCE: 88
RASKSVSTSS YSYMHWYQQK PGQPPKLLIK Y                                   31

SEQ ID NO: 89                 moltype = AA  length = 31
FEATURE                       Location/Qualifiers
source                        1..31
                              mol_type = protein
                              note = synthetic polypeptide
                              organism = synthetic construct
SEQUENCE: 89
RASKTVSTSS YSYMHWYQQK PGQPPKLLIK Y                                   31

SEQ ID NO: 90                 moltype = AA  length = 33
FEATURE                       Location/Qualifiers
source                        1..33
                              mol_type = protein
                              note = synthetic polypeptide
                              organism = synthetic construct
```

```
SEQUENCE: 90
RVTITCRASK SVSTSSYSYM HWYQQKPGKA PKL                          33

SEQ ID NO: 91           moltype = AA  length = 32
FEATURE                 Location/Qualifiers
source                  1..32
                        mol_type = protein
                        note = synthetic polypeptide
                        organism = synthetic construct
VARIANT                 30
                        note = X=any amino acid, but preferentially is a basic
                         residue [R or K]
VARIANT                 1
                        note = X=any amino acid, but preferentially is a basic
                         residue [R or K]
SEQUENCE: 91
XRASKTVSTS SYSYMHWYQQ KPGQPPKLLX KY                           32

SEQ ID NO: 92           moltype = AA  length = 115
FEATURE                 Location/Qualifiers
source                  1..115
                        mol_type = protein
                        note = synthetic polypeptide
                        organism = synthetic construct
SEQUENCE: 92
EVQLVESGGG LVKPGGSRKL SCAASGFTFS DYGMHWVRQA PEKGLEWVAY ISSGSSTIYY   60
ADTVKGRFTI SRDNAKNTLF LQMTSLRSED TAMYYCARRG LLLDYWGQGT TLTVS       115

SEQ ID NO: 93           moltype = AA  length = 132
FEATURE                 Location/Qualifiers
source                  1..132
                        mol_type = protein
                        note = synthetic polypeptide
                        organism = synthetic construct
SEQUENCE: 93
DIVLTQSPAS LAVSLGQRAT ISCRASKSVS TSSYSYMHWY QQKPGQPPKL LIKYASYLES   60
GVPARFSGSG SGTDFTLNIH PVEEEDAATY YCQHSREFPW TFGGGTKLEI KRADAAPGGG  120
GSGGGGSGGG GS                                                     132
```